United States Patent [19]

Dixon et al.

[11] Patent Number: 4,740,620
[45] Date of Patent: Apr. 26, 1988

[54] ALKYLATION OF AROMATIC AMINES IN THE PRESENCE OF ACIDIC, CRYSTALLINE MOLECULAR SIEVES

[75] Inventors: Dale D. Dixon, Kutztown; William F. Burgoyne, Jr., Allentown, both of Pa.

[73] Assignee: Air Products and Chemicals, Inc., Allentown, Pa.

[21] Appl. No.: 796,465

[22] Filed: Nov. 8, 1985

[51] Int. Cl.$^4$ ............................................. C07C 85/24
[52] U.S. Cl. ..................................... 564/409; 564/307;
564/309; 564/315; 564/330; 560/43; 558/416;
558/418; 558/419; 502/73; 585/446
[58] Field of Search ............... 564/307, 309, 315, 330,
564/409; 560/43; 558/416, 418, 419; 502/73;
585/446

[56] References Cited

FOREIGN PATENT DOCUMENTS 6407639 1/1966 Netherlands .

OTHER PUBLICATIONS

Venuto, P. B. et al., "Organic Reactions Catalyzed by Crystalline Aluminosilicates", *J. of Catalysis*, vol. 4, pp. 81–98, (1966), Chemical Abstracts, vol. 83, No. 134815s.

*Primary Examiner*—Glennon H. Hollrah
*Assistant Examiner*—John A. Sopp
*Attorney, Agent, or Firm*—Russell L. Brewer; James C. Simmons; William F. Marsh

[57] ABSTRACT

This invention relates to a process for producing ring alkylated aromatic amines. In the process an aromatic amine is reacted with an olefin using an acidic crystalline molecular sieve as a catalyst. Under the conditions of the process the catalyst is extremely active and with amines that are capable of alkylation at the ortho and para positions, high selectivity to the ortho alkylated isomer can be achieved.

23 Claims, 3 Drawing Sheets

PRESSURE = 880-980 PSIG
LHSV (ANILINE) = 0.250 HR$^{-1}$
ANILINE/PROPYLENE MOLAR FEED RATIO = 1:10

ALKYLATION OF AROMATIC AMINES IN THE PRESENCE OF ACIDIC, CRYSTALLINE MOLECULAR SIEVES

TECHNICAL FIELD

This invention pertains to an improved process for alkylating aromatic amines in the presence of crystalline molecular sieves. In a preferred embodiment the process provides for the production of a reaction product wherein the ratio of ortho-alkylated aromatic amine to para-alkylated aromatic amine is high.

BACKGROUND OF THE INVENTION

Processes for alkylating a variety of alkylatable aromatic compounds by contacting such compounds with a hydrocarbon radical providing source such as an olefin or alcohol are widely known. Typically, alkylatable aromatic compounds are mononuclear aromatic compounds themselves or those substituted with a hydroxyl, amine or an ether group. The alkylation has been carried out in the presence of homogeneous and heterogeneous catalyst systems.

Ring alkylated aromatic amines have been some of the products produced by alkylation procedures. Ring alkylated aromatic amines have a variety of uses in chemical synthesis. Some of the early uses were intermediates for substituted isocyanates, herbicidal compositions, dyestuffs and textile auxiliary agents. More recently aromatic amines have been utilized as chain lengthening or cross-linking components in polyurethane systems. These are commonly referred to as chain extenders.

Representative references which illustrate some of the early processes in forming ring alkylated aromatic amines are:

British Pat. No. 414,574 discloses the reaction of aniline with various olefins, e.g., cyclohexene and alcohols, e.g., butanol in the presence of a neutral or weakly acidic catalyst system commonly referred to as hydrosilicates at temperatures from 200°-270° C. Ortho and para-cyclohexylaniline, N-cyclohexylaniline, N-butylaniline and para-methyl-ortho-cyclohexylaniline and N-cyclohexyl-para-toluidine are listed as representative products.

British Pat. No. 846,226 discloses ring alkylation of aromatic amines with olefins using active, substantially neutral bleaching earths of the montmorillonite type as a catalyst.

AS Pat. No. 1,051,271 discloses the ring alkylation of aniline with an olefin, e.g., ethylene, in the presence of kaolin or in the presence of aluminum and aluminum alloys. Alkylation with higher olefins, e.g., propylene, butylene, etc., was carried out in the presence of Friedel-Crafts catalysts or bleaching earths under liquid phase conditions at temperatures from 150°-350° C. Examples of catalytic systems included aluminum chloride, zinc chloride, boron trifluoride, sulfuric acid, phosphoric acid and bleaching earth. Ring alkylation at the ortho-position was predominant, although other products such as the di and tri-alkylated aniline product were produced.

In an article by Zollner and Marton, Acta Chim. Hung. Tomus 20, 1959 (Pages 321–329) the vapor phase alkylation of aniline with ethanol was effected in the presence of aluminum oxide.

U.S. Pat. No. 3,649,693 and U.S. Pat. No. 3,923,892 discloses the preparation of ring alkylated aromatic amines by reacting an aromatic amine with an olefin in the presence of aluminum anilide, optionally including a Friedel-Crafts promoter. Reaction products included 2-ethylaniline, and 2,6-diethylaniline.

Stroh, et al., in U.S. Pat. Nos. 3,275,690; 2,762,845, Japanese No. Sho 56-110652, and, as mentioned previously, AS Pat. No. 1,051,271, disclose various processes for preparing alkylated aromatic amines by reacting an aromatic amine with an olefin in the presence of Friedel-Crafts catalysts as well as a combination of the Friedel-Crafts catalysts in the presence of halogen compounds combined with aluminum. Representative reaction products included 2-cyclohexylaniline, diethyltoluenediamine, diethylaniline, diisopropylaniline and mono-tert-butylaniline.

The art, e.g., Netherlands Application No. 6,407,636 has recognized that alkylation of various aromatic and heterocyclic compounds can be carried out in the presence of an zeolite having a pore size from 6–15 Angstroms wherein active cationic sites are obtained with an exchangeable metal or hydrogen cations in their ordered internal structure. Alkylating agents include olefins having from 2 to 12 carbon atoms, alkyl halides such as propylbromide and ethylchloride; and alkanols, such as, methanol, ethanol, and propanol. Various compounds were suggested as being suited for alkylation and these include both the heterocyclic and aromatic ring compounds. For aromatic amine alkylation it was suggested that a zeolite with a disperse distribution of acidic sites should be utilized. It was believed the highly acidic zeolite catalysts which have a high density of acidic sites may bind the amine to the catalyst and block the pore structures. In Example 1 aniline was alkylated with propylene using sodium zeolite X having a pore size of 13 Angstroms and numerous alkylated amines were produced. Example 3 shows alkylation of diphenylamine with cyclohexene using a rare earth exchanged 13X zeolite. Again, numerous ring alkylated products were produced and high temperatures, e.g. 300° C. and above apparently being required to weaken the amine-acid bond.

French Pat. No. 1,406,739, which is equivalent to Netherlands Application No. 6,407,636, discloses the preparation of alkylated aromatic compounds having polar substitutions thereon utilizing alumino-silicates having a pore size of at least 6 Angstroms as a catalyst. Cations of low valence were deemed to have been particularly effective for the ring alkylation of aromatic compounds having weakly basic substituents such as aromatic amines. The examples show the alkylation of aniline with propylene in the presence of a sodium zeolite X and alkylation of diphenylamine with propylene in the presence of a molecular sieve 13X which has undergone a partial exchange with rare earths and having a pore size of 13Å.

U.S. Pat. No. 3,201,486 discloses prior art processes for alkylating various aromatic hydrocarbons with an olefin using sulfuric acid and hydrogen fluoride as a catalyst. In the particular reference solid phosphoric acid was used as the catalyst.

U.S. Pat. Nos. 3,178,365; 3,281,483; 4,259,537; 4,395,372 and 4,393,262 disclose the alkylation of aromatic hydrocarbon compounds with an olefin in the presence of various crystalline alumino-silicates, such as crystalline alumino-silicates having undergone previous transformation by reaction with a nitrogen oxide containing compound, a hydrogen mordenite, a ZSM catalyst exchanged with a VIa metal; crystalline aluminosilicates promoted with sulfur dioxide and dealuminated zeolites. The dealuminated, high silica zeolites are disclosed as having particular activity for the alkylation of benzene.

Although the prior art has disclosed that a variety of catalytic systems can be utilized in the alkylation of aromatic hydrocarbons and aromatic amines, the art also teaches that a variety of reaction products are produced, including both ortho and para-isomers of mononuclear aromatic amines as well as, mono, di and tri alkyl substituted amines. In addition the prior art teaches that neutral to weakly acidic catalysts are preferred for effecting ring alkylation of the aromatic amines. Even though the prior art has suggested preferred catalytic systems such systems also involve batch, liquid phase operation which may be difficult to operate over an extended period of time, and tend to give more para product. In addition, many of the processes suffer from poor conversion, poor reaction rate and an inability to produce high ortho to para isomer ratios at high conversion.

SUMMARY OF THE INVENTION

This invention pertains to a process for effecting alkylation of aromatic amines typically represented by the formulas:

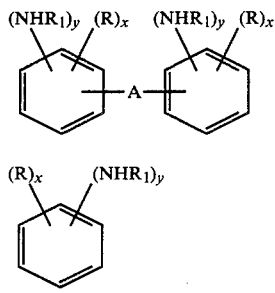

where R is hydrogen, $C_{1-10}$ alkyl, halogen, phenyl, alkoxy, ester or nitrile; $R_1$ is hydrogen or $C_{1-10}$ alkyl, x is 1 or 2; A is $C_{0-4}$ alkylene or NH, y is 1 or 2 except one y in formula I can be zero.

Some of the advantages associated with this invention include:

an ability to selectively produce alkylated aromatic amines where the alkyl groups is in the ortho position, i.e., ortho relative to the amine group, as opposed to the para position, and the alkylation is effected at high conversion;

an ability to effect ring alkylation at high rates;

an ability to utilize a fixed bed catalytic reactor lending itself to continuous vapor or liquid phase operation;

an ability to form ortho alkylates in high selectivity relative to N-alkylates; and an ability to initiate alkylation at low temperatures thus avoiding by-product oligomers and polymers.

THE DRAWINGS

DETAILED DESCRIPTION OF THE INVENTION

Figure 1:
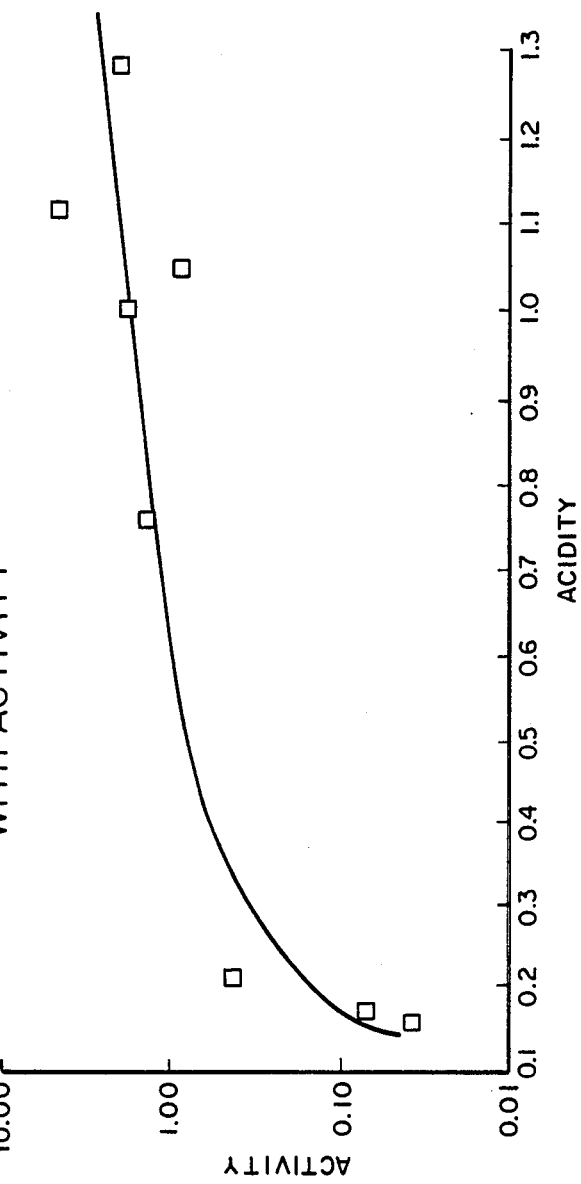
FIG. 1 is a plot of activity of the catalyst system versus its acidity.

As stated above ring alkylation of aromatic amines of this invention are represented by the formulas:

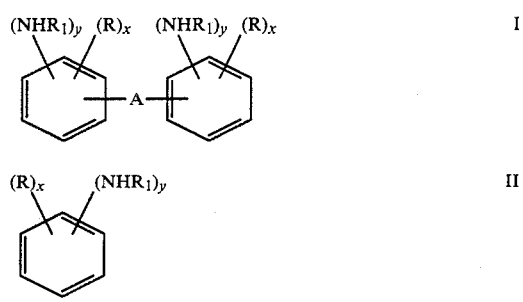

where R is hydrogen, $C_{1-10}$ alkyl or halogen, phenyl, alkoxy, ester, nitrile; $R_1$ is hydrogen or $C_{1-10}$ alkyl; X is 1 or 2, A is $C_{0-4}$ alkylene or NH, y is 1 or 2 except one y in formula I can be zero.

As shown in the above formulas, the aromatic amine can be monoamino or diamino substituted on the aromatic ring. Further, the aromatic amine can be substituted with a variety of substituents which are nonreactive with the olefin in the alkylation reaction. Examples of nonreactive substituents include alkylamino where the alkyl portion has from 1–6 carbon atoms, such as N-ethyl, N-propyl and N-tert-butyl, alkyl where the alkyl substituent has from 1–6 carbon atoms, e.g. ethyl, propyl, tert-butyl and cyclohexyl, methylcyclohexyl; alkoxy where the carbon content is from 2–6 carbon atoms, and ester, where the carbon content is from 2–6 carbon atoms.

Many of the amines included within the formulas I and II have hydrogen atoms which are reactive in both the ortho and para positions to the amino group. When both of these hydrogens are reactive to alkylation, one has the ability to selectively produce one isomer in favor of another. In the case of aromatic amines having hydrogen atoms which are reactive in both positions, but the para position is more thermodynamically stable. In most of the prior art systems, one could not simultaneously obtain high conversion of aromatic amine and high selectivity to an ortho-alkylated amine. If one went to high conversion of aromatic amine, one obtained higher percentages of the more stable para-isomer. Typically, low conversions, e.g., 20% to 30% were required to achieve a high production of ortho-isomer, e.g., an ortho-para isomer molar ratio of 3 or greater to 1. Aromatic amine compositions which have active hydrogen atoms, ortho and para to the amine group, are represented by the formulas:

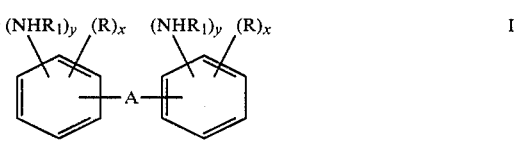

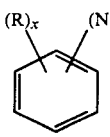 II where R is hydrogen, $C_{1-10}$ alkyl, phenyl, alkoxy, ester or nitrile; $R_1$ is hydrogen or $C_{1-10}$ alkyl, x is 1 or 2; A is $C_{0-4}$ alkylene or NH, y is 1 or 2 except one y in formula I can be zero.

Specific examples of aromatic amines suited for alkylation, which include those with active hydrogens in positions ortho and para to the amino group, are aniline, toluidine, xylidene, toluenediamine, xylidenediamine, diphenylamine, methylenedianiline, N-ethyl aniline, N-propyl aniline, (N-propylamino)aminotoluene, isobutylaniline, phenyl aniline, phenylenediamine and methylbenzylaniline. Those aromatics amines suited for alkylation having active hydrogen atoms in positions ortho and para to an amino group include aniline and diphenylamine.

Alkylating agents used for practicing the invention are mono aliphatic, acyclic and cyclic olefins such as ethylene, propylene, butene isobutylene, isoamylene, cyclohexene, 1-methylcyclohexene, 1-methylcyclopentene and halogenated derivatives. Typically, these olefins will have from 2 to 8 carbon atoms in the structure. Although in many reactions other materials are commonly used as alkylating agents; e.g., paraffin alcohols such as methanol, ethanol, propanol. While alkyl halides such as ethyl chloride, propyl bromide, etc. can be used, they generally are not suited for the ortho-alkylation of aromatic amines because the acid from the alkylation tends to interfere with the selectivity of the reaction. In the case where paraffin alcohols are employed, the water from the reaction system tends to reduce the ability of the aromatic amine to ring alkylate and when useful alkylation conditions, e.g., temperature, are achieved the product formed contains a high proportion of the para-isomer.

In the alkylation of aromatic amines, the molar ratio of olefin to aromatic amine influences the selectivity of the reaction. In those cases where the aromatic amine can be alkylated in the ortho and para positions, the molar ratio of olefin to aromatic amine influences, to some degree, whether the ring alkylation is ortho to the amine or para to the amine. Typically olefin to amine molar ratios will range from about 1 to 20 moles olefin per mole of aromatic amine and preferably 2–8 moles olefin per mole of aromatic amine. The utilization of higher mole ratios of olefin to aromatic amine tends to increase the amount of ortho-alkylated product produced.

The catalysts used in the reaction of the present invention are those crystalline molecular sieves which are solid phase and have an acidity factor of at least 0.30 and preferably at least 1. As a result these highly acidic molecular sieves have sufficient catalytic activity to effect ring-alkylation of the aromatic amine in high conversion (based upon amine) and in high selectivity. The crystalline molecular sieves include crystalline alumino-silicates, commonly referred to as zeolites, and they can be of both natural and synthetic material. Some of the zeolites are X, Y, K, L faujasite, mordenite, offretite, beta, omega, gmelinite, chabazite, clinoptilolite, heulandite, dachiarite, ferrierite, brewsterite, stilbite, epistilbite and the ZSM family. When initially prepared, the cation in the crystalline alumino-silicate usually is an alkali metal, typically sodium. This ion must be exchanged in sufficient proportion, generally in excess of 60%, with an acidic ion such as a rare earth metal, e.g. lanthanum, cerium, praseodymium; hydrogen or some of the transition metals such as nickel, copper, chromium and the like for the practice of this invention. The substitution of various ions for the sodium ion alters the acidity of the zeolite thus making it more reactive and catalytically effective for ring alkylation of the aromatic amine.

The naturally occurring and synthetic zeolites normally have a silica to alumina molar ratio of from 2 to 15:1. The acidity of the zeolite may be altered by a technique called dealumination. In effect, the practice of dealumination decreases the alumina content in the zeolite thereby increasing the silica to alumina ratio. The removal of alumina from the internal structure can also enlarge the cage structure or pore size of the zeolite to permit entry of and diffusion of larger molecules into its internal structure. It can also have tendency to increase catalyst acidity. Thus, one may be able to utilize a particular cation in a dealuminated zeolite but not use the same cation in its non-dealuminated counterpart since that catalyst would not meet the acidic requirements of this invention. Some of the techniques for dealumination include chelation, dehydration or acidification, the latter which entails the treatment of the zeolite with an inorganic acid. Such techniques for dealumination of zeolite are well known.

The zeolites are porous materials with the pores having generally uniform molecular dimensions. Cavities or cages are formed in the zeolite and are connected by channels of generally defined diameter. For the practice of this invention the cage diameter should be sufficiently large to permit the molecules to effectively enter the interior of the alumino-silicate for reaction and to exit as final product. Typically the pore size will range from about 6 to 15 Angstroms but the size of the pore required can vary depending upon the product being produced. An ethyl substituent can be prepared from a smaller pore zeolite than can a tert-butyl or cyclohexyl substituent. It also follows that a mononuclear aromatic amine can be produced with a smaller pore size zeolite than can a polynucleararomaticamine. If the pore size is too small or tortuous to permit entry of the reactants, conversion will be low at low temperatures and catalytic activity will be limited to surface catalysis. Higher temperatures may be required to enhance molecular diffusion as in the case of H-mordenite in propylene alkylation.

Molecular sieves have been developed which have been defined as nonzeolites but perform similarly in some reactions to zeolitic materials. They have a cage structure and typically contain alumina and silica in combination with other components, e.g., phosphorus, titania, etc. Representative crystalline molecular sieves are described in U.S. Pat. No. 4,440,871, European Pat. No. 124119 and European Pat. No. 121232 and are incorporated by reference. For purposes of this invention, these molecular sieves are deemed equivalent to and are to be included within the term crystalline molecular sieves.

Other nonalumino-silicate zeolites which can be used in the practice of the invention are the boron containing zeolites, e.g., borosilicates and borogermanates.

Sufficient alkali metal must be exchanged with appropriate acidic cations to render the crystalline molecular sieve acidic as defined by an acidity factor. This factor is determined by an ammonia absorption/desorption technique which involves treating the catalyst with ammonia at room temperature and then desorbing by heating to a temperature from ambient to 200° C. at 10°/minute, then holding at 200° C. for 2 hours. The amount of ammonia irreversibly adsorbed at 200° C. is indicative of acidity and indicative of the strength of the amine/acid bond. An acidity factor of 0.30 millimoles ammonia irreversibly adsorbed per gram of catalyst at 200° C. is necessary to obtain high catalytic activity and to obtain a high ortho to para isomer ratio at high conversion with those aromatic amines having hydrogen atoms which are reactive in both the ortho or para positions.

Although not intending to be bound by theory, it is believed that the high acidity of the zeolites is responsible for their high ortho-selectivity. The acid-catalyzed alkylation of aromatic amines involves competitive reaction at three active positions: N, o, and p (see Scheme 1).

ated isomers while the para-alkylates are the most stable and tend to be formed at higher temperatures. The high acidity of zeolites imparts high activity for ring alkylation relative to N-alkylation even at low temperatures. Since zeolites make it possible to form ring alkylates at relatively low temperatures, the ring alkylation step has high selectivity for the ortho-position rather than for the more thermodynamically stable para-position. Experiments utilizing appropriately deuterium labeled olefins indicate that the likely mechanism for acid-catalyzed ortho-alkylation occurs via a concerted reaction between aromatic amine and olefin as shown in path A of scheme 2. In other words, the concerted mechanism allows the amino functionality to direct the alkylation to the ortho-position. Catalysts that tend to form high amounts of N-alkylates and require higher temperatures for ring alkylation, e.g. silica-alumina and montmorillonite, tend to decrease the concertedness required for selective ortho-alkylation and tend to form comparatively more para-alkylates by paths D and C of scheme 2. Even higher temperatures will cause para-alkylates to form by path E.

SCHEME 1

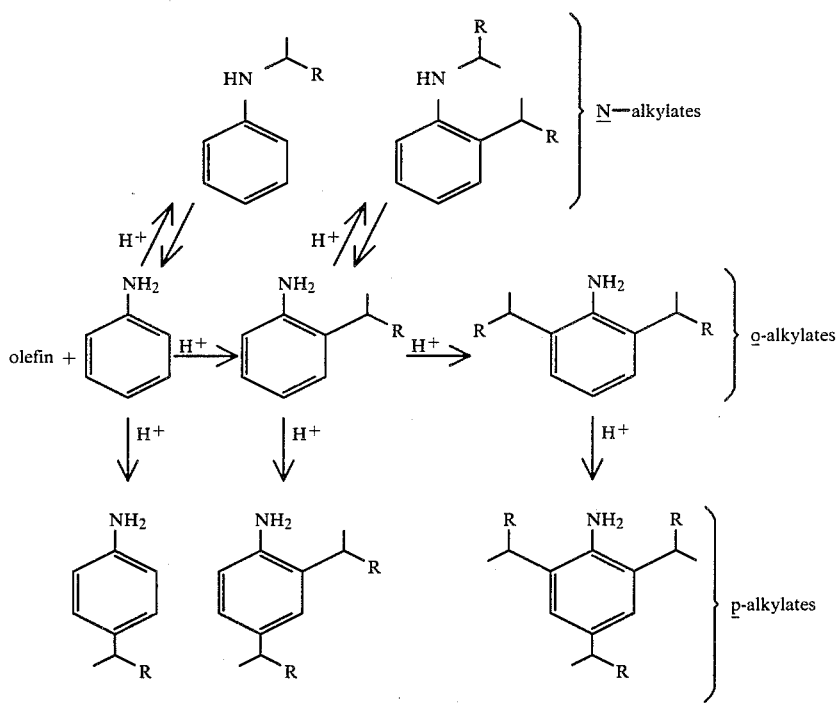

N-alkylates are formed at low temperatures and are the most thermodynamically unstable of the three alkyl-

SCHEME 2
Mechanism of Aniline Alkylation with Olefin

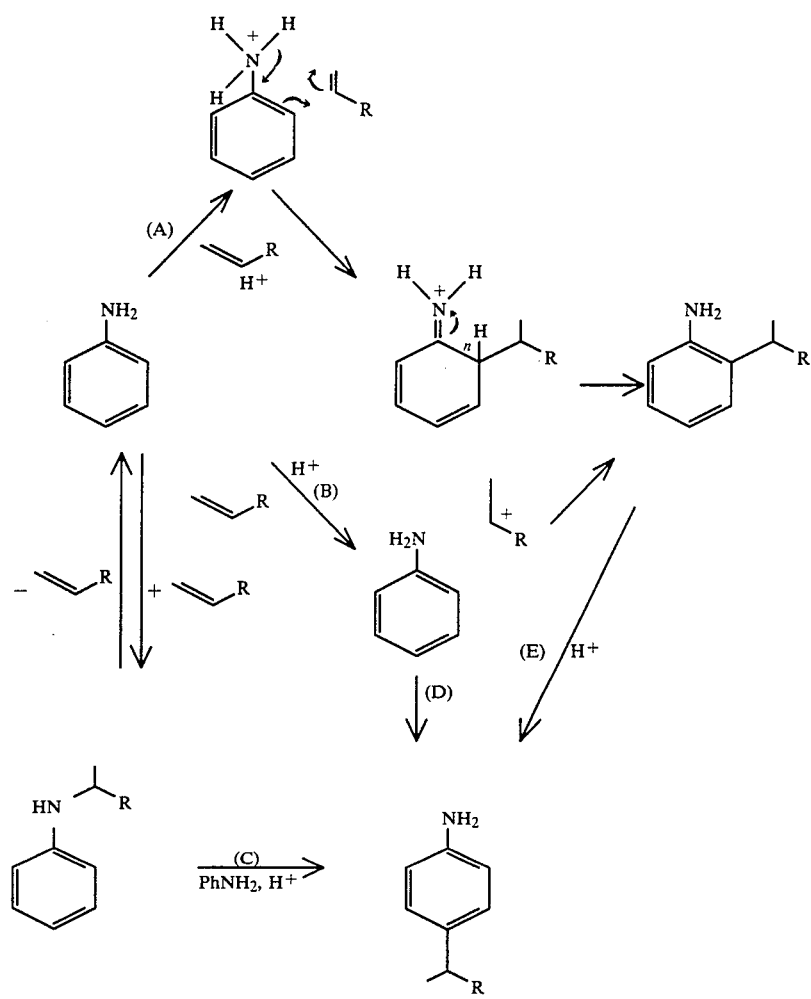

Figure 3:
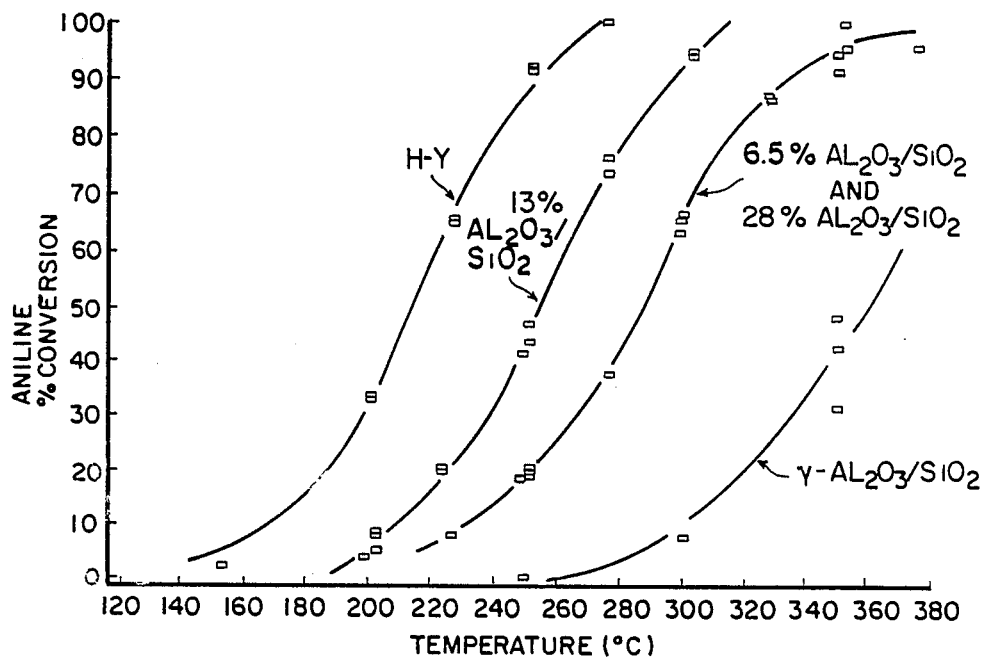
FIG. 3 is a plot of conversion as a function of temperature for several catalysts used in the alkylation of aniline with propylene.

It has also been observed that olefins which have difficulty in meeting the steric requirements for the concerted reaction (i.e. path A, scheme 2) for ortho-alkylation are especially sensitive to temperature. Olefins such as isobutylene and cyclohexene have a certain amount of steric resistance to the concerted pathway leading to selective ortho-alkylation. Consequently, obtaining an ortho-selective reaction with these olefins requires the lowest possible temperatures at which reaction proceeds. From FIG. 3 it can be seen that zeolites catalyze the olefin alkylation of aromatic amines at lower temperatures than other common heterogeneous acid catalysts.

Our experimental results indicate that the relative ease of N-alkylation vis-a-vis ring alkylation is also dependent on the substituents on the ring of the aromatic amine. Aromatic amines which have electron withdrawing groups on the ring (e.g. 2-fluoroaniline) tend to favor N-alkylation while aromatic amines having electron donating groups on the ring (e.g. o-toluidine) favor ring alkylation. From a mechanistic point of view, electron denating groups will stabilize the positively charged concerted pathway (i.e. path A, scheme 2) while electron withdrawing groups will have the opposite affect.

The alkylation of aromatic amines to effect ring alkylation of the aromatic amine can be carried out in a fixed bed reactor with the reactants being fed downflow or upflow through the reactor. The reaction can also be carried out in a stirred autoclave. Temperatures from 50° to 425° C. and pressures of from 50 to 3000 psig are utilized. Although conversion of an aromatic amine to a ring alkylated product may be greater at temperatures near the upper end of the range specified, the degree of alkylation in the ortho-position as opposed to the para-position may be greatly reduced and olefin polymerization may occur. Higher conversions obtained at high temperatures tend to form higher concentrations of the para-isomer. Thus, to obtain a reaction product with the highest ortho to para-isomer ratio the reaction temperature is controlled to produce a conversion range that will give the highest ortho to para-isomer ratio. For ethylene that temperature will probably be greater than the reaction temperature for propylene, the propylene temperature will be greater than for isobutylene. When an alkali metal or weakly acidic zeolite is used to effect ring alkylation of an alkylatable aromatic amine, the temperature required to achieve modest conversion is so high that substantially only para product is obtained. The advantage of an acidic catalyst as determined by the acidity factor permits one to achieve high conversion at lower temperature and these lower temperatures for ortho-alkylation permit high selectivity for ortho-isomer away from para-products and polymer.

In those systems employing an amine having hydrogen atoms which are active in both positions, ortho and para to the amine, the temperature of reaction should be sufficient to effect reaction but not exceed 375° C. for ethylene, 300° C. for propylene, 240° C. for isobutylene and 250° C. for cyclohexene.

Pressure has some effect on the selectivity to ortho-alkylated product but its effect is much less significant than temperature. Typically pressures used in the operation will range from 500 to 3000 psig for ethylene while pressures of from 50 to 1500 psig will be used for isobutylene.

Reaction time is an important factor in achieving high selectivity to an ortho-alkylated product as opposed to a para-alkylated product. Broadly, the reaction time can be expressed as liquid hourly space velocity (LHSV) of feed components to the reactor and typical values for liquid hourly space velocity are from 0.05 to 6 hours$^{-1}$. If one is operating at relatively high temperatures for the alkylation reaction, the LHSV should be increased somewhat as longer reaction times at high temperatures permit increased formation of the para-products. In contrast lower LHSV permit one to obtain high conversion at lower temperatures, low temperatures permitting ring alkylation at the ortho-position. Thus, by using a combination of an appropriate lower temperature range for a specific olefin and low LHSV one can obtain high conversion at high ortho to para ratios.

Liquid phase or vapor phase conditions may be utilized in the practice of the invention and the process may be carried out on a batch or continuous basis. When a batch process is utilized the proportion of aromatic amine is from about 5 to 100 weight parts per weight part catalyst.

The following examples are provided to illustrate various embodiments of the invention and are not intended to restrict the scope thereof.

EXAMPLE 1

Catalyst Preparation

A variety of catalysts were prepared and analyzed for acidity by the ammonia absorption/readsorption technique. The candidate zeolites used were sodium Y (code LZY-52), sodium X (LINDE 13X), and a thermally stabilized HY (LZY-82) supplied by the Linde Division of Union Carbide Corporation. A mordenite catalyst sold under the designation Z-900H was supplied by the Norton Company.

Rare earth salt solutions were utilized to partially exchange the sodium Y and X zeolites with rare earth metals and the salt solutions were obtained from Moly Corporation. These rare earth salt solutions were primarily rare earth chlorides and contain 19.4% lanthanum, 5.25% cerium, 2.65% praseodymium and 7.64% neodymium. Another rare earth salt solution used to exchange the zeolite consisted essentially of lanthanum trichloride hydrate and was obtained from Alpha Corporation.

Catalyst A: To fully exchange an X zeolite with a rare earth ion, 150 grams of sodium X zeolite were charged to a vessel and slurried with the rare earth chloride solution described above which had been diluted in a ratio of 1 to 1 on a parts by weight. A total of 900 cc of rare earth chloride solution was utilized. After slurrying, the mixture was heated under reflux for 2.5 hours, cooled and filtered. The previously treated zeolite was then recharged to the rare earth chloride solution heated, and refluxed for about 12 hours. After filtration, an additional exchange was carried out with 900 cc of solution at reflux temperatures for about 3 hours. The zeolite was then washed with water until the liquid was free of chloride solution. At that time it was dried in air at room temperature.

Catalyst B. A partially exchanged (70%) sodium X zeolite was prepared by charging 50 grams of sodium X zeolite to a vessel and slurrying with 46.62 grams of rare earth nitrate solution and diluting with 750 cc of water (pH=3.66). The mixture was then heated to reflux with stirring and held for 3.5 hours. The zeolite was then recovered from the solution by filtering and washed three times by stirring in 1 liter of distilled water for 30 minutes. The resulting catalyst was dried in air at room temperature.

Catalyst C. A partially exchanged (43%) sodium X zeolite was prepared by taking 13.98 grams of $LaCl_3 \times H_2O$ (32.5% $H_2O$) and dissolving in 750 cc's of water. The 50.08 grams of sodium X powder was added to the lanthanum chloride solution and the mixture heated under reflux for 16 hours. The zeolite was filtered and washed free of chloride ions with 3 successive washings in water. The catalyst was then dried in air.

Catalyst D. A partially exchanged (75%) rare earth Y zeolite was prepared by charging a 164 gram portion of sodium Y (LZY-52) zeolite catalyst into a vessel and stirring with 900 cc of dilute rare earth chloride solution (1:1 dilution) and the mixture refluxed for 3 hours. The second exchange was conducted with 900 cc of the rear earth chloride at reflux temperatures overnight. After filtration a third rare earth exchange was carried out by the same procedure utilized before. After such treatment the zeolite was filtered and washed until free of chloride ions. It was dried in air at room temperature.

Catalyst E. A partially dealuminated hydrogen-mordenite catalyst system was prepared by charging 199.2 grams of Zeolon 900H to a vessel and slurrying in a solution consisting of 172.2 ml of concentrated (37%) HCL, 317.5 grams of ammonium chloride and 2828 milliliters of distilled water. The mixture of catalyst and solution was stirred and heated to reflux for 5.5 hours. The acid solution was then removed and 3 liters of pure distilled water added and stirred with the zeolite. After several days this was replaced with fresh water and the mixture heated under reflux. This was repeated a total of three times until the pH of the wash solution was 4.5. The zeolite was then dried under vacuum at 150° C. for 3 hours.

Acidity measurements were performed on catalysts A through E using a duPont 1090 thermogravometric analysis system. In this procedure catalysts were first heated from ambient to 500° C. with the temperature being increased at a rate of 3° C. per minute. The temperature was held at 500° C. for 4 hours and the catalyst cooled to room temperature. A continuous helium flow of 100 cc per minute was maintained over the catalyst system. The desorption baseline as briefly described earlier involved heating from ambient to 200° C. from room temperature with an increase of 10° C. per minute and holding at 200° C. for 2 hours. The ammonia adsorption was effected by passing ammonia over the catalyst at room temperature until a constant weight was established. At that time the ammonia was turned off and 100 cc's per minute flow of helium established and the desorption temperature program recited above was repeated with the weight of the ammonia remaining on the catalyst at the end of the isothermal portions of the program being measured. Table 1 is an elemental analysis of the starting catalyst system and Table 2 sets forth the amount of irreversibly adsorbed ammonia remaining after the 200° C. desorption and is a measurement of the acidity factor.

TABLE 1

Elemental Analyses for Zeolite Catalysts

| Catalyst | SiO2 | Al2O3 | Na2O | RE2O3 | Si/Al | Formula |
|---|---|---|---|---|---|---|
| LZY52 | 64.9 | 22.7 | 13.43 | 0 | 2.39 | $Na_{56}(Al_2O_3)_{28}(SiO_2)_{136}$ |
| LZY82 | 74.5 | 22.3 | <0.31 | 0 | 2.78 | $H_{34}(NH_4)_{17}(Al_2O_3)_{25.5}(SiO_2)_{141}$ |
| NaX | 46.9 | 32.8 | 19.7 | 0 | 1.19 | $Na_{88}(Al_2O_3)_{44}(SiO_2)_{104}$ |
| Catalyst E H—Mordenite | 88.3 | 10.5 | <0.31 | 0 | 14.0 | $H_{3.2}(Al_2O_3)_{1.6}(SiO_2)_{44.8}$ |
| Catalyst A REX (fully exchanged) | 40.1 | 26.3 | <1.0 | 28.97 | 1.27 | $Na_3(RE)_{27}(Al_2O_3)_{42}(SiO_2)_{107}$ |
| Catalyst B REX (70% exchanged) | 45.3 | 30.4 | 5.7 | 21.44 | 1.24 | $Na_{26}(RE)_{20}(Al_2O_3)_{43}(SiO_2)_{106}$ |
| Catalyst C REX (43% exchanged) | 45.2 | 29.1 | 10.4 | 11.91 | 1.29 | $Na_{48}(RE)_{12}(Al_2O_3)_{42}(SiO_2)_{108}$ |
| Catalyst D REY (75% exchanged) | 62.8 | 21.6 | 2.9 | 16.7 | 2.42 | $Na_{14}RE_{14}(Al_2O_3)_{28}(SiO_2)_{136}$ |

TABLE 2

Amount of Irreversibly Adsorbed $NH_3$ for Zeolite Catalysts
Acidity Factor (200° C.)

| Catalyst | Irreversibly Adsorbed $NH_3$ (mmol/g) 200° C. |
|---|---|
| LZY52 (NaY) | 0.17 |
| LZY82 (HY) | 1.12 |
| NaX | 0.16 |
| Catalyst E H—Mordenite (dealuminated) | 1.05 |
| REX Catalyst A (fully exchanged) | 1.00 |
| REX Catalyst B (70% exchanged) | 0.76 |
| REX Catalyst C (43% exchanged) | 0.21 |
| REX Catalyst D (75% exchanged) | 1.28 |
| H—mordenite (commercial) | 0.89 |

EXAMPLE 2

Alkylation of Aniline with Propylene Using Zeolite Catalysts

Alkylation of aniline with propylene was effected in a continuous flow reactor. In the process the catalyst bed was first saturated with aniline at 900 psig and then the propylene was introduced into the reactor to provide a preselected mole ratio of aniline to propylene (N/R) over the bed. The reaction temperature then was raised slowly to a preselected temperature, typically 250° C. The products were recovered from the reactor and analyzed. Table 3 provides reactor data in terms of LHSV, mole ratio of aniline to propylene, (N/R), and reactor temperature in degrees Centigrade, Conversion was measured on the basis of amine converted to alkylated reaction product, and selectivity was defined as the moles of the specific product obtained divided by the total moles of product produced times 100. Catalyst activity ($k_1$) was defined as a psuedo-first order rate constant, the equation being $$\ln(1-X) \text{ times } LHSV = -k_1$$

where LHSV is expressed as cc aniline/cc cat-hr and X is the functional conversion of aniline reported.

TABLE 3

Reactor Data for Alkylation of Aniline with Propylene over Zeolite Catalysts

| Run | Catalyst | LHSV | N/R | T (°C.) | Conv (%) | $k_1 \times 10^3$ | N—Alkylate | o-Alkylate | p-Alkylate |
|---|---|---|---|---|---|---|---|---|---|
| 1 | REY | 0.250 | 0.2 | 250 | 50 | 1.89 | 24 | 71 | 5 |
| 2 | REY | 0.350 | 0.5 | 250 | 47 | 1.73 | 26 | 70 | 4 |
| 3 | REY | 0.350 | 0.5 | 250 | 41 | 2.02 | 26 | 70 | 4 |
| 4 | REX (fully exchanged) | 0.250 | 0.2 | 250 | 45 | 1.63 | 36 | 57 | 7 |
| 5 | REX (fully exchanged) | 0.250 | 0.5 | 250 | 40 | 1.39 | 37 | 56 | 7 |
| 6 | REX (fully exchanged) | 0.350 | 0.5 | 250 | 38 | 1.83 | 38 | 56 | 6 |
| 7 | HY | 0.350 | 0.2 | 250 | 77 | 5.61 | 23 | 69 | 8 |
| 8 | HY | 0.350 | 0.5 | 250 | 70 | 4.60 | 24 | 69 | 7 |
| 9 | H—Mordenite | 0.250 | 0.5 | 250 | 32 | 1.05 | 15 | 84 | 4 |
| 10 | H—Mordenite | 0.350 | 0.5 | 250 | 21 | 0.90 | 16 | 84 | 4 |
| 11 | H—Mordenite | 0.350 | 0.5 | 330 | 89 | 8.46 | 15 | 84 | 1 |
| 12 | NaX | 0.250 | 0.2 | 250 | 3 | 0.08 | 31 | 18 | 3 |
| 13 | NaX | 0.350 | 0.5 | 250 | 1 | 0.04 | 49 | 29 | 4 |
| 14 | NaX | 0.350 | 0.5 | 330 | 18 | 0.76 | 41 | 47 | 11 |

TABLE 3-continued

Reactor Data for Alkylation of Aniline with Propylene over Zeolite Catalysts

| Run | Catalyst | LHSV | N/R | T (°C.) | Conv (%) | $k_1 \times 10^3$ | Selectivities | | |
|---|---|---|---|---|---|---|---|---|---|
| | | | | | | | N—Alkylate | o-Alkylate | p-Alkylate |
| 15 | REX (70% exchanged) | 0.350 | 0.2 | 250 | 33 | 1.53 | 53 | 40 | 7 |
| 16 | REX (70% exchanged) | 0.350 | 0.5 | 250 | 31 | 1.39 | 55 | 39 | 6 |
| 17 | NaY | 0.350 | 0.5 | 250 | 2 | 0.07 | 45 | 51 | 4 |
| 18 | REX (43% exchanged) | 0.350 | 0.2 | 250 | 9 | 0.39 | 61 | 35 | 4 |
| 19 | REX (43% exchanged) | 0.350 | 0.5 | 250 | 10 | 0.42 | 61 | 34 | 4 |

Comparison of the total acidity, defined as the amount of irreversibly adsorbed $NH_3$ at 200° C. and the activity ($k_1$) for aniline alkylation with propylene is shown in FIG. 1. Although no simple linear correlation of the data exists, there is a clear distinction between the activity of the catalysts of the present invention, i.e., those with an acidity factor of at least 0.3 and catalysts utilized in the prior art. For example, compare the behavior of NaX, a preferred catalyst of French Pat. No. 1,406,739 having an acidity factor of 0.16 and a partially exchanged (43%) rare earth X having an acidity factor of 0.21 against H-Y having an acidity factor of 1.12 or H-mordenite having an acidity factor of 1.05. At temperatures of 250° C., the conversion of aniline over NaX was only 1-2% while the conversion over HY was 60-80%. To obtain higher conversions of aniline over NaX temperatures of 300+° C. were required. At 330° C., a conversion of 18% was obtained with fairly poor selectivity to ortho-alkylates (47%). H-Y Zeolite on the otherhand gave 70% selectivity to ortho-alkylates at 250° C. and 70-77% conversion. H-mordenite was extremely effective at higher temperatures effecting ring alkylation of aniline. At low temperatures, e.g., 200°-250° C. low conversions were recorded and this was believed due to cage structure restraint of molecular diffusion.

A partially exchanged (43%) rare earth exchanged zeolite having an acidity factor of 0.21 gave conversions of only 10% under conditions where the more acidic catalysts gave 30-70% conversion. Although the exchange of rare earth metals for sodium in the catalyst gave some improvement over NaX, it is still significantly less active than the fully exchanged, more acidic REX, a catalyst having an acidity factor of 1.00.

Figure 2:
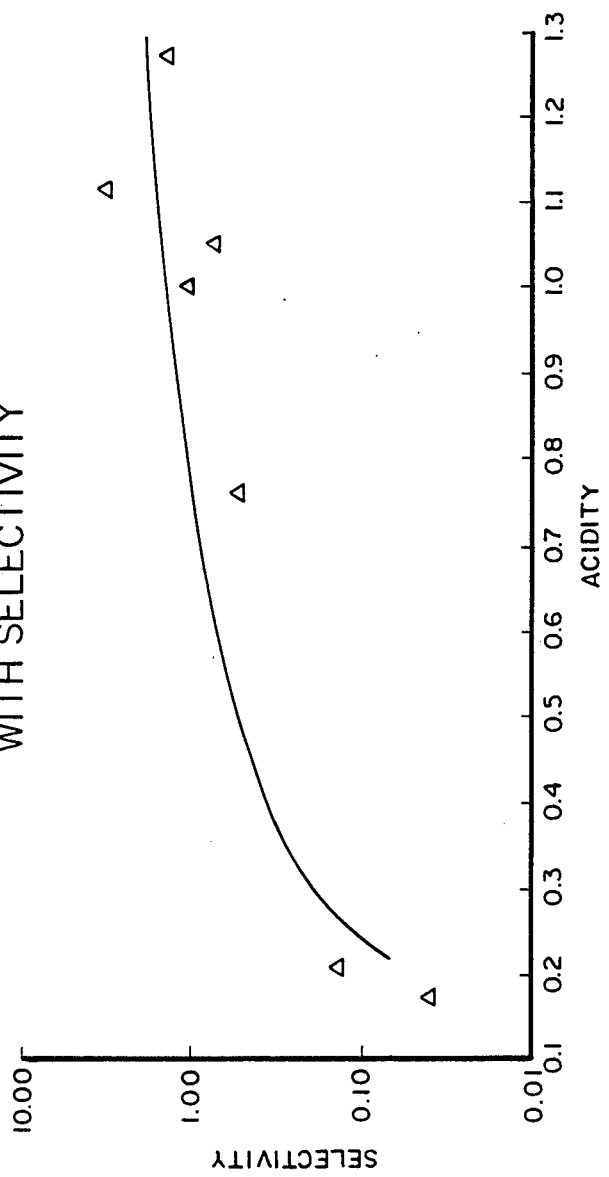
FIG. 2 is a plot of activity in producing ortho-alkylated aromatic amine versus acidity.

FIG. 2 displays the relationship between acidity and selectivity for ortho-alkylation. The log of the activity for ortho-alkylation vs. acidity is plotted in FIG. 1. It shows clearly that the use of strong, acidic catalysts are also more effective at ring alkylation than the basic catalytic materials of the prior art.

Analyzing the runs in the tables the following is noted. Runs 1-3 show that rare earth Y zeolite having an acidity factor of 1.28 gave better conversion and selectivity to ortho-alkylated product than the fully exchanged rare earth x zeolite runs 3-6) and the 70% and 43% rare earth exchanged zeolite (runs 15-19).

Sodium which had the lowest acidity factor gave the poorest results in terms of conversion (note runs 12-14). H-Y on the other hand, which had a high acidity factor, e.g., 1.12, showed conversions of 70 to 77% (runs 7-8) at 250° C. while sodium Y which had an acidity factor of 0.17 gave low conversions at 250° C.

EXAMPLE 3

Alkylation of Toluenediamine with Isobutylene over Zeolite

Isobutylene was reacted with toluenediamine in a stirred batch reactor. In this process approximately 200 grams of 2,4-toluenediamine was charged to the reactor along with 20 grams of catalyst. The reactor was then brought to reaction temperature and isobutylene pumped into the reactor to provide a molar ratio of isobutylene to toluenediamine of approximately 2:1. The reaction was carried out at a temperature of 180° C. for 4 hours.

The reaction product was analyzed by gas chromotography. Selectivity was defined in accordance with Example 2. The table summarizes the results:

N-alkylate=2N-t-butyl-2,4-toluenediamine plus 4N-t-butyl-2,4-toluenediamine.

Mixed=Mixed ring/N-alkylates=N,N'-di-t-butyl-2,4-toluenediamine plus 2N-5-di-t-butyl-toluenediamine.

| Catalyst | Conversion | N—alkylate | 5-t-butyl toluenediamine | Mixed |
|---|---|---|---|---|
| HY(LZY82) | 48 | 24 | 74 | 2 |
| NaX | 2 | 22 | 24 | 0 |

The results show excellent activity for the acidic HY zeolite while the sodium X zeolite was practically inactive at that reaction temperature. Selectivity to ring alkylate was high e.g. 3:1 ring to N-alkylate while selectivity to ring alkylate was low with NaX, e.g. 1:1 ring to N-alkylate.

EXAMPLE 4

Preparation of 5-isopropyl-2,4-toluenediamine and 3-isopropyl-2,6-toluenediamine over H-Y Zeolite (A)

A 40 gram portion of powdered HY-faujasite catalyst and 20 grams (1.64 moles) of 2,4-toluenediamine were charged to 1,000 cc pressure vessel equipped with a mechanical stirrer. A vessel was sealed and purged with nitrogen, and then pressurized to leave a residual 214 psig nitrogen blanket. The contents in the reactor were heated to 300° C. with stirring. At that time, 206 grams or 4.92 moles propylene were added to the reactor over a 30 minute period. On addition of the propylene the initial reaction pressure increased to 2,565 psig. The reaction mixture was maintained at 300° C. for twenty hours with constant stirring. During reaction, the pressure fell but no additional propylene was added.

The reaction product was recovered by first cooling the contents in the reactor to 150° C. and then discontinuing stirring. Residual propylene in the reactor was vented and the catalyst removed by a hot filtration technique. Analysis of the product by gas chromatographic techniques revealed the following products:

| Compound | Gas Chromotograph area percent |
| --- | --- |
| 2,4-toluenediamine | 43.9 |
| 5-isopropyl-2,4-toluenediamine | 54.11 |
| 3,5-diisopropyl-2,4-toluenediamine | 20.16 |
| other alkylated products | 21.34 |

(B)

The above (A) procedure was repeated except that 2,6-toluenediamine was substituted for the 2,4-toluenediamine reactant. On addition of propylene, the initial reaction pressure was 2,934 psig. Analysis of the reaction product, after isolation, showed the following:

| Compound | Gas Chromotograph area percent |
| --- | --- |
| 2,6-toluenediamine | 4.64 |
| 3-isopropyl-2,6-toluenediamine | 45.17 |
| 3,5-diisopropyl-2,6-toluenediamine | 30.70 |
| Other alkylated products | 19.49 |

The above example shows the excellent activity of the H-Y zeolite in the ring propylation of toluenediamine. Higher temperatures are generally required to effect high conversion to ring alkylated product, at least as compared to ring alkylation to toluenediamine with isobutylene. A homogeneous catalyst system using triethylaluminum and aniline of the type generally described in U.S. Pat. No. 3,275,690 gave much poorer results in terms of conversion.

EXAMPLE 5

Alkylation of a 80:20 Mixture with Isobutylene over H-Y zeolite

A 15.00 g. portion of H-Y zeolite (powder) having a pore size of 7.4 Angstroms, 120.0 g. (0.98 mol) of 2,4-toluenediamine, and 30.0 g. (0.25 mol) of 2,6-toluenediamine were charged to a 1000 cc Hastalloy C pressure vessel equipped with a mechanical stirrer. The vessel was sealed and purged with nitrogen, leaving a 217 psig nitrogen blanket. The contents were heated to 180° C. with stirring. Isobutylene (280 g., 4.98 mol) was then added over 15 minutes, resulting in an initial reaction pressure of 1271 psig. The reaction mixture was maintained at 180° C. for 18 hours with constant stirring and then cooled to 150° C. Stirring was discontinued at this time and the residual pressure was vented. The catalyst was removed by hot filtration, a product mixture of the following composition was obtained:

| | Mole % H—Y |
| --- | --- |
| 2,4-toluenediamine | 19.09 |
| 2,6-toluenediamine | 6.3 |
| 2-(tert-butylamino)-4-aminotoluene | 2.03 |
| 2-amino-4-(tert-butylamino)toluene | 8.11 |
| 5-tert-butyl-2,4-toluenediamine | 48.79 |
| 3-tert-butyl-2,6-toluenediamine | 12.73 |
| 2-(tert-butylamino)-5-tert-butyl- | 1.60 |

-continued

| | Mole % H—Y |
| --- | --- |
| 4-toluenediamine | |
| 2-amino-5-tert-butyl-4-(tert-butylamino) toluene | 0.55 |
| 2-(tert-butylamino)-5-tert-butyl-6-aminotoluene | Trace |
| 3,5-di-tert-butyl-2,6-toluenediamine | 0.81 |

These results show that the highly acidic H-Y zeolite was extremely effective in producing a mono-tert-butylated toluenediamine. There was a minor amount of N-butylated toluenediamine produced but this product is suited for recycle and conversion to ring alkylated product. Only a small percent, e.g., about 3% of ditertiary butyltoluenediamine products (including ring and N-alkylated) were produced while conversion was about 70%.

EXAMPLE 6

Preparation of 5-tert-butyl-2,4-toluenediamine over H-Y Zeolite

A 15.0 g. portion of powdered H-Y zeolite having a pore size of about 7.4 Angstroms and 150.0 g. (1.23 mol) of 2,4-toluenediamine were charged to a 1000 cc. Hastalloy C pressure vessel equipped with a mechanical stirrer. The vessel was sealed and purged with nitrogen leaving a residual 225 psig nitrogen blanket. The vessel contents were heated to 180° C. with stirring at 500 rpm. Isobutylene (279.0 g., 4.98 mol) was then added over 2 hours, resulting in 1225 psig vessel pressure. This provided a mole ratio of 4.05 isobutylene to 1 mole toluenediamine. The reaction mixture was maintained at 180° C. for 16 hours with constant stirring. The contents were cooled to 150° C. and then stirring was discontinued and the residual pressure vented. Removal of the catalyst by hot filtration afforded the following product mixture:

| | Mole % |
| --- | --- |
| 2,4-toluenediamine | 15.59 |
| 2-(tert-butylamino)-4-aminotoluene | 1.66 |
| 2-amino-4-(tert-butylamino)toluene | 8.02 |
| 5-tert-butyl-2,4-toluenediamine | 71.60 |
| 2,4-di(tert-butylamino)toluene | 0.20 |
| 2-tert-butylamino-5-tert-butyl-4-aminotoluene | 1.38 |
| 2-amino-5-tert-butyl-4-(tert-butylamino) toluene | 0.55 |

The above results show that highly acidic H-Y zeolite is effective for producing an tert-butylated toluenediamine with high selectivity to the mon-ring-tert-butyl-toluenediamine isomer and modest selectivity to the N-tert-butyltoluenediamine derivatives. Lesser quantities of di-tert-butylated products can be produced by operating at slightly lower temperature and thus at slightly lower conversion. Even so conversion was above 80% and less than 4% ditertiary product was produced.

EXAMPLE 7

Preparation of 3-tert-butyl-2,6-toluenediamine over H-Y Zeolite

A 15.0 g. portion of powdered H-Y zeolite catalyst and 140.0 g. (1.15 mol) of 2,6-toluenediamine were charged to a 1000 cc Hastalloy C pressure vessel equipped with a mechanical stirrer as was done in Example 2. The vessel was sealed and purged with nitrogen leaving a residual 200 psig nitrogen blanket at room temperature. The contents were heated to 180° C. with stirring. Isobutylene (267 g., 4.76 mol) was then added to the reaction mixture over 20 minutes, resulting in an initial reaction pressure of 1100 psig. This provided a molar ratio of 4.1:1 isobutylene to toluenediamine. The reaction mixture was maintained at 180° C. for 39 hours with constant stirring. The reaction product was isolated by the procedure used in Example 6 and consisted of the following composition:

|  | Mole % |
|---|---|
| 2,6-toluenediamine | 30.48 |
| 2-(tert-butylamino)-6-aminotoluene | 9.79 |
| 3-tert-butyl-2,6-toluenediamine | 56.13 |
| 2-(tert-butylamino)-5-tert-butyl-6-aminotoluene | 1.19 |
| 3,5-di-tert-butyl-2,6-toluenediamine | 1.28 |
|  | 100.00% |

The results in terms of conversion and selectivity were similar to those obtained for the conversion of the 2,4-isomer in Example 2. A lesser quantity of di-tert-butylated product can be produced at slightly lower conversion. Conversion was in excess of 70% and selectivity to ditertiary butyl isomers was less than 4%.

EXAMPLE 8

Synthesis of 3-tert-butyl-2,6-toluenediamine over silica-alumina

Synthesis of the above recited ortho-tert-butyltoluenediamine was carried out in a 1 gallon stainless steel pressure vessel equipped with a mechanical stirrer. The vessel was charged with a 150 gram portion of a powdered commercially available silica-alumina catalyst containing 13% alumina and 1500 grams (12.24 moles) of 2,6-toluenediamine. The autoclave was sealed and purged with nitrogen. A residual blanket of nitrogen was left in the autoclave, leaving the pressure at 16 psig. The contents of the reactor were heated to a temperature of 200° C. with constant agitation. Isobutylene was then introduced into the reactor and 870 grams or 15.5 moles were added over a 30 minute period resulting in an initial reaction pressure of 970 psig. This provided a mole ratio of 1.26:1 isobutylene to toluenediamine. The reaction mixture was maintained at 200° C. for about 45 hours with constant agitation.

At the end of the 45 hour reaction time the contents were cooled to about 150° C. and agitation discontinued. The reactor then was vented and the contents removed from the reactor. The catalyst was removed from the reaction mixture by filtration.

The reaction product was analyzed by gas chromatographic techniques and the following analysis was obtained:

|  | Mole Percent |
|---|---|
| 2,6-toluenediamine | 43.34 |
| 2-(tert-butylamino)-6-aminotoluene | 3.30 |
| 3-tert-butyl-2,6-toluenediamine | 42.36 |
| 3,5-di-tert-butyl-2,6-toluenediamine | 8.6 |
| 2-(tert-butylamino)-5-tert-butyl-6-aminotoluene | 1.82 |

Both the mono and di-tert-butyltoluenediamine products were produced. Conversion was somewhat lower than obtained with the H-Y Zeolite in Example 7.

EXAMPLE 9

Synthesis of 5-t-butyl-2,4-toluenediamine over HCl

A 300 cc Hastalloy C pressure vessel equipped with a mechanical stirrer was used for producing t-butyltoluenediamine. Approximately 100 grams or 0.819 moles of 2,4-toluenediamine were charged to the vessel along with 5 grams of 36% aqueous hydrochloric acid. The vessel was sealed and purged with nitrogen, leaving a 33 psig nitrogen blanket. The vessel contents then were heated to 180° C. with continuous stirring. Isobutylene then was introduced into the reactor and 53.4 grams or 0.96 moles was added over 15 minutes. On addition of the isobutylene, the pressure in the reactor increased to 766 psig. The reaction mixture was maintained at 180° C. for 24 hours with constant stirring. At the end of the 24 hour period the pressure had dropped to 524 psig. The contents were then cooled to 160° C. and stirring discontinued. At that time the reactor was vented and the reaction product analyzed for composition.

|  | Mole Percent |
|---|---|
| 2,4-toluenediamine | 50.70 |
| 2-(tert-butylamino)-4-aminotoluene | 1.84 |
| 2-amino-4-(tert-butylamino)toluene | 12.71 |
| 5-tert-butyl-2,4-toluenediamine | 26.71 |
| 2,4-di(tert-butylamino)toluene | 1.31 |
| 2-(tert-butylamino)-5-tert-butyl-4-aminotoluene | 5.28 |
| 2-amino-5-tert-butyl-4-(tert-butylamino)toluene | 1.45 |

Conversion is lower than in Example 6.

EXAMPLE 10

Synthesis of 5-tert-butyl-2,4-toluenediamine over montmorillonite

Synthesis of the above described t-butyltoluenediamine was accomplished using the procedure of Example 6 except that 15 grams of powdered montmorillonite clay were used in place of the silica-alumina catalyst and 150 g (1.23 moles) of the 2,4-toluenediamine were used as opposed to the 2,6-isomer. As in Example 6, the reactor contents were purged with nitrogen and then the contents were heated to 180° C. with stirring. Approximately 278 grams or 4.95 moles of isobutylene were then added to the reaction mixture over 20 minutes. The initial reaction pressure increased to 1210 psig and the contents maintained at 180° C. for 23 hours. At that time the contents were cooled to 150° C. and the reactor vented. The catalyst then was removed by hot filtration.

The reaction product was analyzed and contained the following:

| | Mole Percent |
|---|---|
| 2,4-toluenediamine | 57.82 |
| 2-(tert-butylamino)-4-aminotoluene | 5.49 |
| 2-amino-4-(tert-butylamino)toluene | 18.27 |
| 5-tert-butyl-2,4-toluenediamine | 16.85 |
| 2,4-di(tert-butylamino)toluene | 0.42 |
| 2-(tert-butylamino)-5-tert-butyl-4-aminotoluene | 0.47 |
| 2-amino-5-tert-butyl-4-(tert-butyl-amino)toluene | 0.27 |

Conversion of the toluenediamines was less than in Example 6 when H-Y Zeolite was used.

EXAMPLE 11

2-methyl-6-isopropyl aniline

2-Methyl-6-isopropyl aniline was prepared by the method of Example 2 using an H-Y zeolite catalyst for the condensation of aniline and propylene. The ortho-toluidine and propylene were fed to the reactor in a 1:5 molar ratio and at an LHSV of 0.25 based on o-toluidine. The reaction was conducted at 250° C. and 861 psig. The effluent product stream was analyzed by gas chromatography. Conversion of o-toluidine was 81.5%.

| | Wt. % |
|---|---|
| ortho-toluidine | 19.55 |
| N—isopropyl-2-methylaniline | 14.96 |
| 6-isopropyl-2-methylaniline | 57.10 |
| 4-isopropyl-2-methylaniline | 3.10 |
| other alkylation products | 10.58 |
| | 105.29 |

This example shows the effectiveness of a highly acidic catalyst to effect alkylation of an alkyl substituted aromatic amine. A high selectivity to the ortho-alkylated aromatic amine was achieved and the ratio of ring alkylate to N-alkylate was high, e.g., 4:1.

EXAMPLE 12

2-fluoro-6-isopropyl aniline 2-fluoro-6-isopropyl aniline was prepared by the method of Example 2 using an H-Y zeolite catalyst for the condensation of 2-aniline and propylene. In this reaction 2-fluoroaniline and propylene were fed to a reactor in a 1:5 mole ratio and LHSV of 0.25 based on 2-fluoroaniline. The reaction was conducted at 255° C. and 879 psig. The effluent product stream was analyzed by gas chromatography. Conversion of 2-fluoroaniline was 71.2%.

| | Wt. % |
|---|---|
| 2-fluoroaniline | 28.80 |
| N—isopropyl-2-fluoroaniline | 31.36 |
| 2-fluoro-6-isopropylaniline | 26.12 |
| 2-fluoro-4-isopropylaniline | 5.66 |
| other alkylated products | 6.80 |
| | 98.74 |

As in Example 11 the catalyst was effective for alkylating a substituted aromatic composition but one substituted with a halogen atom instead of alkyl group and in relatively high yield. Good selectivity to the ortho-alkylated aniline derivative was achieved. Because of the electron withdrawing character of the fluorine atom, a little higher temperature could be utilized to obtain higher ring alkylation and reduced N-alkylation.

EXAMPLE 13

2-chloro-6-isopropyl aniline 2-chloro-6-isopropyl aniline was prepared by the method of Example 2 using an H-Y zeolite catalyst for the condensation of aniline and propylene. 2-chloroaniline and propylene were fed to the reactor in a 1:5 mole ratio and LHSV of 0.25 based on 2-chloroaniline. The reaction was conducted at 250° C. and 1343 psig. The effluent product stream was analyzed by gas chromatography. Conversion of 2-chloroaniline was 72%.

| | Wt. % |
|---|---|
| 2-chloroaniline | 18.08 |
| N—isopropyl-2-chloroaniline | 38.11 |
| 2-chloro-6-isopropylaniline | 18.59 |
| 2-chloro-4-isopropylaniline | 5.88 |
| other alkylation products | 22.16 |
| | 102.82 |

As in Example 12 good yields to alkylated aromatic amine were achieved, although a higher than usual N/ring ratio was formed due to the electron withdrawing properties of chlorine. Perhaps a higher temperature, e.g., to 275° C. would reduce N-alkylation.

EXAMPLE 14

Alkylation of ortho-phenylenediamine with propylene over H-Y zeolite catalyst

A 100.0 g (0.92 mol) portion of ortho-phenylenediamine and 20.0 g of H-Y zeolite were charged to a 1000 cc pressure vessel equipped with a mechanical stirrer. The vessel was sealed and purged with nitrogen, leaving a 212 psig nitrogen blanket. The vessel contents were heated to 277° C. with stirring. Propylene (155. g, 3.70 mol) was then added over 15 min., resulting in an initial reaction pressure of 1990 psig; the mixture was maintained at 277° C. for 21 hr. with constant stirring, after which time, the pressure dropped to 1514 psig. The contents were then cooled to 150° C., and a catalyst free sample was obtained by hot filtration. The sample gave the following olefin free analysis by gas chromatography:

| Composition | GC Area % |
|---|---|
| 1,2-benzenediamine | 0.68 |
| 2N—isopropyl-1,2 benzenediamine | 0.63 |
| 6-isopropyl-1,2-benzenediamine | 20.90 |
| 5-isopropyl 1,2-benzenediamine | 0.53 |
| 2N—isopropyl-6-isopropyl-1,2-benzenediamine | 6.21 |
| 3,6-diisopropyl-1,2-benzenediamine | 31.80 |
| 3,5-diisopropyl-1,2-benzenediamine | 9.21 |
| Other Alkylated Products | 30.04 |
| | 100% |

EXAMPLE 15

Alkylation of Aniline with Olefins

A series of alkylation reactions was run using aniline as a model reactant since it has active sites at both the ortho-and-para positions tot the amino group. The reactions were carried out in a fixed bed catalytic reactor, the reactor consisting of a 0.5 inch ID, 304 stainless steel tube which was jacketed with a single-element heater.

A 5 cc Vicor preheating bed was used to vaporize the reactants as they were passed downflow through the stainless steel tube jacketed reactor. The reactor was of sufficient length to accommodate from about 12 to 25 cubic centimeters of a solid phase catalyst system.

The reactants were charged to the preheater, vaporzied and then reacted in the presence of a catalyst. The reaction product was collected and by product olefin was removed via vaporization. The reaction product then was analyzed (free of olefin) by gas chromotography using an internal standard technique.

Tables 4-24 below are the results of alkylation runs listing reactants, process conditions, e.g. temperature in °C., pressure in psig, liquid hourly space velocity (LHSV), catalyst, moles of aromatic amine (N), moles olefin (R), conversion, and ortho-para isomer ratios (O-P). OBS is a line number for each table to aid in quick identification for results on that table. The term ortho to para ratio is the ratio of combined wt% of product 2, and 2,6-isomers divided by the combined weight % of the 4; 2,4-; and 2,4,6-isomers. Run is an arbitrary run number and is provided to facilitate quick review of results in other tables where there has been a sorting of the data as for example ascending pressure, ascending conversion or ascending ortho-para ratio. The various sorting of the data affords an ability to observe trends and make determinations as to the effect of temperature, pressure and space velocity, on conversion and e.g., ortho-para selectivity in the alkylation with specific olefinic reactants.

In the analytical portion of the table the following abbreviated codes have been utilized to identify the following products.

N-IPA refers to N-isopropyl aniline.
2-IPA refers to 2-isopropyl aniline or ortho-isopropyl aniline.
4-IPA refers to 4-isopropyl aniline or para-isopropyl aniline.
N,2-DIPA refers to N,2-diisopropyl aniline.
2,4-DIPA refers to 2,4-diisopropyl aniline.
2,6-DIPA refers to 2,6-diisopropyl aniline; and 2,4,6-TIPA refers to 2,4,6-triisopropyl aniline.
N-t-butyl aniline refers to N-tert-butyl aniline.
O-t-butyl aniline refers to ortho-tert-butyl aniline.
P-t-butyl aniline refers to para-tert-butyl aniline.
N,2-dibut aniline refers to N,2-di-tert-butyl aniline.
2,4-dibut aniline refers to 2,4-di-tert-butyl aniline.
N-cylohexaniline refers to N-cyclohexyl-aniline.
O-cyclohexaniline refers to ortho-cyclohexyl-aniline.
P-cyclohexaniline refers to para-cyclohexyl-aniline.
N,2-dihexaniline refers to N,2-dicyclohexyl-aniline.
2,4-dihexaniline refers to 2,4-dicyclohexyl-aniline.
2,6-dihexaniline refers to 2,6-dicyclohexyl-aniline.

TABLE 4

ANILINE/PROPYLENE/ZEOLITES
Sorted by Temperature

| OBS | SAMPLE ID | RUN | TEMPERATURE | PRESSURE | N | R | CATALYST TYPE | LHSV | CONV | O_P |
|---|---|---|---|---|---|---|---|---|---|---|
| 1 | 7171-41-03 | 1 | 154 | 930 | 1.00 | 10.00 | H—MORDENITE | 0.25 | 2.46 | . |
| 2 | 7644-96-13 | 2 | 201 | 769 | 1.00 | 1.00 | H—MORDENITE | 0.13 | 0.61 | . |
| 3 | 7171-41-06 | 3 | 201 | 950 | 1.00 | 10.00 | H—MORDENITE | 0.25 | 4.40 | . |
| 4 | 7644-96-14 | 4 | 202 | 927 | 1.00 | 2.00 | H—MORDENITE | 0.13 | 0.63 | . |
| 5 | 7644-53-03 | 5 | 204 | 840 | 1.00 | 1.00 | H—MORDENITE | 0.13 | 4.73 | . |
| 6 | 7723-54-19 | 6 | 208 | 967 | 1.00 | 2.00 | H—MORDENITE | 0.13 | 0.31 | . |
| 7 | 7723-54-20 | 7 | 208 | 963 | 1.00 | 2.00 | H—MORDENITE | 0.13 | 0.21 | . |
| 8 | 7644-96-15 | 8 | 227 | 917 | 1.00 | 2.00 | H—MORDENITE | 0.13 | 2.83 | 24.29 |
| 9 | 7171-43-09 | 9 | 227 | 949 | 1.00 | 10.00 | H—MORDENITE | 0.25 | 5.07 | . |
| 10 | 7723-56-24 | 10 | 228 | 985 | 1.00 | 2.00 | H—MORDENITE | 0.13 | 6.62 | . |
| 11 | 7723-56-25 | 11 | 228 | 978 | 1.00 | 2.00 | H—MORDENITE | 0.13 | 7.10 | . |
| 12 | 7723-49-04 | 12 | 228 | 957 | 1.00 | 2.00 | H—MORDENITE | 0.13 | 3.10 | . |
| 13 | 7723-49-05 | 13 | 228 | 990 | 1.00 | 2.00 | H—MORDENITE | 0.13 | 2.68 | . |
| 14 | 7171-43-17 | 14 | 228 | 956 | 1.00 | 10.00 | H—MORDENITE | 0.25 | 2.61 | . |
| 15 | 7723-57-26 | 15 | 247 | 990 | 1.00 | 2.00 | H—MORDENITE | 0.13 | 6.98 | . |
| 16 | 7644-97-16 | 16 | 252 | 919 | 1.00 | 2.00 | H—MORDENITE | 0.13 | 9.65 | 20.40 |
| 17 | 7644-97-17 | 17 | 252 | 914 | 1.00 | 2.00 | H—MORDENITE | 0.13 | 9.90 | 20.38 |
| 18 | 7644-54-04 | 18 | 252 | 836 | 1.00 | 1.00 | H—MORDENITE | 0.13 | 7.92 | . |
| 19 | 7644-54-05 | 19 | 252 | 834 | 1.00 | 1.00 | H—MORDENITE | 0.13 | 9.79 | 15.08 |
| 20 | 7644-54-06 | 20 | 252 | 847 | 1.00 | 2.00 | H—MORDENITE | 0.13 | 9.78 | 15.00 |
| 21 | 7644-55-07 | 21 | 252 | 840 | 1.00 | 2.00 | H—MORDENITE | 0.13 | 12.84 | 15.51 |
| 22 | 7171-43-11 | 22 | 252 | 956 | 1.00 | 10.00 | H—MORDENITE | 0.25 | 9.00 | . |
| 23 | 7723-62-45 | 23 | 261 | 1008 | 1.00 | 2.00 | H—MORDENITE | 0.13 | 12.05 | 15.22 |
| 24 | 7723-62-46 | 24 | 261 | 1006 | 1.00 | 2.00 | H—MORDENITE | 0.13 | 14.18 | 14.92 |
| 25 | 7723-64-51 | 25 | 262 | 910 | 1.00 | 2.00 | H—MORDENITE | 0.03 | 47.35 | 14.57 |
| 26 | 7723-64-53 | 26 | 262 | 1000 | 1.00 | 2.00 | H—MORDENITE | 0.03 | 45.95 | 14.51 |
| 27 | 7723-65-56 | 27 | 262 | 1002 | 1.00 | 2.00 | H—MORDENITE | 0.03 | 48.15 | 14.51 |
| 28 | 7723-57-28 | 28 | 271 | 1000 | 1.00 | 2.00 | H—MORDENITE | 0.13 | 23.38 | 14.14 |
| 29 | 7723-57-30 | 29 | 271 | 1005 | 1.00 | 2.00 | H—MORDENITE | 0.13 | 25.95 | 14.85 |
| 30 | 7723-58-34 | 30 | 271 | 1000 | 1.00 | 2.00 | H—MORDENITE | 0.13 | 44.47 | 12.26 |
| 31 | 7723-58-36 | 31 | 271 | 1004 | 1.00 | 2.00 | H—MORDENITE | 0.13 | 47.80 | 12.38 |
| 32 | 7723-59-37 | 32 | 271 | 1004 | 1.00 | 2.00 | H—MORDENITE | 0.13 | 46.04 | 12.12 |
| 33 | 7723-59-38 | 33 | 271 | 1000 | 1.00 | 2.00 | H—MORDENITE | 0.13 | 48.61 | 12.17 |
| 34 | 7644-74-10 | 34 | 274 | 834 | 1.00 | 2.00 | H—MORDENITE | 0.06 | 32.32 | 9.76 |
| 35 | 7723-66-61 | 35 | 275 | 997 | 1.00 | 2.00 | H—MORDENITE | 0.03 | 58.95 | 12.12 |
| 36 | 7723-66-62 | 36 | 275 | 927 | 1.00 | 2.00 | H—MORDENITE | 0.03 | 56.41 | 12.05 |
| 37 | 7723-67-67 | 37 | 276 | 1020 | 1.00 | 10.00 | H—MORDENITE | 0.12 | 19.80 | 12.50 |
| 38 | 7723-67-69 | 38 | 276 | 1020 | 1.00 | 10.00 | H—MORDENITE | 0.12 | 19.09 | 12.70 |
| 39 | 7723-68-74 | 39 | 276 | 1013 | 1.00 | 10.00 | H—MORDENITE | 0.03 | 62.56 | 10.52 |
| 40 | 7723-69-77 | 40 | 276 | 1015 | 1.00 | 10.00 | H—MORDENITE | 0.03 | 52.60 | 11.46 |
| 41 | 7723-69-78 | 41 | 276 | 1011 | 1.00 | 10.00 | H—MORDENITE | 0.03 | 53.99 | 11.86 |
| 42 | 7644-97-18 | 42 | 277 | 920 | 1.00 | 2.00 | H—MORDENITE | 0.13 | 18.08 | 13.75 |
| 43 | 7171-43-14 | 43 | 277 | 956 | 1.00 | 10.00 | H—MORDENITE | 0.25 | 16.85 | 12.92 |
| 44 | 7644-97-19 | 44 | 301 | 918 | 1.00 | 2.00 | H—MORDENITE | 0.13 | 25.10 | 9.44 |
| 45 | 7644-98-20 | 45 | 301 | 915 | 1.00 | 2.00 | H—MORDENITE | 0.06 | 33.15 | 13.58 |

TABLE 4-continued
ANILINE/PROPYLENE/ZEOLITES
Sorted by Temperature

| OBS | SAMPLE ID | RUN | TEMPERATURE | PRESSURE | N | R | CATALYST TYPE | LHSV | CONV | O_P |
|---|---|---|---|---|---|---|---|---|---|---|
| 46 | 7432-08-05 | 46 | 150 | 883 | 1.00 | 1.00 | H—Y | 0.13 | 9.89 | . |
| 47 | 7432-09-06 | 47 | 150 | 883 | 1.00 | 1.00 | H—Y | 0.13 | 6.07 | . |
| 48 | 7171-37-02 | 48 | 154 | 960 | 1.00 | 11.80 | H—Y | 0.25 | 1.56 | . |
| 49 | 7171-37-03 | 49 | 154 | 962 | 1.00 | 10.00 | H—Y | 0.25 | 1.65 | . |
| 50 | 7432-11-11 | 50 | 167 | 910 | 1.00 | 2.00 | H—Y | 0.06 | 19.08 | . |
| 51 | 7432-11-12 | 51 | 167 | 910 | 1.00 | 2.00 | H—Y | 0.06 | 17.97 | . |
| 52 | 7432-12-12 | 52 | 167 | 913 | 1.00 | 1.00 | H—Y | 0.06 | 18.03 | . |
| 53 | 7432-12-13 | 53 | 167 | 911 | 1.00 | 1.00 | H—Y | 0.06 | 18.00 | . |
| 54 | 7432-10-09 | 54 | 182 | 911 | 1.00 | 2.00 | H—Y | 0.13 | 22.46 | 34.17 |
| 55 | 7432-10-10 | 55 | 182 | 918 | 1.00 | 2.00 | H—Y | 0.13 | 21.39 | . |
| 56 | 7171-38-05 | 56 | 202 | 972 | 1.00 | 10.00 | H—Y | 0.25 | 24.12 | 17.11 |
| 57 | 7171-38-16 | 57 | 202 | 972 | 1.00 | 10.00 | H—Y | 0.25 | 24.85 | 17.35 |
| 58 | 7432-09-07 | 58 | 203 | 907 | 1.00 | 10.00 | H—Y | 0.25 | 29.58 | 22.57 |
| 59 | 7432-09-08 | 59 | 203 | 910 | 1.00 | 10.00 | H—Y | 0.25 | 29.21 | 28.91 |
| 60 | 7432-15-19 | 60 | 226 | 918 | 2.00 | 1.00 | H—Y | 0.06 | 50.12 | 10.51 |
| 61 | 7432-15-20 | 61 | 226 | 918 | 2.00 | 1.00 | H—Y | 0.06 | 51.76 | 10.34 |
| 62 | 7432-23-22 | 62 | 226 | 928 | 4.00 | 1.00 | H—Y | 0.06 | 18.19 | 14.42 |
| 63 | 7432-14-16 | 63 | 227 | 928 | 1.00 | 1.00 | H—Y | 0.06 | 53.55 | 9.54 |
| 64 | 7432-14-18 | 64 | 227 | 930 | 1.00 | 1.00 | H—Y | 0.06 | 50.67 | 9.40 |
| 65 | 7432-23-23 | 65 | 227 | 931 | 4.00 | 1.00 | H—Y | 0.06 | 20.78 | 13.59 |
| 66 | 7171-38-18 | 66 | 228 | 990 | 1.00 | 10.00 | H—Y | 0.25 | 48.76 | 10.80 |
| 67 | 7171-39-09 | 67 | 228 | 985 | 1.00 | 10.00 | H—Y | 0.25 | 49.47 | 10.80 |
| 68 | 7171-40-17 | 68 | 228 | 913 | 1.00 | 10.00 | H—Y | 0.25 | 44.31 | 11.34 |
| 69 | 7171-40-18 | 69 | 228 | 913 | 1.00 | 10.00 | H—Y | 0.25 | 44.20 | 11.31 |
| 70 | 7723-19-33 | 70 | 228 | 1021 | 1.00 | 10.00 | H—Y | 0.06 | 80.68 | 11.21 |
| 71 | 7723-19-34 | 71 | 228 | 1024 | 1.00 | 10.00 | H—Y | 0.06 | 81.03 | 11.15 |
| 72 | 7171-39-11 | 72 | 253 | 988 | 1.00 | 10.00 | H—Y | 0.25 | 78.53 | 5.62 |
| 73 | 7171-39-12 | 73 | 253 | 988 | 1.00 | 10.00 | H—Y | 0.25 | 79.72 | 5.55 |
| 74 | 7171-39-14 | 74 | 277 | 985 | 1.00 | 10.00 | H—Y | 0.25 | 100.00 | 0.78 |
| 75 | 7171-39-15 | 75 | 277 | 986 | 1.00 | 10.00 | H—Y | 0.25 | 100.00 | 0.76 |

TABLE 5
ANILINE/PROPYLENE/ZEOLITES
Sorted by Temperature

| OBS | RUN | ANILINE MOLE PCT | N—IPA MOLE PCT | 2-IPA MOLE PCT | 4-IPA MOLE PCT | N,2-DIPA MOLE PCT | 2,4-DIPA MOLE PCT | 2,6-DIPA MOLE PCT | 2,4,6-TIPA MOLE PCT | CONV | O_P |
|---|---|---|---|---|---|---|---|---|---|---|---|
| 1 | 1 | 96.65 | 0.88 | 1.45 | 0.00 | 0.00 | 0.00 | 0.00 | 0.00 | 2.46 | . |
| 2 | 2 | 99.39 | 0.00 | 0.13 | 0.00 | 0.00 | 0.00 | 0.00 | 0.00 | 0.61 | . |
| 3 | 3 | 94.37 | 1.23 | 2.77 | 0.00 | 0.00 | 0.00 | 0.00 | 0.00 | 4.40 | . |
| 4 | 4 | 99.24 | 0.13 | 0.30 | 0.00 | 0.00 | 0.00 | 0.00 | 0.00 | 0.63 | . |
| 5 | 5 | 95.27 | 0.00 | 0.42 | 0.00 | 0.00 | 0.00 | 0.00 | 0.00 | 4.73 | . |
| 6 | 6 | 99.69 | 0.00 | 1.10 | 0.00 | 0.00 | 0.00 | 0.00 | 0.00 | 0.31 | . |
| 7 | 7 | 99.79 | 0.00 | 1.12 | 0.00 | 0.00 | 0.00 | 0.00 | 0.00 | 0.21 | . |
| 8 | 8 | 96.22 | 0.95 | 2.39 | 0.10 | 0.00 | 0.00 | 0.00 | 0.00 | 2.83 | 24.29 |
| 9 | 9 | 92.71 | 2.22 | 5.53 | 0.00 | 0.00 | 0.00 | 0.00 | 0.00 | 5.07 | . |
| 10 | 10 | 92.04 | 1.33 | 4.13 | 0.00 | 0.00 | 0.00 | 0.00 | 0.00 | 6.62 | . |
| 11 | 11 | 91.42 | 1.48 | 4.52 | 0.00 | 0.00 | 0.00 | 0.00 | 0.00 | 7.10 | . |
| 12 | 12 | 94.09 | 2.82 | 2.77 | 0.00 | 0.00 | 0.00 | 0.00 | 0.00 | 3.10 | . |
| 13 | 13 | 95.80 | 1.52 | 2.68 | 0.00 | 0.00 | 0.00 | 0.00 | 0.00 | 2.68 | . |
| 14 | 14 | 95.94 | 1.45 | 3.66 | 0.00 | 0.00 | 0.00 | 0.00 | 0.00 | 2.61 | . |
| 15 | 15 | 91.64 | 1.38 | 4.27 | 0.00 | 0.00 | 0.00 | 0.00 | 0.00 | 6.98 | . |
| 16 | 16 | 87.11 | 3.25 | 8.44 | 0.43 | 0.09 | 0.00 | 0.14 | 0.00 | 9.65 | 20.40 |
| 17 | 17 | 86.75 | 3.35 | 8.73 | 0.44 | 0.10 | 0.00 | 0.15 | 0.00 | 9.90 | 20.38 |
| 18 | 18 | 90.27 | 1.81 | 5.10 | 0.00 | 0.00 | 0.00 | 0.00 | 0.00 | 7.92 | . |
| 19 | 19 | 86.82 | 3.40 | 9.54 | 0.63 | 0.00 | 0.00 | 0.00 | 0.00 | 9.79 | 15.08 |
| 20 | 20 | 87.84 | 2.38 | 6.79 | 0.45 | 0.00 | 0.00 | 0.00 | 0.00 | 9.78 | 15.00 |
| 21 | 21 | 83.83 | 3.33 | 9.80 | 0.65 | 0.00 | 0.00 | 0.25 | 0.00 | 12.84 | 15.51 |
| 22 | 22 | 87.04 | 3.96 | 10.22 | 0.00 | 0.00 | 0.00 | 0.00 | 0.00 | 9.00 | . |
| 23 | 23 | 84.47 | 3.48 | 10.79 | 0.68 | 0.11 | 0.05 | 0.15 | 0.00 | 12.05 | 15.22 |
| 24 | 24 | 81.91 | 3.91 | 12.38 | 0.77 | 0.17 | 0.09 | 0.25 | 0.00 | 14.18 | 14.92 |
| 25 | 25 | 42.53 | 10.12 | 38.30 | 1.93 | 2.02 | 0.96 | 2.91 | 0.08 | 47.35 | 14.57 |
| 26 | 26 | 44.14 | 9.91 | 37.44 | 1.91 | 1.86 | 0.91 | 2.72 | 0.08 | 45.95 | 14.51 |
| 27 | 27 | 41.66 | 10.19 | 38.88 | 1.96 | 2.07 | 0.99 | 3.02 | 0.08 | 48.15 | 14.51 |
| 28 | 28 | 70.77 | 5.85 | 19.62 | 1.43 | 0.00 | 0.00 | 0.65 | 0.00 | 23.38 | 14.14 |
| 29 | 29 | 67.77 | 6.29 | 22.05 | 1.53 | 0.00 | 0.00 | 0.70 | 0.00 | 25.95 | 14.85 |
| 30 | 30 | 46.53 | 9.00 | 36.93 | 2.17 | 0.00 | 1.06 | 2.77 | 0.00 | 44.47 | 12.26 |
| 31 | 31 | 42.64 | 9.56 | 39.78 | 2.26 | 0.00 | 1.21 | 3.20 | 0.00 | 47.80 | 12.38 |
| 32 | 32 | 44.94 | 9.02 | 37.57 | 2.21 | 0.00 | 1.14 | 2.96 | 0.00 | 46.04 | 12.12 |
| 33 | 33 | 41.81 | 9.58 | 40.18 | 2.32 | 0.00 | 1.25 | 3.20 | 0.00 | 48.61 | 12.17 |
| 34 | 34 | 60.21 | 7.47 | 25.88 | 1.50 | 0.00 | 1.16 | 4.30 | 0.44 | 32.32 | 9.76 |
| 35 | 35 | 31.96 | 9.09 | 44.42 | 2.19 | 3.55 | 1.94 | 5.90 | 0.32 | 58.95 | 12.12 |
| 36 | 36 | 34.88 | 8.71 | 42.30 | 2.14 | 3.22 | 1.79 | 5.46 | 0.30 | 56.41 | 12.05 |
| 37 | 37 | 75.59 | 4.60 | 16.80 | 1.13 | 0.41 | 0.28 | 0.74 | 0.02 | 19.80 | 12.50 |
| 38 | 38 | 76.39 | 4.52 | 16.42 | 1.12 | 0.35 | 0.25 | 0.60 | 0.00 | 19.09 | 12.70 |

TABLE 5-continued

ANILINE/PROPYLENE/ZEOLITES
Sorted by Temperature

| OBS | RUN | ANILINE MOLE PCT | N—IPA MOLE PCT | 2-IPA MOLE PCT | 4-IPA MOLE PCT | N,2-DIPA MOLE PCT | 2,4-DIPA MOLE PCT | 2,6-DIPA MOLE PCT | 2,4,6-TIPA MOLE PCT | CONV | O_P |
|---|---|---|---|---|---|---|---|---|---|---|---|
| 39 | 39 | 29.07 | 8.36 | 41.80 | 1.65 | 4.57 | 2.46 | 9.86 | 1.24 | 62.56 | 10.52 |
| 40 | 40 | 39.17 | 8.23 | 38.06 | 1.75 | 3.05 | 1.78 | 6.14 | 0.59 | 52.60 | 11.46 |
| 41 | 41 | 37.21 | 8.80 | 40.10 | 1.83 | 3.08 | 1.84 | 5.95 | 0.47 | 53.99 | 11.86 |
| 42 | 42 | 76.73 | 5.19 | 15.18 | 0.82 | 0.46 | 0.35 | 1.01 | 0.04 | 18.08 | 13.75 |
| 43 | 43 | 77.11 | 6.04 | 17.01 | 1.11 | 0.51 | 0.32 | 1.03 | 0.00 | 16.85 | 12.92 |
| 44 | 44 | 69.03 | 5.87 | 18.44 | 1.29 | 1.00 | 0.80 | 2.19 | 0.20 | 25.10 | 9.44 |
| 45 | 45 | 60.19 | 6.66 | 22.30 | 1.52 | 1.64 | 0.00 | 3.98 | 0.54 | 33.15 | 13.58 |
| 46 | 46 | 88.76 | 1.35 | 2.26 | 0.00 | 0.00 | 0.00 | 0.00 | 0.00 | 9.89 | . |
| 47 | 47 | 92.55 | 1.38 | 2.97 | 0.00 | 0.00 | 0.00 | 0.00 | 0.00 | 6.07 | . |
| 48 | 48 | 97.46 | 0.98 | 1.56 | 0.00 | 0.00 | 0.00 | 0.00 | 0.00 | 1.56 | . |
| 49 | 49 | 97.32 | 1.03 | 1.65 | 0.00 | 0.00 | 0.00 | 0.00 | 0.00 | 1.65 | . |
| 50 | 50 | 74.75 | 6.17 | 13.73 | 0.00 | 0.00 | 0.00 | 0.64 | 0.00 | 19.08 | . |
| 51 | 51 | 75.69 | 6.34 | 13.95 | 0.00 | 0.00 | 0.00 | 0.64 | 0.00 | 17.97 | . |
| 52 | 52 | 75.82 | 6.15 | 13.80 | 0.00 | 0.00 | 0.00 | 0.65 | 0.00 | 18.03 | . |
| 53 | 53 | 75.86 | 6.14 | 13.75 | 0.00 | 0.00 | 0.00 | 0.63 | 0.00 | 18.00 | . |
| 54 | 54 | 70.69 | 6.85 | 16.65 | 0.54 | 0.52 | 0.00 | 1.31 | 0.00 | 22.46 | 34.17 |
| 55 | 55 | 71.62 | 6.99 | 16.66 | 0.00 | 0.51 | 0.00 | 1.22 | 0.00 | 21.39 | . |
| 56 | 56 | 66.95 | 8.93 | 18.68 | 1.18 | 0.44 | 0.00 | 1.05 | 0.00 | 24.12 | 17.11 |
| 57 | 57 | 66.18 | 8.97 | 19.00 | 1.17 | 0.26 | 0.00 | 1.06 | 0.00 | 24.85 | 17.35 |
| 58 | 58 | 62.16 | 8.26 | 22.57 | 1.16 | 0.90 | 0.00 | 2.80 | 0.00 | 29.58 | 22.57 |
| 59 | 59 | 62.37 | 8.42 | 22.98 | 0.93 | 0.90 | 0.00 | 2.90 | 0.00 | 29.21 | 28.91 |
| 60 | 60 | 39.05 | 10.83 | 29.68 | 1.71 | 2.73 | 2.03 | 15.38 | 0.80 | 50.12 | 10.51 |
| 61 | 61 | 37.39 | 10.86 | 33.64 | 1.82 | 2.74 | 2.50 | 15.65 | 0.70 | 51.76 | 10.34 |
| 62 | 62 | 78.98 | 2.84 | 11.66 | 0.84 | 0.00 | 0.00 | 0.49 | 0.00 | 18.19 | 14.42 |
| 63 | 63 | 35.03 | 11.42 | 28.13 | 1.63 | 3.23 | 2.46 | 20.27 | 1.32 | 53.55 | 9.54 |
| 64 | 64 | 37.86 | 11.47 | 29.16 | 1.65 | 2.83 | 2.46 | 17.89 | 1.20 | 50.67 | 9.40 |
| 65 | 65 | 76.10 | 3.12 | 12.97 | 1.00 | 0.00 | 0.00 | 0.58 | 0.00 | 20.78 | 13.59 |
| 66 | 66 | 35.13 | 16.11 | 34.45 | 2.31 | 3.93 | 2.09 | 9.20 | 0.00 | 48.76 | 10.80 |
| 67 | 67 | 34.12 | 16.41 | 35.09 | 2.35 | 4.00 | 2.15 | 9.51 | 0.00 | 49.47 | 10.80 |
| 68 | 68 | 40.26 | 15.43 | 32.69 | 2.18 | 2.77 | 1.55 | 6.92 | 0.01 | 44.31 | 11.34 |
| 69 | 69 | 40.36 | 15.45 | 32.77 | 2.22 | 2.78 | 1.53 | 6.82 | 0.01 | 44.20 | 11.31 |
| 70 | 70 | 6.78 | 12.54 | 15.14 | 0.00 | 13.14 | 2.64 | 41.32 | 3.57 | 80.68 | 11.21 |
| 71 | 71 | 6.46 | 12.50 | 14.70 | 0.00 | 13.30 | 2.58 | 41.95 | 3.69 | 81.03 | 11.15 |
| 72 | 72 | 8.12 | 13.34 | 24.42 | 1.22 | 13.49 | 6.12 | 36.28 | 5.87 | 78.53 | 5.62 |
| 73 | 73 | 7.31 | 12.98 | 23.09 | 1.14 | 13.28 | 5.98 | 35.78 | 5.87 | 79.72 | 5.55 |
| 74 | 74 | 0.00 | 0.00 | 3.98 | 0.00 | 2.91 | 8.12 | 37.70 | 49.39 | 100.00 | 0.78 |
| 75 | 75 | 0.00 | 0.00 | 3.60 | 0.00 | 2.86 | 8.06 | 37.90 | 50.55 | 100.00 | 0.76 |

TABLE 6

ANILINE/PROPYLENE/ZEOLITES
Sorted by Pressure

| OBS | SAMPLE ID | RUN | TEMPERATURE | PRESSURE | N | R | CATALYST TYPE | LHSV | CONV | O_P |
|---|---|---|---|---|---|---|---|---|---|---|
| 1 | 7644-96-13 | 2 | 201 | 769 | 1.00 | 1.00 | H—MORDENITE | 0.13 | 0.61 | . |
| 2 | 7644-54-05 | 19 | 252 | 834 | 1.00 | 1.00 | H—MORDENITE | 0.13 | 9.79 | 15.08 |
| 3 | 7644-74-10 | 34 | 274 | 834 | 1.00 | 2.00 | H—MORDENITE | 0.06 | 32.32 | 9.76 |
| 4 | 7644-54-04 | 18 | 252 | 836 | 1.00 | 1.00 | H—MORDENITE | 0.13 | 7.92 | . |
| 5 | 7644-53-03 | 5 | 204 | 840 | 1.00 | 1.00 | H—MORDENITE | 0.13 | 4.73 | . |
| 6 | 7644-55-07 | 21 | 252 | 840 | 1.00 | 2.00 | H—MORDENITE | 0.13 | 12.84 | 15.51 |
| 7 | 7644-54-06 | 20 | 252 | 847 | 1.00 | 2.00 | H—MORDENITE | 0.13 | 9.78 | 15.00 |
| 8 | 7723-64-51 | 25 | 262 | 910 | 1.00 | 2.00 | H—MORDENITE | 0.03 | 47.35 | 14.57 |
| 9 | 7644-97-17 | 17 | 252 | 914 | 1.00 | 2.00 | H—MORDENITE | 0.13 | 9.90 | 20.38 |
| 10 | 7644-98-20 | 45 | 301 | 915 | 1.00 | 2.00 | H—MORDENITE | 0.06 | 33.15 | 13.58 |
| 11 | 7644-96-15 | 8 | 227 | 917 | 1.00 | 2.00 | H—MORDENITE | 0.13 | 2.83 | 24.29 |
| 12 | 7644-97-19 | 44 | 301 | 918 | 1.00 | 2.00 | H—MORDENITE | 0.13 | 25.10 | 9.44 |
| 13 | 7644-97-16 | 16 | 252 | 919 | 1.00 | 2.00 | H—MORDENITE | 0.13 | 9.65 | 20.40 |
| 14 | 7644-97-18 | 42 | 277 | 920 | 1.00 | 2.00 | H—MORDENITE | 0.13 | 18.08 | 13.75 |
| 15 | 7644-96-14 | 4 | 202 | 927 | 1.00 | 2.00 | H—MORDENITE | 0.13 | 0.63 | . |
| 16 | 7723-66-62 | 36 | 275 | 927 | 1.00 | 2.00 | H—MORDENITE | 0.03 | 56.41 | 12.05 |
| 17 | 7171-41-03 | 1 | 154 | 930 | 1.00 | 10.00 | H—MORDENITE | 0.25 | 2.46 | . |
| 18 | 7171-43-09 | 9 | 227 | 949 | 1.00 | 10.00 | H—MORDENITE | 0.25 | 5.07 | . |
| 19 | 7171-41-06 | 3 | 201 | 950 | 1.00 | 10.00 | H—MORDENITE | 0.25 | 4.40 | . |
| 20 | 7171-43-17 | 14 | 228 | 956 | 1.00 | 10.00 | H—MORDENITE | 0.25 | 2.61 | . |
| 21 | 7171-43-11 | 22 | 252 | 956 | 1.00 | 10.00 | H—MORDENITE | 0.25 | 9.00 | . |
| 22 | 7171-43-14 | 43 | 277 | 956 | 1.00 | 10.00 | H—MORDENITE | 0.25 | 16.85 | 12.92 |
| 23 | 7723-49-04 | 12 | 228 | 957 | 1.00 | 2.00 | H—MORDENITE | 0.13 | 3.10 | . |
| 24 | 7723-54-20 | 7 | 208 | 963 | 1.00 | 2.00 | H—MORDENITE | 0.13 | 0.21 | . |
| 25 | 7723-54-19 | 6 | 208 | 967 | 1.00 | 2.00 | H—MORDENITE | 0.13 | 0.31 | . |
| 26 | 7723-56-25 | 11 | 228 | 978 | 1.00 | 2.00 | H—MORDENITE | 0.13 | 7.10 | . |
| 27 | 7723-56-24 | 10 | 228 | 985 | 1.00 | 2.00 | H—MORDENITE | 0.13 | 6.62 | . |
| 28 | 7723-49-05 | 13 | 228 | 990 | 1.00 | 2.00 | H—MORDENITE | 0.13 | 2.68 | . |
| 29 | 7723-57-26 | 15 | 247 | 990 | 1.00 | 2.00 | H—MORDENITE | 0.13 | 6.98 | . |
| 30 | 7723-66-61 | 35 | 275 | 997 | 1.00 | 2.00 | H—MORDENITE | 0.03 | 58.95 | 12.12 |
| 31 | 7723-57-28 | 28 | 271 | 1000 | 1.00 | 2.00 | H—MORDENITE | 0.13 | 23.38 | 14.14 |

TABLE 6-continued

ANILINE/PROPYLENE/ZEOLITES
Sorted by Pressure

| OBS | SAMPLE ID | RUN | TEMPERATURE | PRESSURE | N | R | CATALYST TYPE | LHSV | CONV | O_P |
|---|---|---|---|---|---|---|---|---|---|---|
| 32 | 7723-58-34 | 30 | 271 | 1000 | 1.00 | 2.00 | H—MORDENITE | 0.13 | 44.47 | 12.26 |
| 33 | 7723-64-53 | 26 | 262 | 1000 | 1.00 | 2.00 | H—MORDENITE | 0.03 | 45.95 | 14.51 |
| 34 | 7723-59-38 | 33 | 271 | 1000 | 1.00 | 2.00 | H—MORDENITE | 0.13 | 48.61 | 12.17 |
| 35 | 7723-65-56 | 27 | 262 | 1002 | 1.00 | 2.00 | H—MORDENITE | 0.03 | 48.15 | 14.51 |
| 36 | 7723-59-37 | 32 | 271 | 1004 | 1.00 | 2.00 | H—MORDENITE | 0.13 | 46.04 | 12.12 |
| 37 | 7723-58-36 | 31 | 271 | 1004 | 1.00 | 2.00 | H—MORDENITE | 0.13 | 47.80 | 12.38 |
| 38 | 7723-57-30 | 29 | 271 | 1005 | 1.00 | 2.00 | H—MORDENITE | 0.13 | 25.95 | 14.85 |
| 39 | 7723-62-46 | 24 | 261 | 1006 | 1.00 | 2.00 | H—MORDENITE | 0.13 | 14.18 | 14.92 |
| 40 | 7723-62-45 | 23 | 261 | 1008 | 1.00 | 2.00 | H—MORDENITE | 0.13 | 12.05 | 15.22 |
| 41 | 7723-69-78 | 41 | 276 | 1011 | 1.00 | 10.00 | H—MORDENITE | 0.03 | 53.99 | 11.86 |
| 42 | 7723-68-74 | 39 | 276 | 1013 | 1.00 | 10.00 | H—MORDENITE | 0.03 | 62.56 | 10.52 |
| 43 | 7723-69-77 | 40 | 276 | 1015 | 1.00 | 10.00 | H—MORDENITE | 0.03 | 52.60 | 11.46 |
| 44 | 7723-67-69 | 38 | 276 | 1020 | 1.00 | 10.00 | H—MORDENITE | 0.12 | 19.09 | 12.70 |
| 45 | 7723-67-67 | 37 | 276 | 1020 | 1.00 | 10.00 | H—MORDENITE | 0.12 | 19.80 | 12.50 |
| 46 | 7432-09-06 | 47 | 150 | 883 | 1.00 | 1.00 | H—Y | 0.13 | 6.07 | . |
| 47 | 7432-08-05 | 46 | 150 | 883 | 1.00 | 1.00 | H—Y | 0.13 | 9.89 | . |
| 48 | 7432-09-07 | 58 | 203 | 907 | 1.00 | 10.00 | H—Y | 0.25 | 29.58 | 22.57 |
| 49 | 7432-11-12 | 51 | 167 | 910 | 1.00 | 2.00 | H—Y | 0.06 | 17.97 | . |
| 50 | 7432-11-11 | 50 | 167 | 910 | 1.00 | 2.00 | H—Y | 0.06 | 19.08 | . |
| 51 | 7432-09-08 | 59 | 203 | 910 | 1.00 | 10.00 | H—Y | 0.25 | 29.21 | 28.91 |
| 52 | 7432-12-13 | 53 | 167 | 911 | 1.00 | 1.00 | H—Y | 0.06 | 18.00 | . |
| 53 | 7432-10-09 | 64 | 182 | 911 | 1.00 | 2.00 | H—Y | 0.13 | 22.46 | 34.17 |
| 54 | 7432-12-12 | 52 | 167 | 913 | 1.00 | 1.00 | H—Y | 0.06 | 18.03 | . |
| 55 | 7171-40-18 | 69 | 228 | 913 | 1.00 | 10.00 | H—Y | 0.25 | 44.20 | 11.31 |
| 56 | 7171-40-17 | 68 | 228 | 913 | 1.00 | 10.00 | H—Y | 0.25 | 44.31 | 11.34 |
| 57 | 7432-10-10 | 55 | 182 | 918 | 1.00 | 2.00 | H—Y | 0.13 | 21.39 | . |
| 58 | 7432-15-19 | 60 | 226 | 918 | 2.00 | 1.00 | H—Y | 0.06 | 50.12 | 10.51 |
| 59 | 7432-15-20 | 61 | 226 | 918 | 2.00 | 1.00 | H—Y | 0.06 | 51.76 | 10.34 |
| 60 | 7432-23-22 | 62 | 226 | 928 | 4.00 | 1.00 | H—Y | 0.06 | 18.19 | 14.42 |
| 61 | 7432-14-16 | 63 | 227 | 928 | 1.00 | 1.00 | H—Y | 0.06 | 53.55 | 9.54 |
| 62 | 7432-14-18 | 64 | 227 | 930 | 1.00 | 1.00 | H—Y | 0.06 | 50.67 | 9.40 |
| 63 | 7432-23-23 | 65 | 227 | 931 | 4.00 | 1.00 | H—Y | 0.06 | 20.78 | 13.59 |
| 64 | 7171-37-02 | 48 | 154 | 960 | 1.00 | 11.80 | H—Y | 0.25 | 1.56 | . |
| 65 | 7171-37-03 | 49 | 154 | 962 | 1.00 | 10.00 | H—Y | 0.25 | 1.65 | . |
| 66 | 7171-38-05 | 56 | 202 | 972 | 1.00 | 10.00 | H—Y | 0.25 | 24.12 | 17.11 |
| 67 | 7171-28-16 | 57 | 202 | 972 | 1.00 | 10.00 | H—Y | 0.25 | 24.85 | 17.35 |
| 68 | 7171-39-09 | 67 | 228 | 985 | 1.00 | 10.00 | H—Y | 0.25 | 49.47 | 10.80 |
| 69 | 7171-39-14 | 74 | 277 | 985 | 1.00 | 10.00 | H—Y | 0.25 | 100.00 | 0.78 |
| 70 | 7171-39-15 | 75 | 277 | 986 | 1.00 | 10.00 | H—Y | 0.25 | 100.00 | 0.76 |
| 71 | 7171-39-11 | 72 | 253 | 988 | 1.00 | 10.00 | H—Y | 0.25 | 78.53 | 5.62 |
| 72 | 7171-39-12 | 73 | 253 | 988 | 1.00 | 10.00 | H—Y | 0.25 | 79.72 | 5.55 |
| 73 | 7171-38-18 | 66 | 228 | 990 | 1.00 | 10.00 | H—Y | 0.25 | 48.76 | 10.80 |
| 74 | 7723-19-33 | 70 | 228 | 1021 | 1.00 | 10.00 | H—Y | 0.06 | 80.68 | 11.21 |
| 75 | 7723-19-34 | 71 | 228 | 1024 | 1.00 | 10.00 | H—Y | 0.06 | 81.03 | 11.15 |

TABLE 7

ANILINE/PROPYLENE/ZEOLITES
Sorted by Pressure

| OBS | RUN | ANILINE MOLE PCT | N—IPA MOLE PCT | 2-IPA MOLE PCT | 4-IPA MOLE PCT | N,2-DIPA MOLE PCT | 2,4-DIPA MOLE PCT | 2,6-DIPA MOLE PCT | 2,4-TIPA MOLE PCT | CONV | O_P |
|---|---|---|---|---|---|---|---|---|---|---|---|
| 1 | 2 | 99.39 | 0.00 | 0.13 | 0.00 | 0.00 | 0.00 | 0.00 | 0.00 | 0.61 | . |
| 2 | 19 | 86.82 | 3.40 | 9.54 | 0.63 | 0.00 | 0.00 | 0.00 | 0.00 | 9.79 | 15.08 |
| 3 | 34 | 60.21 | 7.47 | 25.88 | 1.50 | 0.00 | 1.16 | 4.30 | 0.44 | 32.32 | 9.76 |
| 4 | 18 | 90.27 | 1.81 | 5.10 | 0.00 | 0.00 | 0.00 | 0.00 | 0.00 | 7.92 | . |
| 5 | 5 | 95.27 | 0.00 | 0.42 | 0.00 | 0.00 | 0.00 | 0.00 | 0.00 | 4.73 | . |
| 6 | 21 | 83.83 | 3.33 | 9.80 | 0.65 | 0.00 | 0.00 | 0.25 | 0.00 | 12.84 | 15.51 |
| 7 | 20 | 87.84 | 2.38 | 6.79 | 0.45 | 0.00 | 0.00 | 0.00 | 0.00 | 9.78 | 15.00 |
| 8 | 25 | 42.53 | 10.12 | 38.30 | 1.93 | 2.02 | 0.96 | 2.91 | 0.08 | 47.35 | 14.57 |
| 9 | 17 | 86.75 | 3.35 | 8.73 | 0.44 | 0.10 | 0.00 | 0.15 | 0.00 | 9.90 | 20.38 |
| 10 | 45 | 60.19 | 6.66 | 22.30 | 1.52 | 1.64 | 0.00 | 3.98 | 0.54 | 33.15 | 13.58 |
| 11 | 8 | 96.22 | 0.95 | 2.39 | 0.10 | 0.00 | 0.00 | 0.00 | 0.00 | 2.83 | 24.29 |
| 12 | 44 | 69.03 | 5.87 | 18.44 | 1.29 | 1.00 | 0.80 | 2.19 | 0.20 | 25.10 | 9.44 |
| 13 | 16 | 87.11 | 3.25 | 8.44 | 0.43 | 0.09 | 0.00 | 0.14 | 0.00 | 9.65 | 20.40 |
| 14 | 42 | 76.73 | 5.19 | 15.18 | 0.82 | 0.46 | 0.35 | 1.01 | 0.04 | 18.08 | 13.75 |
| 15 | 4 | 99.24 | 0.13 | 0.30 | 0.00 | 0.00 | 0.00 | 0.00 | 0.00 | 0.63 | . |
| 16 | 36 | 34.88 | 8.71 | 42.30 | 2.14 | 3.22 | 1.79 | 5.46 | 0.30 | 56.41 | 12.05 |
| 17 | 1 | 96.65 | 0.88 | 1.45 | 0.00 | 0.00 | 0.00 | 0.00 | 0.00 | 2.46 | . |
| 18 | 9 | 92.71 | 2.22 | 5.53 | 0.00 | 0.00 | 0.00 | 0.00 | 0.00 | 5.07 | . |
| 19 | 3 | 94.37 | 1.23 | 2.77 | 0.00 | 0.00 | 0.00 | 0.00 | 0.00 | 4.40 | . |
| 20 | 14 | 95.94 | 1.45 | 3.66 | 0.00 | 0.00 | 0.00 | 0.00 | 0.00 | 2.61 | . |
| 21 | 22 | 87.04 | 3.96 | 10.22 | 0.00 | 0.00 | 0.00 | 0.00 | 0.00 | 9.00 | . |
| 22 | 43 | 77.11 | 6.04 | 17.01 | 1.11 | 0.51 | 0.32 | 1.03 | 0.00 | 16.85 | 12.92 |
| 23 | 12 | 94.09 | 2.82 | 2.77 | 0.00 | 0.00 | 0.00 | 0.00 | 0.00 | 3.10 | . |
| 24 | 7 | 99.79 | 0.00 | 1.12 | 0.00 | 0.00 | 0.00 | 0.00 | 0.00 | 0.21 | . |

TABLE 7-continued
ANILINE/PROPYLENE/ZEOLITES
Sorted by Pressure

| OBS | RUN | ANILINE MOLE PCT | N—IPA MOLE PCT | 2-IPA MOLE PCT | 4-IPA MOLE PCT | N,2-DIPA MOLE PCT | 2,4-DIPA MOLE PCT | 2,6-DIPA MOLE PCT | 2,4-TIPA MOLE PCT | CONV | O_P |
|---|---|---|---|---|---|---|---|---|---|---|---|
| 25 | 6 | 99.69 | 0.00 | 1.10 | 0.00 | 0.00 | 0.00 | 0.00 | 0.00 | 0.31 | . |
| 26 | 11 | 91.42 | 1.48 | 4.52 | 0.00 | 0.00 | 0.00 | 0.00 | 0.00 | 7.10 | . |
| 27 | 10 | 97.04 | 1.33 | 4.13 | 0.00 | 0.00 | 0.00 | 0.00 | 0.00 | 6.62 | . |
| 28 | 13 | 95.80 | 1.52 | 2.68 | 0.00 | 0.00 | 0.00 | 0.00 | 0.00 | 2.68 | . |
| 29 | 15 | 91.64 | 1.38 | 4.27 | 0.00 | 0.00 | 0.00 | 0.00 | 0.00 | 6.98 | . |
| 30 | 35 | 31.96 | 9.09 | 44.42 | 2.19 | 3.55 | 1.94 | 5.90 | 0.32 | 58.95 | 12.12 |
| 31 | 28 | 70.77 | 5.85 | 19.62 | 1.43 | 0.00 | 0.00 | 0.65 | 0.00 | 23.38 | 14.14 |
| 32 | 30 | 46.53 | 9.00 | 36.93 | 2.17 | 0.00 | 1.06 | 2.77 | 0.00 | 44.47 | 12.26 |
| 33 | 26 | 44.14 | 9.91 | 37.44 | 1.91 | 1.86 | 0.91 | 2.72 | 0.08 | 45.95 | 14.51 |
| 34 | 33 | 41.81 | 9.58 | 40.18 | 2.32 | 0.00 | 1.25 | 3.20 | 0.00 | 48.61 | 12.17 |
| 35 | 27 | 41.66 | 10.19 | 38.88 | 1.96 | 2.07 | 0.99 | 3.02 | 0.08 | 48.15 | 14.51 |
| 36 | 32 | 44.94 | 9.02 | 37.57 | 2.21 | 0.00 | 1.14 | 2.96 | 0.00 | 46.04 | 12.12 |
| 37 | 31 | 42.64 | 9.56 | 39.78 | 2.26 | 0.00 | 1.21 | 3.20 | 0.00 | 47.80 | 12.38 |
| 38 | 29 | 67.77 | 6.29 | 22.05 | 1.53 | 0.00 | 0.00 | 0.70 | 0.00 | 25.95 | 14.85 |
| 39 | 24 | 81.91 | 3.91 | 12.38 | 0.77 | 0.17 | 0.09 | 0.25 | 0.00 | 14.18 | 14.92 |
| 40 | 23 | 84.47 | 3.48 | 10.79 | 0.68 | 0.11 | 0.05 | 0.15 | 0.00 | 12.05 | 15.22 |
| 41 | 41 | 37.21 | 8.80 | 40.10 | 1.83 | 3.08 | 1.84 | 5.95 | 0.47 | 53.99 | 11.86 |
| 42 | 39 | 29.07 | 8.36 | 41.80 | 1.65 | 4.57 | 2.46 | 9.86 | 1.24 | 62.56 | 10.52 |
| 43 | 40 | 39.17 | 8.23 | 38.06 | 1.75 | 3.05 | 1.78 | 6.14 | 0.59 | 52.60 | 11.46 |
| 44 | 38 | 76.39 | 4.52 | 16.42 | 1.12 | 0.35 | 0.25 | 0.60 | 0.00 | 19.09 | 12.70 |
| 45 | 37 | 75.59 | 4.60 | 16.80 | 1.13 | 0.41 | 0.28 | 0.74 | 0.02 | 19.80 | 12.50 |
| 46 | 47 | 92.55 | 1.38 | 2.97 | 0.00 | 0.00 | 0.00 | 0.00 | 0.00 | 6.07 | . |
| 47 | 46 | 88.76 | 1.35 | 2.26 | 0.00 | 0.00 | 0.00 | 0.00 | 0.00 | 9.89 | . |
| 48 | 58 | 62.16 | 8.26 | 22.57 | 1.16 | 0.90 | 0.00 | 2.80 | 0.00 | 29.58 | 22.57 |
| 49 | 51 | 75.69 | 6.34 | 13.95 | 0.00 | 0.00 | 0.00 | 0.64 | 0.00 | 17.97 | . |
| 50 | 50 | 74.75 | 6.17 | 13.73 | 0.00 | 0.00 | 0.00 | 0.64 | 0.00 | 19.08 | . |
| 51 | 59 | 62.37 | 8.42 | 22.98 | 0.93 | 0.90 | 0.00 | 2.90 | 0.00 | 29.21 | 28.91 |
| 52 | 53 | 75.86 | 6.14 | 13.75 | 0.00 | 0.00 | 0.00 | 0.63 | 0.00 | 18.00 | . |
| 53 | 54 | 70.69 | 6.85 | 16.65 | 0.54 | 0.52 | 0.00 | 1.31 | 0.00 | 22.46 | 34.17 |
| 54 | 52 | 75.82 | 6.15 | 13.80 | 0.00 | 0.00 | 0.00 | 0.65 | 0.00 | 18.03 | . |
| 55 | 69 | 40.36 | 15.45 | 32.77 | 2.22 | 2.78 | 1.53 | 6.82 | 0.01 | 44.20 | 11.31 |
| 56 | 68 | 40.26 | 15.43 | 32.69 | 2.18 | 2.77 | 1.55 | 6.92 | 0.01 | 44.31 | 11.34 |
| 57 | 55 | 71.62 | 6.99 | 16.66 | 0.00 | 0.51 | 0.00 | 1.22 | 0.00 | 21.39 | . |
| 58 | 60 | 39.05 | 10.83 | 29.68 | 1.71 | 2.73 | 2.03 | 15.38 | 0.80 | 50.12 | 10.51 |
| 59 | 61 | 37.39 | 10.86 | 33.64 | 1.82 | 2.74 | 2.50 | 15.65 | 0.70 | 51.76 | 10.34 |
| 60 | 62 | 78.98 | 2.84 | 11.66 | 0.84 | 0.00 | 0.00 | 0.49 | 0.00 | 18.19 | 14.42 |
| 61 | 63 | 35.03 | 11.42 | 28.13 | 1.63 | 3.23 | 2.46 | 20.27 | 1.32 | 53.55 | 9.54 |
| 62 | 64 | 37.86 | 11.47 | 29.16 | 1.65 | 2.83 | 2.46 | 17.89 | 1.20 | 50.67 | 9.40 |
| 63 | 65 | 76.10 | 3.12 | 12.97 | 1.00 | 0.00 | 0.00 | 0.58 | 0.00 | 20.78 | 13.59 |
| 64 | 48 | 97.46 | 0.98 | 1.56 | 0.00 | 0.00 | 0.00 | 0.00 | 0.00 | 1.56 | . |
| 65 | 49 | 97.32 | 1.03 | 1.65 | 0.00 | 0.00 | 0.00 | 0.00 | 0.00 | 1.65 | . |
| 66 | 56 | 66.95 | 8.93 | 18.68 | 1.18 | 0.44 | 0.00 | 1.05 | 0.00 | 24.12 | 17.11 |
| 67 | 57 | 66.18 | 8.97 | 19.00 | 1.17 | 0.26 | 0.00 | 1.06 | 0.00 | 24.85 | 17.35 |
| 68 | 67 | 34.12 | 16.41 | 35.09 | 2.35 | 4.00 | 2.15 | 9.51 | 0.00 | 49.47 | 10.80 |
| 69 | 74 | 0.00 | 0.00 | 3.98 | 0.00 | 2.91 | 8.12 | 37.70 | 49.39 | 100.00 | 0.78 |
| 70 | 75 | 0.00 | 0.00 | 3.60 | 0.00 | 2.86 | 8.06 | 37.90 | 50.55 | 100.00 | 0.76 |
| 71 | 72 | 8.12 | 13.34 | 24.42 | 1.22 | 13.49 | 6.12 | 36.28 | 5.87 | 78.53 | 5.62 |
| 72 | 73 | 7.31 | 12.98 | 23.09 | 1.14 | 13.28 | 5.98 | 35.78 | 5.87 | 79.72 | 5.55 |
| 73 | 66 | 35.13 | 16.11 | 34.45 | 2.31 | 3.93 | 2.09 | 9.20 | 0.00 | 48.76 | 10.80 |
| 74 | 70 | 6.78 | 12.54 | 15.14 | 0.00 | 13.14 | 2.64 | 41.32 | 3.57 | 80.68 | 11.21 |
| 75 | 71 | 6.46 | 12.50 | 14.70 | 0.00 | 13.30 | 2.58 | 41.95 | 3.69 | 81.03 | 11.15 |

TABLE 8
ANILINE/PROPYLENE/ZEOLITES
Sorted by Conversion

| OBS | SAMPLE ID | RUN | TEMPERATURE | PRESSURE | N | R | CATALYST TYPE | LHSV | CONV | O_P |
|---|---|---|---|---|---|---|---|---|---|---|
| 1 | 7723-54-20 | 7 | 208 | 963 | 1.00 | 2.00 | H—MORDENITE | 0.13 | 0.21 | . |
| 2 | 7723-54-19 | 6 | 208 | 967 | 1.00 | 2.00 | H—MORDENITE | 0.13 | 0.31 | . |
| 3 | 7644-96-13 | 2 | 201 | 769 | 1.00 | 1.00 | H—MORDENITE | 0.13 | 0.61 | . |
| 4 | 7644-96-14 | 4 | 202 | 927 | 1.00 | 2.00 | H—MORDENITE | 0.13 | 0.63 | . |
| 5 | 7171-41-03 | 1 | 154 | 930 | 1.00 | 10.00 | H—MORDENITE | 0.25 | 2.46 | . |
| 6 | 7171-43-17 | 14 | 228 | 956 | 1.00 | 10.00 | H—MORDENITE | 0.25 | 2.61 | . |
| 7 | 7723-49-05 | 13 | 228 | 990 | 1.00 | 2.00 | H—MORDENITE | 0.13 | 2.68 | . |
| 8 | 7644-96-15 | 8 | 227 | 917 | 1.00 | 2.00 | H—MORDENITE | 0.13 | 2.83 | 24.29 |
| 9 | 7723-49-04 | 12 | 228 | 957 | 1.00 | 2.00 | H—MORDENITE | 0.13 | 3.10 | . |
| 10 | 7171-41-06 | 3 | 201 | 950 | 1.00 | 10.00 | H—MORDENITE | 0.25 | 4.40 | . |
| 11 | 7644-53-03 | 5 | 204 | 840 | 1.00 | 1.00 | H—MORDENITE | 0.13 | 4.73 | . |
| 12 | 7171-43-09 | 9 | 227 | 949 | 1.00 | 10.00 | H—MORDENITE | 0.25 | 5.07 | . |
| 13 | 7723-56-24 | 10 | 228 | 985 | 1.00 | 2.00 | H—MORDENITE | 0.13 | 6.62 | . |
| 14 | 7723-57-26 | 15 | 247 | 990 | 1.00 | 2.00 | H—MORDENITE | 0.13 | 6.98 | . |
| 15 | 7723-56-25 | 11 | 228 | 978 | 1.00 | 2.00 | H—MORDENITE | 0.13 | 7.10 | . |
| 16 | 7644-54-04 | 18 | 252 | 836 | 1.00 | 1.00 | H—MORDENITE | 0.13 | 7.92 | . |
| 17 | 7171-43-11 | 22 | 252 | 956 | 1.00 | 10.00 | H—MORDENITE | 0.25 | 9.00 | . |

TABLE 8-continued

ANILINE/PROPYLENE/ZEOLITES
Sorted by Conversion

| OBS | SAMPLE ID | RUN | TEMPERATURE | PRESSURE | N | R | CATALYST TYPE | LHSV | CONV | O_P |
|---|---|---|---|---|---|---|---|---|---|---|
| 18 | 7644-97-16 | 16 | 252 | 919 | 1.00 | 2.00 | H—MORDENITE | 0.13 | 9.65 | 20.40 |
| 19 | 7644-54-06 | 20 | 252 | 847 | 1.00 | 2.00 | H—MORDENITE | 0.13 | 9.78 | 15.00 |
| 20 | 7644-54-05 | 19 | 252 | 834 | 1.00 | 1.00 | H—MORDENITE | 0.13 | 9.79 | 15.08 |
| 21 | 7644-97-17 | 17 | 252 | 914 | 1.00 | 2.00 | H—MORDENITE | 0.13 | 9.90 | 20.38 |
| 22 | 7723-62-45 | 23 | 261 | 1008 | 1.00 | 2.00 | H—MORDENITE | 0.13 | 12.05 | 15.22 |
| 23 | 7644-55-07 | 21 | 252 | 840 | 1.00 | 2.00 | H—MORDENITE | 0.13 | 12.84 | 15.51 |
| 24 | 7723-62-46 | 24 | 261 | 1006 | 1.00 | 2.00 | H—MORDENITE | 0.13 | 14.18 | 14.92 |
| 25 | 7171-43-14 | 43 | 277 | 956 | 1.00 | 10.00 | H—MORDENITE | 0.25 | 16.85 | 12.92 |
| 26 | 7644-97-18 | 42 | 277 | 920 | 1.00 | 2.00 | H—MORDENITE | 0.13 | 18.08 | 13.75 |
| 27 | 7723-67-69 | 38 | 276 | 1020 | 1.00 | 10.00 | H—MORDENITE | 0.12 | 19.09 | 12.70 |
| 28 | 7723-67-67 | 37 | 276 | 1020 | 1.00 | 10.00 | H—MORDENITE | 0.12 | 19.80 | 12.50 |
| 29 | 7723-57-28 | 28 | 271 | 1000 | 1.00 | 2.00 | H—MORDENITE | 0.13 | 23.38 | 14.14 |
| 30 | 7644-97-19 | 44 | 301 | 918 | 1.00 | 2.00 | H—MORDENITE | 0.13 | 25.10 | 9.44 |
| 31 | 7723-57-30 | 29 | 271 | 1005 | 1.00 | 2.00 | H—MORDENITE | 0.13 | 25.95 | 14.85 |
| 32 | 7644-74-10 | 34 | 274 | 834 | 1.00 | 2.00 | H—MORDENITE | 0.06 | 32.32 | 9.76 |
| 33 | 7644-98-20 | 45 | 301 | 915 | 1.00 | 2.00 | H—MORDENITE | 0.06 | 33.15 | 13.58 |
| 34 | 7723-58-34 | 30 | 271 | 1000 | 1.00 | 2.00 | H—MORDENITE | 0.13 | 44.47 | 12.26 |
| 35 | 7723-64-53 | 26 | 262 | 1000 | 1.00 | 2.00 | H—MORDENITE | 0.03 | 45.95 | 14.51 |
| 36 | 7723-59-37 | 32 | 271 | 1004 | 1.00 | 2.00 | H—MORDENITE | 0.13 | 46.04 | 12.12 |
| 37 | 7723-64-51 | 25 | 262 | 910 | 1.00 | 2.00 | H—MORDENITE | 0.03 | 47.35 | 14.57 |
| 38 | 7723-58-36 | 31 | 271 | 1004 | 1.00 | 2.00 | H—MORDENITE | 0.13 | 47.80 | 12.38 |
| 39 | 7723-65-56 | 27 | 262 | 1002 | 1.00 | 2.00 | H—MORDENITE | 0.03 | 48.15 | 14.51 |
| 40 | 7723-59-38 | 33 | 271 | 1000 | 1.00 | 2.00 | H—MORDENITE | 0.13 | 48.61 | 12.17 |
| 41 | 7723-69-77 | 40 | 276 | 1015 | 1.00 | 10.00 | H—MORDENITE | 0.03 | 52.60 | 11.46 |
| 42 | 7723-69-78 | 41 | 276 | 1011 | 1.00 | 10.00 | H—MORDENITE | 0.03 | 53.99 | 11.86 |
| 43 | 7723-66-62 | 36 | 275 | 927 | 1.00 | 2.00 | H—MORDENITE | 0.03 | 56.41 | 12.05 |
| 44 | 7723-66-61 | 35 | 275 | 997 | 1.00 | 2.00 | H—MORDENITE | 0.03 | 58.95 | 12.12 |
| 45 | 7723-68-74 | 39 | 276 | 1013 | 1.00 | 10.00 | H—MORDENITE | 0.03 | 62.56 | 10.52 |
| 46 | 7171-37-02 | 48 | 154 | 960 | 1.00 | 11.80 | H—Y | 0.25 | 1.56 | . |
| 47 | 7171-37-03 | 49 | 154 | 962 | 1.00 | 10.00 | H—Y | 0.25 | 1.65 | . |
| 48 | 7432-09-06 | 47 | 150 | 883 | 1.00 | 1.00 | H—Y | 0.13 | 6.07 | . |
| 49 | 7432-08-05 | 46 | 150 | 883 | 1.00 | 1.00 | H—Y | 0.13 | 9.89 | . |
| 50 | 7432-11-12 | 51 | 167 | 910 | 1.00 | 2.00 | H—Y | 0.06 | 17.97 | . |
| 51 | 7432-12-13 | 53 | 167 | 911 | 1.00 | 1.00 | H—Y | 0.06 | 18.00 | . |
| 52 | 7432-12-12 | 52 | 167 | 913 | 1.00 | 1.00 | H—Y | 0.06 | 18.03 | . |
| 53 | 7432-23-22 | 62 | 226 | 928 | 4.00 | 1.00 | H—Y | 0.06 | 18.19 | 14.42 |
| 54 | 7432-11-11 | 50 | 167 | 910 | 1.00 | 2.00 | H—Y | 0.06 | 19.08 | . |
| 55 | 7432-23-23 | 65 | 227 | 931 | 4.00 | 1.00 | H—Y | 0.06 | 20.78 | 13.59 |
| 56 | 7432-10-10 | 55 | 182 | 918 | 1.00 | 2.00 | H—Y | 0.13 | 21.39 | . |
| 57 | 7432-10-09 | 54 | 182 | 911 | 1.00 | 2.00 | H—Y | 0.13 | 22.46 | 34.17 |
| 58 | 7171-38-05 | 56 | 202 | 972 | 1.00 | 10.00 | H—Y | 0.25 | 24.12 | 17.11 |
| 59 | 7171-38-16 | 57 | 202 | 972 | 1.00 | 10.00 | H—Y | 0.25 | 24.85 | 17.35 |
| 60 | 7432-09-08 | 59 | 203 | 910 | 1.00 | 10.00 | H—Y | 0.25 | 29.21 | 28.91 |
| 61 | 7432-09-07 | 58 | 203 | 907 | 1.00 | 10.00 | H—Y | 0.25 | 29.58 | 22.57 |
| 62 | 7171-40-18 | 69 | 228 | 913 | 1.00 | 10.00 | H—Y | 0.25 | 44.20 | 11.31 |
| 63 | 7171-40-17 | 68 | 228 | 913 | 1.00 | 10.00 | H—Y | 0.25 | 44.31 | 11.34 |
| 64 | 7171-38-18 | 66 | 228 | 990 | 1.00 | 10.00 | H—Y | 0.25 | 48.76 | 10.80 |
| 65 | 7171-39-09 | 67 | 228 | 985 | 1.00 | 10.00 | H—Y | 0.25 | 49.47 | 10.80 |
| 66 | 7432-15-19 | 60 | 226 | 918 | 2.00 | 1.00 | H—Y | 0.06 | 50.12 | 10.51 |
| 67 | 7432-14-18 | 64 | 227 | 930 | 1.00 | 1.00 | H—Y | 0.06 | 50.67 | 9.40 |
| 68 | 7432-15-20 | 61 | 226 | 918 | 2.00 | 1.00 | H—Y | 0.06 | 51.76 | 10.34 |
| 69 | 7432-14-16 | 63 | 227 | 928 | 1.00 | 1.00 | H—Y | 0.06 | 53.55 | 9.54 |
| 70 | 7171-39-11 | 72 | 253 | 988 | 1.00 | 10.00 | H—Y | 0.25 | 78.53 | 5.62 |
| 71 | 7171-39-12 | 73 | 253 | 988 | 1.00 | 10.00 | H—Y | 0.25 | 79.72 | 5.55 |
| 72 | 7723-19-33 | 70 | 228 | 1021 | 1.00 | 10.00 | H—Y | 0.06 | 80.68 | 11.21 |
| 73 | 7723-19-34 | 71 | 228 | 1024 | 1.00 | 10.00 | H—Y | 0.06 | 81.03 | 11.15 |
| 74 | 7171-39-15 | 75 | 277 | 986 | 1.00 | 10.00 | H—Y | 0.25 | 100.00 | 0.76 |
| 75 | 7171-39-14 | 74 | 277 | 985 | 1.00 | 10.00 | H—Y | 0.25 | 100.00 | 0.78 |

TABLE 9

ANILINE/PROPYLENE/ZEOLITES
Sorted by Conversion

| OBS | RUN | ANILINE MOLE PCT | N—IPA MOLE PCT | 2-IPA MOLE PCT | 4-IPA MOLE PCT | N,2-DIPA MOLE PCT | 2,4-DIPA MOLE PCT | 2,6-DIPA MOLE PCT | 2,4,6-TIPA MOLE PCT | CONV | O_P |
|---|---|---|---|---|---|---|---|---|---|---|---|
| 1 | 7 | 99.79 | 0.00 | 1.12 | 0.00 | 0.00 | 0.00 | 0.00 | 0.00 | 0.21 | . |
| 2 | 6 | 99.69 | 0.00 | 1.10 | 0.00 | 0.00 | 0.00 | 0.00 | 0.00 | 0.31 | . |
| 3 | 2 | 99.39 | 0.00 | 0.13 | 0.00 | 0.00 | 0.00 | 0.00 | 0.00 | 0.61 | . |
| 4 | 4 | 99.24 | 0.13 | 0.30 | 0.00 | 0.00 | 0.00 | 0.00 | 0.00 | 0.63 | . |
| 5 | 1 | 96.65 | 0.88 | 1.45 | 0.00 | 0.00 | 0.00 | 0.00 | 0.00 | 2.46 | . |
| 6 | 14 | 95.94 | 1.45 | 3.66 | 0.00 | 0.00 | 0.00 | 0.00 | 0.00 | 2.61 | . |
| 7 | 13 | 95.80 | 1.52 | 2.68 | 0.00 | 0.00 | 0.00 | 0.00 | 0.00 | 2.68 | . |
| 8 | 8 | 96.22 | 0.95 | 2.39 | 0.10 | 0.00 | 0.00 | 0.00 | 0.00 | 2.83 | 24.29 |
| 9 | 12 | 94.09 | 2.82 | 2.77 | 0.00 | 0.00 | 0.00 | 0.00 | 0.00 | 3.10 | . |
| 10 | 3 | 94.37 | 1.23 | 2.77 | 0.00 | 0.00 | 0.00 | 0.00 | 0.00 | 4.40 | . |
| 11 | 5 | 95.27 | 0.00 | 0.42 | 0.00 | 0.00 | 0.00 | 0.00 | 0.00 | 4.73 | . |

TABLE 9-continued

ANILINE/PROPYLENE/ZEOLITES
Sorted by Conversion

| OBS | RUN | ANILINE MOLE PCT | N—IPA MOLE PCT | 2-IPA MOLE PCT | 4-IPA MOLE PCT | N,2-DIPA MOLE PCT | 2,4-DIPA MOLE PCT | 2,6-DIPA MOLE PCT | 2,4,6-TIPA MOLE PCT | CONV | O_P |
|---|---|---|---|---|---|---|---|---|---|---|---|
| 12 | 9  | 92.71 | 2.22  | 5.53  | 0.00 | 0.00  | 0.00 | 0.00  | 0.00 | 5.07  | . |
| 13 | 10 | 92.04 | 1.33  | 4.13  | 0.00 | 0.00  | 0.00 | 0.00  | 0.00 | 6.62  | . |
| 14 | 15 | 91.64 | 1.38  | 4.27  | 0.00 | 0.00  | 0.00 | 0.00  | 0.00 | 6.98  | . |
| 15 | 11 | 91.42 | 1.48  | 4.52  | 0.00 | 0.00  | 0.00 | 0.00  | 0.00 | 7.10  | . |
| 16 | 18 | 90.27 | 1.81  | 5.10  | 0.00 | 0.00  | 0.00 | 0.00  | 0.00 | 7.92  | . |
| 17 | 22 | 87.04 | 3.96  | 10.22 | 0.00 | 0.00  | 0.00 | 0.00  | 0.00 | 9.00  | . |
| 18 | 16 | 87.11 | 3.25  | 8.44  | 0.43 | 0.09  | 0.00 | 0.14  | 0.00 | 9.65  | 20.40 |
| 19 | 20 | 87.84 | 2.38  | 6.79  | 0.45 | 0.00  | 0.00 | 0.00  | 0.00 | 9.78  | 15.00 |
| 20 | 19 | 86.82 | 3.40  | 9.54  | 0.63 | 0.00  | 0.00 | 0.00  | 0.00 | 9.79  | 15.08 |
| 21 | 17 | 86.75 | 3.35  | 8.73  | 0.44 | 0.10  | 0.00 | 0.15  | 0.00 | 9.90  | 20.38 |
| 22 | 23 | 84.47 | 3.48  | 10.79 | 0.68 | 0.11  | 0.05 | 0.15  | 0.00 | 12.05 | 15.22 |
| 23 | 21 | 83.83 | 3.33  | 9.80  | 0.65 | 0.00  | 0.00 | 0.25  | 0.00 | 12.84 | 15.51 |
| 24 | 24 | 81.91 | 3.91  | 12.38 | 0.77 | 0.17  | 0.09 | 0.25  | 0.00 | 14.18 | 14.92 |
| 25 | 43 | 77.11 | 6.04  | 17.01 | 1.11 | 0.51  | 0.32 | 1.03  | 0.00 | 16.85 | 12.92 |
| 26 | 42 | 76.73 | 5.19  | 15.18 | 0.82 | 0.46  | 0.35 | 1.01  | 0.04 | 18.08 | 13.75 |
| 27 | 38 | 76.39 | 4.52  | 16.42 | 1.12 | 0.35  | 0.25 | 0.60  | 0.00 | 19.09 | 12.70 |
| 28 | 37 | 75.59 | 4.60  | 16.80 | 1.13 | 0.41  | 0.28 | 0.74  | 0.02 | 19.80 | 12.50 |
| 29 | 28 | 70.77 | 5.85  | 19.62 | 1.43 | 0.00  | 0.00 | 0.65  | 0.00 | 23.38 | 14.14 |
| 30 | 44 | 69.03 | 5.87  | 18.44 | 1.29 | 1.00  | 0.80 | 2.19  | 0.20 | 25.10 | 9.44 |
| 31 | 29 | 67.77 | 6.29  | 22.05 | 1.53 | 0.00  | 0.00 | 0.70  | 0.00 | 25.95 | 14.85 |
| 32 | 34 | 60.21 | 7.47  | 25.88 | 1.50 | 0.00  | 1.16 | 4.30  | 0.44 | 32.32 | 9.76 |
| 33 | 45 | 60.19 | 6.66  | 22.30 | 1.52 | 1.64  | 0.00 | 3.98  | 0.54 | 33.15 | 13.58 |
| 34 | 30 | 46.53 | 9.00  | 6.93  | 2.17 | 0.00  | 1.06 | 2.77  | 0.00 | 44.47 | 12.26 |
| 35 | 26 | 44.14 | 9.91  | 7.44  | 1.91 | 1.86  | 0.91 | 2.72  | 0.08 | 45.95 | 14.51 |
| 36 | 32 | 44.94 | 9.02  | 37.57 | 2.21 | 0.00  | 1.14 | 2.96  | 0.00 | 46.04 | 12.12 |
| 37 | 25 | 42.53 | 10.12 | 38.30 | 1.93 | 2.02  | 0.96 | 2.91  | 0.08 | 47.35 | 14.57 |
| 38 | 31 | 42.64 | 9.56  | 39.78 | 2.26 | 0.00  | 1.21 | 3.20  | 0.00 | 47.80 | 12.38 |
| 39 | 27 | 41.66 | 10.19 | 38.88 | 1.96 | 2.07  | 0.99 | 3.02  | 0.08 | 48.15 | 14.51 |
| 40 | 33 | 41.81 | 9.58  | 40.18 | 2.32 | 0.00  | 1.25 | 3.20  | 0.00 | 48.61 | 12.17 |
| 41 | 40 | 39.17 | 8.23  | 38.06 | 1.75 | 3.05  | 1.78 | 6.14  | 0.59 | 52.60 | 11.46 |
| 42 | 41 | 37.21 | 8.80  | 40.10 | 1.83 | 3.08  | 1.84 | 5.95  | 0.47 | 53.99 | 11.86 |
| 43 | 36 | 34.88 | 8.71  | 42.30 | 2.14 | 3.22  | 1.79 | 5.46  | 0.30 | 56.41 | 12.05 |
| 44 | 35 | 31.96 | 9.09  | 44.42 | 2.19 | 3.55  | 1.94 | 5.90  | 0.32 | 58.95 | 12.12 |
| 45 | 39 | 29.07 | 8.36  | 41.80 | 1.65 | 4.57  | 2.46 | 9.86  | 1.24 | 62.56 | 10.52 |
| 46 | 48 | 97.46 | 0.98  | 1.56  | 0.00 | 0.00  | 0.00 | 0.00  | 0.00 | 1.56  | . |
| 47 | 49 | 97.32 | 1.03  | 1.65  | 0.00 | 0.00  | 0.00 | 0.00  | 0.00 | 1.65  | . |
| 48 | 47 | 92.55 | 1.38  | 2.97  | 0.00 | 0.00  | 0.00 | 0.00  | 0.00 | 6.07  | . |
| 49 | 46 | 88.76 | 1.35  | 2.26  | 0.00 | 0.00  | 0.00 | 0.00  | 0.00 | 9.89  | . |
| 50 | 51 | 75.69 | 6.34  | 13.95 | 0.00 | 0.00  | 0.00 | 0.64  | 0.00 | 17.97 | . |
| 51 | 53 | 75.86 | 6.14  | 13.75 | 0.00 | 0.00  | 0.00 | 0.63  | 0.00 | 18.00 | . |
| 52 | 52 | 75.82 | 6.15  | 13.80 | 0.00 | 0.00  | 0.00 | 0.65  | 0.00 | 18.03 | . |
| 53 | 62 | 78.98 | 2.84  | 11.66 | 0.84 | 0.00  | 0.00 | 0.49  | 0.00 | 18.19 | 14.42 |
| 54 | 50 | 74.75 | 6.17  | 13.73 | 0.00 | 0.00  | 0.00 | 0.64  | 0.00 | 19.08 | . |
| 55 | 65 | 76.10 | 3.12  | 12.97 | 1.00 | 0.00  | 0.00 | 0.58  | 0.00 | 20.78 | 13.59 |
| 56 | 55 | 71.62 | 6.99  | 16.66 | 0.00 | 0.51  | 0.00 | 1.22  | 0.00 | 21.39 | . |
| 57 | 54 | 70.69 | 6.85  | 16.65 | 0.54 | 0.52  | 0.00 | 1.31  | 0.00 | 22.46 | 34.17 |
| 58 | 56 | 66.95 | 8.93  | 18.68 | 1.18 | 0.44  | 0.00 | 1.05  | 0.00 | 24.12 | 17.11 |
| 59 | 57 | 66.18 | 8.97  | 19.00 | 1.17 | 0.26  | 0.00 | 1.06  | 0.00 | 24.85 | 17.35 |
| 60 | 59 | 62.37 | 8.42  | 22.98 | 0.93 | 0.90  | 0.00 | 2.90  | 0.00 | 29.21 | 28.91 |
| 61 | 58 | 62.16 | 8.26  | 22.57 | 1.16 | 0.90  | 0.00 | 2.80  | 0.00 | 29.58 | 22.57 |
| 62 | 69 | 40.36 | 15.45 | 32.77 | 2.22 | 2.78  | 1.53 | 6.82  | 0.01 | 44.20 | 11.31 |
| 63 | 68 | 40.26 | 15.43 | 32.69 | 2.18 | 2.77  | 1.55 | 6.92  | 0.01 | 44.31 | 11.34 |
| 64 | 66 | 35.13 | 16.11 | 34.45 | 2.31 | 3.93  | 2.09 | 9.20  | 0.00 | 48.76 | 10.80 |
| 65 | 67 | 34.12 | 16.41 | 35.09 | 2.35 | 4.00  | 2.15 | 9.51  | 0.00 | 49.47 | 10.80 |
| 66 | 60 | 39.05 | 10.83 | 29.68 | 1.71 | 2.73  | 2.03 | 15.38 | 0.80 | 50.12 | 10.51 |
| 67 | 64 | 37.86 | 11.47 | 29.16 | 1.65 | 2.83  | 2.46 | 17.89 | 1.20 | 50.67 | 9.40 |
| 68 | 61 | 37.39 | 10.86 | 33.64 | 1.82 | 2.74  | 2.50 | 15.65 | 0.70 | 51.76 | 10.34 |
| 69 | 63 | 35.03 | 11.42 | 28.13 | 1.63 | 3.23  | 2.46 | 20.27 | 1.32 | 53.55 | 9.54 |
| 70 | 72 | 8.12  | 13.34 | 24.42 | 1.22 | 13.49 | 6.12 | 36.28 | 5.87 | 78.53 | 5.62 |
| 71 | 73 | 7.31  | 12.98 | 23.09 | 1.14 | 13.28 | 5.98 | 35.78 | 5.87 | 79.72 | 5.55 |
| 72 | 70 | 6.78  | 12.54 | 15.14 | 0.00 | 13.14 | 2.64 | 41.32 | 3.57 | 80.68 | 11.21 |
| 73 | 71 | 6.46  | 12.50 | 14.70 | 0.00 | 13.30 | 2.58 | 41.95 | 3.69 | 81.03 | 11.15 |
| 74 | 75 | 0.00  | 0.00  | 3.60  | 0.00 | 2.86  | 8.06 | 37.90 | 50.55 | 100.00 | 0.76 |
| 75 | 74 | 0.00  | 0.00  | 3.98  | 0.00 | 2.91  | 8.12 | 37.70 | 49.39 | 100.00 | 0.78 |

TABLE 10

ANILINE/PROPYLENE/ZEOLITES
Sorted by O_P

| OBS | SAMPLE ID | RUN | TEMPERATURE | PRESSURE | N | R | CATALYST TYPE | LHSV | CONV | O_P |
|---|---|---|---|---|---|---|---|---|---|---|
| 1 | 7171-41-03 | 1 | 154 | 930 | 1.00 | 10.00 | H—MORDENITE | 0.25 | 2.46 | . |
| 2 | 7644-96-13 | 2 | 201 | 769 | 1.00 | 1.00  | H—MORDENITE | 0.13 | 0.61 | . |
| 3 | 7171-41-06 | 3 | 201 | 950 | 1.00 | 10.00 | H—MORDENITE | 0.25 | 4.40 | . |
| 4 | 7644-96-14 | 4 | 202 | 927 | 1.00 | 2.00  | H—MORDENITE | 0.13 | 0.63 | . |
| 5 | 7644-53-03 | 5 | 204 | 840 | 1.00 | 1.00  | H—MORDENITE | 0.13 | 4.73 | . |

TABLE 10-continued

ANILINE/PROPYLENE/ZEOLITES
Sorted by O_P

| OBS | SAMPLE ID | RUN | TEMPERATURE | PRESSURE | N | R | CATALYST TYPE | LHSV | CONV | O_P |
|---|---|---|---|---|---|---|---|---|---|---|
| 6 | 7723-54-19 | 6 | 208 | 967 | 1.00 | 2.00 | H—MORDENITE | 0.13 | 0.31 | . |
| 7 | 7723-54-20 | 7 | 208 | 963 | 1.00 | 2.00 | H—MORDENITE | 0.13 | 0.21 | . |
| 8 | 7171-43-09 | 9 | 227 | 949 | 1.00 | 10.00 | H—MORDENITE | 0.25 | 5.07 | . |
| 9 | 7723-56-24 | 10 | 228 | 985 | 1.00 | 2.00 | H—MORDENITE | 0.13 | 6.62 | . |
| 10 | 7723-56-25 | 11 | 228 | 978 | 1.00 | 2.00 | H—MORDENITE | 0.13 | 7.10 | . |
| 11 | 7723-49-04 | 12 | 228 | 957 | 1.00 | 2.00 | H—MORDENITE | 0.13 | 3.10 | . |
| 12 | 7723-49-05 | 13 | 228 | 990 | 1.00 | 2.00 | H—MORDENITE | 0.13 | 2.68 | . |
| 13 | 7171-43-17 | 14 | 228 | 956 | 1.00 | 10.00 | H—MORDENITE | 0.25 | 2.61 | . |
| 14 | 7723-57-26 | 15 | 247 | 990 | 1.00 | 2.00 | H—MORDENITE | 0.13 | 6.98 | . |
| 15 | 7644-54-04 | 18 | 252 | 836 | 1.00 | 1.00 | H—MORDENITE | 0.13 | 7.92 | . |
| 16 | 7171-43-11 | 22 | 252 | 956 | 1.00 | 10.00 | H—MORDENITE | 0.25 | 9.00 | . |
| 17 | 7644-97-19 | 44 | 301 | 918 | 1.00 | 2.00 | H—MORDENITE | 0.13 | 25.10 | 9.44 |
| 18 | 7644-74-10 | 34 | 274 | 834 | 1.00 | 2.00 | H—MORDENITE | 0.06 | 32.32 | 9.76 |
| 19 | 7723-68-74 | 39 | 276 | 1013 | 1.00 | 10.00 | H—MORDENITE | 0.03 | 62.56 | 10.52 |
| 20 | 7723-69-77 | 40 | 276 | 1015 | 1.00 | 10.00 | H—MORDENITE | 0.03 | 52.60 | 11.46 |
| 21 | 7723-69-78 | 41 | 276 | 1011 | 1.00 | 10.00 | H—MORDENITE | 0.03 | 53.99 | 11.86 |
| 22 | 7723-66-62 | 36 | 275 | 927 | 1.00 | 2.00 | H—MORDENITE | 0.03 | 56.41 | 12.05 |
| 23 | 7723-66-61 | 35 | 275 | 997 | 1.00 | 2.00 | H—MORDENITE | 0.03 | 58.95 | 12.12 |
| 24 | 7723-59-37 | 32 | 271 | 1004 | 1.00 | 2.00 | H—MORDENITE | 0.13 | 46.04 | 12.12 |
| 25 | 7723-59-38 | 33 | 271 | 1000 | 1.00 | 2.00 | H—MORDENITE | 0.13 | 48.61 | 12.17 |
| 26 | 7723-58-34 | 30 | 271 | 1000 | 1.00 | 2.00 | H—MORDENITE | 0.13 | 44.47 | 12.26 |
| 27 | 7723-58-36 | 31 | 271 | 1004 | 1.00 | 2.00 | H—MORDENITE | 0.13 | 47.80 | 12.38 |
| 28 | 7723-67-67 | 37 | 276 | 1020 | 1.00 | 10.00 | H—MORDENITE | 0.12 | 19.80 | 12.50 |
| 29 | 7723-67-69 | 38 | 276 | 1020 | 1.00 | 10.00 | H—MORDENITE | 0.12 | 19.09 | 12.70 |
| 30 | 7171-43-14 | 43 | 277 | 956 | 1.00 | 10.00 | H—MORDENITE | 0.25 | 16.85 | 12.92 |
| 31 | 7644-98-20 | 45 | 301 | 915 | 1.00 | 2.00 | H—MORDENITE | 0.06 | 33.15 | 13.58 |
| 32 | 7644-97-18 | 42 | 277 | 920 | 1.00 | 2.00 | H—MORDENITE | 0.13 | 18.08 | 13.75 |
| 33 | 7723-57-28 | 28 | 271 | 1000 | 1.00 | 2.00 | H—MORDENITE | 0.13 | 23.38 | 14.14 |
| 34 | 7723-65-56 | 27 | 262 | 1002 | 1.00 | 2.00 | H—MORDENITE | 0.03 | 48.15 | 14.51 |
| 35 | 7723-64-53 | 26 | 262 | 1000 | 1.00 | 2.00 | H—MORDENITE | 0.03 | 45.95 | 14.51 |
| 36 | 7723-64-51 | 25 | 262 | 910 | 1.00 | 2.00 | H—MORDENITE | 0.03 | 47.35 | 14.57 |
| 37 | 7723-57-30 | 29 | 271 | 1005 | 1.00 | 2.00 | H—MORDENITE | 0.13 | 25.95 | 14.85 |
| 38 | 7723-62-46 | 24 | 261 | 1006 | 1.00 | 2.00 | H—MORDENITE | 0.13 | 14.18 | 14.92 |
| 39 | 7644-54-06 | 20 | 252 | 847 | 1.00 | 2.00 | H—MORDENITE | 0.13 | 9.78 | 15.00 |
| 40 | 7644-54-05 | 19 | 252 | 834 | 1.00 | 1.00 | H—MORDENITE | 0.13 | 9.79 | 15.08 |
| 41 | 7723-62-45 | 23 | 261 | 1008 | 1.00 | 2.00 | H—MORDENITE | 0.13 | 12.05 | 15.22 |
| 42 | 7644-55-07 | 21 | 252 | 840 | 1.00 | 2.00 | H—MORDENITE | 0.13 | 12.84 | 15.51 |
| 43 | 7644-97-17 | 17 | 252 | 914 | 1.00 | 2.00 | H—MORDENITE | 0.13 | 9.90 | 20.38 |
| 44 | 7644-97-16 | 16 | 252 | 919 | 1.00 | 2.00 | H—MORDENITE | 0.13 | 9.65 | 20.40 |
| 45 | 7644-96-15 | 8 | 227 | 917 | 1.00 | 2.00 | H—MORDENITE | 0.13 | 2.83 | 24.29 |
| 46 | 7432-08-05 | 46 | 150 | 883 | 1.00 | 1.00 | H—Y | 0.13 | 9.89 | . |
| 47 | 7432-09-06 | 47 | 150 | 883 | 1.00 | 1.00 | H—Y | 0.13 | 6.07 | . |
| 48 | 7171-37-02 | 48 | 154 | 960 | 1.00 | 11.80 | H—Y | 0.25 | 1.56 | . |
| 49 | 7171-37-03 | 49 | 154 | 962 | 1.00 | 10.00 | H—Y | 0.25 | 1.65 | . |
| 50 | 7432-11-11 | 50 | 167 | 910 | 1.00 | 2.00 | H—Y | 0.06 | 19.08 | . |
| 51 | 7432-11-12 | 51 | 167 | 910 | 1.00 | 2.00 | H—Y | 0.06 | 17.97 | . |
| 52 | 7432-12-12 | 52 | 167 | 913 | 1.00 | 1.00 | H—Y | 0.06 | 18.03 | . |
| 53 | 7432-12-13 | 53 | 167 | 911 | 1.00 | 1.00 | H—Y | 0.06 | 18.00 | . |
| 54 | 7432-10-10 | 55 | 182 | 918 | 1.00 | 2.00 | H—Y | 0.13 | 21.39 | . |
| 55 | 7171-39-15 | 75 | 277 | 986 | 1.00 | 10.00 | H—Y | 0.25 | 100.00 | 0.76 |
| 56 | 7171-39-14 | 74 | 277 | 985 | 1.00 | 10.00 | H—Y | 0.25 | 100.00 | 0.78 |
| 57 | 7171-39-12 | 73 | 253 | 988 | 1.00 | 10.00 | H—Y | 0.25 | 79.72 | 5.55 |
| 58 | 7171-39-11 | 72 | 253 | 988 | 1.00 | 10.00 | H—Y | 0.25 | 78.53 | 5.62 |
| 59 | 7432-14-18 | 64 | 227 | 930 | 1.00 | 1.00 | H—Y | 0.06 | 50.67 | 9.40 |
| 60 | 7432-14-16 | 63 | 227 | 928 | 1.00 | 1.00 | H—Y | 0.06 | 53.55 | 9.54 |
| 61 | 7432-15-20 | 61 | 226 | 918 | 2.00 | 1.00 | H—Y | 0.06 | 51.76 | 10.34 |
| 62 | 7432-15-19 | 60 | 226 | 918 | 2.00 | 1.00 | H—Y | 0.06 | 50.12 | 10.51 |
| 63 | 7171-38-18 | 66 | 228 | 990 | 1.00 | 10.00 | H—Y | 0.25 | 48.76 | 10.80 |
| 64 | 7171-39-09 | 67 | 228 | 985 | 1.00 | 10.00 | H—Y | 0.25 | 49.47 | 10.80 |
| 65 | 7723-19-34 | 71 | 228 | 1024 | 1.00 | 10.00 | H—Y | 0.06 | 81.03 | 11.15 |
| 66 | 7723-19-33 | 70 | 228 | 1021 | 1.00 | 10.00 | H—Y | 0.06 | 80.68 | 11.21 |
| 67 | 7171-40-18 | 69 | 228 | 913 | 1.00 | 10.00 | H—Y | 0.25 | 44.20 | 11.31 |
| 68 | 7171-40-17 | 68 | 228 | 913 | 1.00 | 10.00 | H—Y | 0.25 | 44.31 | 11.34 |
| 69 | 7432-23-23 | 65 | 227 | 931 | 4.00 | 1.00 | H—Y | 0.06 | 20.78 | 13.59 |
| 70 | 7432-23-22 | 62 | 226 | 928 | 4.00 | 1.00 | H—Y | 0.06 | 18.19 | 14.42 |
| 71 | 7171-38-05 | 56 | 202 | 972 | 1.00 | 10.00 | H—Y | 0.25 | 24.12 | 17.11 |
| 72 | 7171-38-16 | 57 | 202 | 972 | 1.00 | 10.00 | H—Y | 0.25 | 24.85 | 17.35 |
| 73 | 7432-09-07 | 58 | 203 | 907 | 1.00 | 10.00 | H—Y | 0.25 | 29.58 | 22.57 |
| 74 | 7432-09-08 | 59 | 203 | 910 | 1.00 | 10.00 | H—Y | 0.25 | 29.21 | 28.91 |
| 75 | 7432-10-09 | 54 | 182 | 911 | 1.00 | 2.00 | H—Y | 0.13 | 22.46 | 34.17 |

TABLE 11

ANILINE/PROPYLENE/ZEOLITES
Sorted by O_P

| OBS | RUN | ANILINE MOLE PCT | N—IPA MOLE PCT | 2-IPA MOLE PCT | 4-IPA MOLE PCT | N,2-DIPA MOLE PCT | 2,4-DIPA MOLE PCT | 2,6-DIPA MOLE PCT | 2,4,6-TIPA MOLE PCT | CONV | O_P |
|---|---|---|---|---|---|---|---|---|---|---|---|
| 1 | 1 | 96.65 | 0.88 | 1.45 | 0.00 | 0.00 | 0.00 | 0.00 | 0.00 | 2.46 | . |
| 2 | 2 | 99.39 | 0.00 | 0.13 | 0.00 | 0.00 | 0.00 | 0.00 | 0.00 | 0.61 | . |
| 3 | 3 | 94.37 | 1.23 | 2.77 | 0.00 | 0.00 | 0.00 | 0.00 | 0.00 | 4.40 | . |
| 4 | 4 | 99.24 | 0.13 | 0.30 | 0.00 | 0.00 | 0.00 | 0.00 | 0.00 | 0.63 | . |
| 5 | 5 | 95.27 | 0.00 | 0.42 | 0.00 | 0.00 | 0.00 | 0.00 | 0.00 | 4.73 | . |
| 6 | 6 | 99.69 | 0.00 | 1.10 | 0.00 | 0.00 | 0.00 | 0.00 | 0.00 | 0.31 | . |
| 7 | 7 | 99.79 | 0.00 | 1.12 | 0.00 | 0.00 | 0.00 | 0.00 | 0.00 | 0.21 | . |
| 8 | 9 | 92.71 | 2.22 | 5.53 | 0.00 | 0.00 | 0.00 | 0.00 | 0.00 | 5.07 | . |
| 9 | 10 | 92.04 | 1.33 | 4.13 | 0.00 | 0.00 | 0.00 | 0.00 | 0.00 | 6.62 | . |
| 10 | 11 | 91.42 | 1.48 | 4.52 | 0.00 | 0.00 | 0.00 | 0.00 | 0.00 | 7.10 | . |
| 11 | 12 | 94.09 | 2.82 | 2.77 | 0.00 | 0.00 | 0.00 | 0.00 | 0.00 | 3.10 | . |
| 12 | 13 | 95.80 | 1.52 | 2.68 | 0.00 | 0.00 | 0.00 | 0.00 | 0.00 | 2.68 | . |
| 13 | 14 | 95.94 | 1.45 | 3.66 | 0.00 | 0.00 | 0.00 | 0.00 | 0.00 | 2.61 | . |
| 14 | 15 | 91.64 | 1.38 | 4.27 | 0.00 | 0.00 | 0.00 | 0.00 | 0.00 | 6.98 | . |
| 15 | 18 | 90.27 | 1.81 | 5.10 | 0.00 | 0.00 | 0.00 | 0.00 | 0.00 | 7.92 | . |
| 16 | 22 | 87.04 | 3.96 | 10.22 | 0.00 | 0.00 | 0.00 | 0.00 | 0.00 | 9.00 | . |
| 17 | 44 | 69.03 | 5.87 | 18.44 | 1.29 | 1.00 | 0.80 | 2.19 | 0.20 | 25.10 | 9.44 |
| 18 | 34 | 60.21 | 7.47 | 25.88 | 1.50 | 0.00 | 1.16 | 4.30 | 0.44 | 32.32 | 9.76 |
| 19 | 39 | 29.07 | 8.36 | 41.80 | 1.65 | 4.57 | 2.46 | 9.86 | 1.24 | 62.56 | 10.52 |
| 20 | 40 | 39.17 | 8.23 | 38.06 | 1.75 | 3.05 | 1.78 | 6.14 | 0.59 | 52.60 | 11.46 |
| 21 | 41 | 37.21 | 8.80 | 40.10 | 1.83 | 3.08 | 1.84 | 5.95 | 0.47 | 53.99 | 11.86 |
| 22 | 36 | 34.88 | 8.71 | 42.30 | 2.14 | 3.22 | 1.79 | 5.46 | 0.30 | 56.41 | 12.05 |
| 23 | 35 | 31.96 | 9.09 | 44.42 | 2.19 | 3.55 | 1.94 | 5.90 | 0.32 | 58.95 | 12.12 |
| 24 | 32 | 44.94 | 9.02 | 37.57 | 2.21 | 0.00 | 1.14 | 2.96 | 0.00 | 46.04 | 12.12 |
| 25 | 33 | 41.81 | 9.58 | 40.18 | 2.32 | 0.00 | 1.25 | 3.20 | 0.00 | 48.61 | 12.17 |
| 26 | 30 | 46.53 | 9.00 | 36.93 | 2.17 | 0.00 | 1.06 | 2.77 | 0.00 | 44.47 | 12.26 |
| 27 | 31 | 42.64 | 9.56 | 39.78 | 2.26 | 0.00 | 1.21 | 3.20 | 0.00 | 47.80 | 12.38 |
| 28 | 37 | 75.59 | 4.60 | 16.80 | 1.13 | 0.41 | 0.28 | 0.74 | 0.02 | 19.80 | 12.50 |
| 29 | 38 | 76.39 | 4.52 | 16.42 | 1.12 | 0.35 | 0.25 | 0.60 | 0.00 | 19.09 | 12.70 |
| 30 | 43 | 77.11 | 6.04 | 17.01 | 1.11 | 0.51 | 0.32 | 1.03 | 0.00 | 16.85 | 12.92 |
| 31 | 45 | 60.19 | 6.66 | 22.30 | 1.52 | 1.64 | 0.00 | 3.98 | 0.54 | 33.15 | 13.58 |
| 32 | 42 | 76.73 | 5.19 | 15.18 | 0.82 | 0.46 | 0.35 | 1.01 | 0.04 | 18.08 | 13.75 |
| 33 | 28 | 70.77 | 5.85 | 19.62 | 1.43 | 0.00 | 0.00 | 0.65 | 0.00 | 22.38 | 14.14 |
| 34 | 27 | 41.66 | 10.19 | 38.88 | 1.96 | 2.07 | 0.99 | 3.02 | 0.08 | 48.15 | 14.51 |
| 35 | 26 | 44.14 | 9.91 | 37.44 | 1.91 | 1.86 | 0.91 | 2.72 | 0.08 | 45.95 | 14.51 |
| 36 | 25 | 42.53 | 10.12 | 38.30 | 1.93 | 2.02 | 0.96 | 2.91 | 0.08 | 47.35 | 14.57 |
| 37 | 29 | 67.77 | 6.29 | 22.05 | 1.53 | 0.00 | 0.00 | 0.70 | 0.00 | 25.95 | 14.85 |
| 38 | 24 | 81.91 | 3.91 | 12.38 | 0.77 | 0.17 | 0.09 | 0.25 | 0.00 | 14.18 | 14.92 |
| 39 | 20 | 87.84 | 2.38 | 6.79 | 0.45 | 0.00 | 0.00 | 0.00 | 0.00 | 9.78 | 15.00 |
| 40 | 19 | 86.82 | 3.40 | 9.54 | 0.63 | 0.00 | 0.00 | 0.00 | 0.00 | 9.79 | 15.08 |
| 41 | 23 | 84.47 | 3.48 | 10.79 | 0.68 | 0.11 | 0.05 | 0.15 | 0.00 | 12.05 | 15.22 |
| 42 | 21 | 83.83 | 3.33 | 9.80 | 0.65 | 0.00 | 0.00 | 0.25 | 0.00 | 12.84 | 15.51 |
| 43 | 17 | 86.75 | 3.35 | 8.73 | 0.44 | 0.10 | 0.00 | 0.15 | 0.00 | 9.90 | 20.38 |
| 44 | 16 | 87.11 | 3.25 | 8.44 | 0.43 | 0.09 | 0.00 | 0.14 | 0.00 | 9.65 | 20.40 |
| 45 | 8 | 96.22 | 0.95 | 2.39 | 0.10 | 0.00 | 0.00 | 0.00 | 0.00 | 2.83 | 24.29 |
| 46 | 46 | 88.76 | 1.35 | 2.26 | 0.00 | 0.00 | 0.00 | 0.00 | 0.00 | 9.89 | . |
| 47 | 47 | 92.55 | 1.38 | 2.97 | 0.00 | 0.00 | 0.00 | 0.00 | 0.00 | 6.07 | . |
| 48 | 48 | 97.46 | 0.98 | 1.56 | 0.00 | 0.00 | 0.00 | 0.00 | 0.00 | 1.56 | . |
| 49 | 49 | 97.32 | 1.03 | 1.65 | 0.00 | 0.00 | 0.00 | 0.00 | 0.00 | 1.65 | . |
| 50 | 50 | 74.75 | 6.17 | 13.73 | 0.00 | 0.00 | 0.00 | 0.64 | 0.00 | 19.08 | . |
| 51 | 51 | 75.69 | 6.34 | 13.95 | 0.00 | 0.00 | 0.00 | 0.64 | 0.00 | 17.97 | . |
| 52 | 52 | 75.82 | 6.15 | 13.80 | 0.00 | 0.00 | 0.00 | 0.65 | 0.00 | 18.03 | . |
| 53 | 53 | 75.86 | 6.14 | 13.75 | 0.00 | 0.00 | 0.00 | 0.63 | 0.00 | 18.00 | . |
| 54 | 55 | 71.62 | 6.99 | 16.66 | 0.00 | 0.51 | 0.00 | 1.22 | 0.00 | 21.39 | . |
| 55 | 75 | 0.00 | 0.00 | 3.60 | 0.00 | 2.86 | 8.06 | 37.90 | 50.55 | 100.00 | 0.76 |
| 56 | 74 | 0.00 | 0.00 | 3.98 | 0.00 | 2.91 | 8.12 | 37.70 | 49.39 | 100.00 | 0.78 |
| 57 | 73 | 7.31 | 12.98 | 23.09 | 1.14 | 13.28 | 5.98 | 35.78 | 5.87 | 79.72 | 5.55 |
| 58 | 72 | 8.12 | 13.34 | 24.42 | 1.22 | 13.49 | 6.12 | 36.28 | 5.87 | 78.53 | 5.62 |
| 59 | 64 | 37.86 | 11.47 | 29.16 | 1.65 | 2.83 | 2.46 | 17.89 | 1.20 | 50.67 | 9.40 |
| 60 | 63 | 35.03 | 11.42 | 28.13 | 1.63 | 3.23 | 2.46 | 20.27 | 1.32 | 53.55 | 9.54 |
| 61 | 61 | 37.39 | 10.86 | 33.64 | 1.82 | 2.74 | 2.50 | 15.65 | 0.70 | 51.76 | 10.34 |
| 62 | 60 | 39.05 | 10.83 | 29.68 | 1.71 | 2.73 | 2.03 | 15.38 | 0.80 | 50.12 | 10.51 |
| 63 | 66 | 35.13 | 16.11 | 34.45 | 2.31 | 3.93 | 2.09 | 9.20 | 0.00 | 48.76 | 10.80 |
| 64 | 67 | 34.12 | 16.41 | 35.09 | 2.35 | 4.00 | 2.15 | 9.51 | 0.00 | 49.47 | 10.80 |
| 65 | 71 | 6.46 | 12.50 | 14.70 | 0.00 | 13.30 | 2.58 | 41.95 | 3.69 | 81.03 | 11.15 |
| 66 | 70 | 6.78 | 12.54 | 15.14 | 0.00 | 13.14 | 2.64 | 41.32 | 3.57 | 80.68 | 11.21 |
| 67 | 69 | 40.36 | 15.45 | 32.77 | 2.22 | 2.78 | 1.53 | 6.82 | 0.01 | 44.20 | 11.31 |
| 68 | 68 | 40.26 | 15.43 | 32.69 | 2.18 | 2.77 | 1.55 | 6.92 | 0.01 | 44.31 | 11.34 |
| 69 | 65 | 76.10 | 3.12 | 12.97 | 1.00 | 0.00 | 0.00 | 0.58 | 0.00 | 20.78 | 13.59 |
| 70 | 62 | 78.98 | 2.84 | 11.66 | 0.84 | 0.00 | 0.00 | 0.49 | 0.00 | 18.19 | 14.42 |
| 71 | 56 | 66.95 | 8.93 | 18.68 | 1.18 | 0.44 | 0.00 | 1.05 | 0.00 | 24.12 | 17.11 |
| 72 | 57 | 66.18 | 8.97 | 19.00 | 1.17 | 0.26 | 0.00 | 1.06 | 0.00 | 24.85 | 17.35 |
| 73 | 58 | 62.16 | 8.26 | 22.57 | 1.16 | 0.90 | 0.00 | 2.80 | 0.00 | 29.58 | 22.57 |
| 74 | 59 | 62.37 | 8.42 | 22.98 | 0.93 | 0.90 | 0.00 | 2.90 | 0.00 | 29.21 | 28.91 |
| 75 | 54 | 70.69 | 6.85 | 16.65 | 0.54 | 0.52 | 0.00 | 1.31 | 0.00 | 22.46 | 34.17 |

In reviewing the data in the tables, one should focus on trends within the tables rather than on specific runs since, as with most reactions, there may be excursions. Tables 8 and 9 and tables 10 and 11 are arranged in ascending conversion and ortho-para ratios respectively and these tables can be used in combination with others to observe the effect of temperature and pressure along with space velocity. As is generally noted from tables 4 and 5 conversion increases with increasing temperature at a constant LHSV and constant N/R ratio. The results also show that propylene alkylation of aniline, in the presence of H-mordenite, is not as temperature sensitive, in terms of ortho-para ratio, as H-Y zeolite. Conversions at comparable pressures at 250° C. range from about 9 to 15% while conversions with H-Y range about 80%. On the other hand at 250° C. levels the ortho-para ratio decreases from about 14 1 for H-mordenite to about 5 for the H-Y. Although temperature did increase the conversion for H-mordenite, generally lower LHSV values were required to achieve high conversions, note run 35, 36, 38–40, while higher LHSV run 42. In contrast to Exaample 2, runs 9–11 which utilize a larger pore size H-mordenite than the H-mordenite of these runs, conversion was higher and selectivity was higher. It is believed the major difference in the runs between H-mordenite and H-Y as compared to the H-mordenite of Example 2, is the molecular diffusion resistance of the smaller pore sized H-mordenite.

The data does show that for H-Y zeolite, namely runs 66–71 (obs 66–71), that propylene alkylates can be achieved in high conversion and high ortho-para ratios at temperature from about 215°–230° C. at space velocities of 0.06–0.25 hours$^{-1}$ while temperatures as high as 250° C. reduce the ortho-para isomer ratio by a factor of 2 in runs 72 and 73 (obs 72 and 73). Good selectivity may be obtained with HY at 250° C. if higher space velocities are used and less 2,4,6-trialkylate product is formed. One important observation with all runs using the highly active acidic zeolites is that ring alkylation, as opposed to N-alkylation, was always greater than 2 even at low conversion.

TABLE 12

ANILINE/ISOBUTYLENE
Sorted by Temperature

| OBS | SAMPLE ID | RUN | TEMPERATURE | PRESSURE | N | R | CATALYST TYPE | LHSV | CONV | O_P |
|---|---|---|---|---|---|---|---|---|---|---|
| 14 | 7432-81-01 | 14 | 103 | 887 | 1.00 | 4.00 | H—Y | 0.13 | 12.76 | 9.28 |
| 15 | 7432-82-06 | 15 | 127 | 907 | 1.00 | 1.00 | H—Y | 0.06 | 50.77 | 6.51 |
| 16 | 7432-81-02 | 16 | 128 | 894 | 1.00 | 4.00 | H—Y | 0.13 | 42.69 | 7.00 |
| 17 | 7432-81-03 | 17 | 128 | 898 | 1.00 | 4.00 | H—Y | 0.13 | 43.40 | 7.04 |
| 18 | 7432-82-04 | 18 | 128 | 899 | 1.00 | 4.00 | H—Y | 0.06 | 59.42 | 6.78 |
| 19 | 7432-82-05 | 19 | 128 | 900 | 1.00 | 4.00 | H—Y | 0.06 | 57.43 | 6.72 |
| 20 | 7432-82-07 | 20 | 129 | 886 | 1.00 | 1.00 | H—Y | 0.06 | 12.05 | 7.35 |
| 21 | 7432-84-14 | 21 | 152 | 888 | 1.00 | 1.00 | H—Y | 0.06 | 64.39 | 4.86 |
| 22 | 7432-84-15 | 22 | 152 | 896 | 1.00 | 1.00 | H—Y | 0.06 | 65.49 | 4.83 |
| 23 | 7432-86-19 | 23 | 178 | 898 | 1.00 | 1.00 | H—Y | 0.06 | 73.07 | 0.99 |

TABLE 13

ANILINE/ISOBUTYLENE
Sorted by Temperature

| OBS | RUN | ANILINE MOLE PCT | N—T-BUTYL ANILINE MOLE PCT | O—T-BUTYL ANILINE MOLE PCT | P-T-BUTYL ANILINE MOLE PCT | N,2-DIBUT ANILINE MOLE PCT | 2,4-DIBUT ANILINE MOLE PCT | DIPHENYL AMINE MOLE PCT | CONV | O_P |
|---|---|---|---|---|---|---|---|---|---|---|
| 14 | 14 | 87.24 | 6.10 | 5.21 | 0.56 | 0.00 | 0.00 | 0.00 | 12.76 | 9.28 |
| 15 | 15 | 49.23 | 25.30 | 20.09 | 2.69 | 0.08 | 0.40 | 0.00 | 50.77 | 6.51 |
| 16 | 16 | 57.31 | 23.01 | 16.14 | 2.19 | 0.00 | 0.11 | 0.00 | 42.69 | 7.00 |
| 17 | 17 | 56.60 | 23.50 | 16.73 | 2.26 | 0.00 | 0.12 | 0.00 | 43.40 | 7.04 |
| 18 | 18 | 40.58 | 29.76 | 22.00 | 2.95 | 0.06 | 0.31 | 0.00 | 59.42 | 6.78 |
| 19 | 19 | 42.57 | 30.31 | 22.78 | 3.08 | 0.06 | 0.32 | 0.00 | 57.43 | 6.72 |
| 20 | 20 | 87.95 | 5.40 | 5.53 | 0.75 | 0.00 | 0.00 | 0.00 | 12.05 | 7.35 |
| 21 | 21 | 35.61 | 18.39 | 36.71 | 6.02 | 0.34 | 1.60 | 0.00 | 64.39 | 4.86 |
| 22 | 22 | 34.51 | 18.25 | 36.51 | 5.96 | 0.37 | 1.68 | 0.00 | 65.49 | 4.83 |
| 23 | 23 | 26.93 | 2.18 | 33.33 | 20.89 | 1.43 | 14.24 | 0.00 | 73.07 | 0.99 | resulted in lower conversion at similar temperature, e.g.

TABLE 14

ANILINE/ISOBUTYLENE
Sorted by Pressure

| OBS | SAMPLE ID | RUN | TEMPERATURE | PRESSURE | N | R | CATALYST TYPE | LHSV | CONV | O_P |
|---|---|---|---|---|---|---|---|---|---|---|
| 14 | 7432-82-07 | 20 | 129 | 886 | 1.00 | 1.00 | H—Y | 0.06 | 12.05 | 7.35 |
| 15 | 7432-81-01 | 14 | 103 | 887 | 1.00 | 4.00 | H—Y | 0.13 | 12.76 | 9.28 |
| 16 | 7432-84-14 | 21 | 152 | 888 | 1.00 | 1.00 | H—Y | 0.06 | 64.39 | 4.86 |
| 17 | 7432-81-02 | 16 | 128 | 894 | 1.00 | 4.00 | H—Y | 0.13 | 42.69 | 7.00 |
| 18 | 7432-84-15 | 22 | 152 | 896 | 1.00 | 1.00 | H—Y | 0.06 | 65.49 | 4.83 |
| 19 | 7432-81-03 | 17 | 128 | 898 | 1.00 | 4.00 | H—Y | 0.13 | 43.40 | 7.04 |
| 20 | 7432-86-19 | 23 | 178 | 898 | 1.00 | 1.00 | H—Y | 0.06 | 73.07 | 0.99 |
| 21 | 7432-82-04 | 18 | 128 | 899 | 1.00 | 4.00 | H—Y | 0.06 | 59.42 | 6.78 |
| 22 | 7432-82-05 | 19 | 128 | 900 | 1.00 | 4.00 | H—Y | 0.06 | 57.43 | 6.72 |
| 23 | 7432-82-06 | 15 | 127 | 907 | 1.00 | 1.00 | H—Y | 0.06 | 50.77 | 6.51 |

TABLE 15

ANILINE/ISOBUTYLENE
Sorted by Pressure

| OBS | RUN | ANILINE MOLE PCT | N-T-BUTYL ANILINE MOLE PCT | O-T-BUTYL ANILINE MOLE PCT | P-T-BUTYL ANILINE MOLE PCT | N,2-DIBUT ANILINE MOLE PCT | 2,4-DIBUT ANILINE MOLE PCT | DIPHENYL AMINE MOLE PCT | CONV | O_P |
|---|---|---|---|---|---|---|---|---|---|---|
| 14 | 20 | 87.95 | 5.40 | 5.53 | 0.75 | 0.00 | 0.00 | 0.00 | 12.05 | 7.35 |
| 15 | 14 | 87.24 | 6.10 | 5.21 | 0.56 | 0.00 | 0.00 | 0.00 | 12.76 | 9.28 |
| 16 | 21 | 35.61 | 18.39 | 36.71 | 6.02 | 0.34 | 1.60 | 0.00 | 64.39 | 4.86 |
| 17 | 16 | 57.31 | 23.01 | 16.14 | 2.19 | 0.00 | 0.11 | 0.00 | 42.69 | 7.00 |
| 18 | 22 | 34.51 | 18.25 | 36.51 | 5.96 | 0.37 | 1.68 | 0.00 | 65.49 | 4.83 |
| 19 | 17 | 56.60 | 23.50 | 16.73 | 2.26 | 0.00 | 0.12 | 0.00 | 43.40 | 7.04 |
| 20 | 23 | 26.93 | 2.18 | 33.33 | 20.89 | 1.43 | 14.24 | 0.00 | 73.07 | 0.99 |
| 21 | 18 | 40.58 | 29.76 | 22.00 | 2.95 | 0.06 | 0.31 | 0.00 | 59.42 | 6.78 |
| 22 | 19 | 42.57 | 30.31 | 22.78 | 3.08 | 0.06 | 0.32 | 0.00 | 57.43 | 6.72 |
| 23 | 15 | 49.23 | 25.30 | 20.09 | 2.69 | 0.08 | 0.40 | 0.00 | 50.77 | 6.51 |

TABLE 16

ANILINE/ISOBUTYLENE
Sorted by Conversion

| OBS | SAMPLE ID | RUN | TEMPERATURE | PRESSURE | N | R | CATALYST TYPE | LHSV | CONV | O_P |
|---|---|---|---|---|---|---|---|---|---|---|
| 14 | 7432-82-07 | 20 | 129 | 886 | 1.00 | 1.00 | H—Y | 0.06 | 12.05 | 7.35 |
| 15 | 7432-81-01 | 14 | 103 | 887 | 1.00 | 4.00 | H—Y | 0.13 | 12.76 | 9.28 |
| 16 | 7432-81-02 | 16 | 128 | 894 | 1.00 | 4.00 | H—Y | 0.13 | 42.69 | 7.00 |
| 17 | 7432-81-03 | 17 | 128 | 898 | 1.00 | 4.00 | H—Y | 0.13 | 43.40 | 7.04 |
| 18 | 7432-82-06 | 15 | 127 | 907 | 1.00 | 1.00 | H—Y | 0.06 | 50.77 | 6.51 |
| 19 | 7432-82-05 | 19 | 128 | 900 | 1.00 | 4.00 | H—Y | 0.06 | 57.43 | 6.72 |
| 20 | 7432-82-04 | 18 | 128 | 899 | 1.00 | 4.00 | H—Y | 0.06 | 59.42 | 6.78 |
| 21 | 7432-84-14 | 21 | 152 | 888 | 1.00 | 1.00 | H—Y | 0.06 | 64.39 | 4.86 |
| 22 | 7432-84-15 | 22 | 152 | 896 | 1.00 | 1.00 | H—Y | 0.06 | 65.49 | 4.83 |
| 23 | 7432-86-19 | 23 | 178 | 898 | 1.00 | 1.00 | H—Y | 0.06 | 73.07 | 0.99 |

TABLE 17

ANILINE/ISOBUTYLENE
Sorted by Pressure

| OBS | RUN | ANILINE MOLE PCT | N-T-BUTYL ANILINE MOLE PCT | O-T-BUTYL ANILINE MOLE PCT | P-T-BUTYL ANILINE MOLE PCT | N,2-DIBUT ANILINE MOLE PCT | 2,4-DIBUT ANILINE MOLE PCT | DIPHENYL AMINE MOLE PCT | CONV | O_P |
|---|---|---|---|---|---|---|---|---|---|---|
| 14 | 20 | 87.95 | 5.40 | 5.53 | 0.75 | 0.00 | 0.00 | 0.00 | 12.05 | 7.35 |
| 15 | 14 | 87.24 | 6.10 | 5.21 | 0.56 | 0.00 | 0.00 | 0.00 | 12.76 | 9.28 |
| 16 | 16 | 57.31 | 23.01 | 16.14 | 2.19 | 0.00 | 0.11 | 0.00 | 42.69 | 7.00 |
| 17 | 17 | 56.60 | 23.50 | 16.73 | 2.26 | 0.00 | 0.12 | 0.00 | 43.40 | 7.04 |
| 18 | 15 | 49.23 | 25.30 | 20.09 | 2.69 | 0.08 | 0.40 | 0.00 | 50.77 | 6.51 |
| 19 | 19 | 42.57 | 30.31 | 22.78 | 3.08 | 0.06 | 0.32 | 0.00 | 57.43 | 6.72 |
| 20 | 18 | 40.58 | 29.76 | 22.00 | 2.95 | 0.06 | 0.31 | 0.00 | 59.42 | 6.78 |
| 21 | 21 | 35.61 | 18.39 | 36.71 | 6.02 | 0.34 | 1.60 | 0.00 | 64.39 | 4.86 |
| 22 | 22 | 34.51 | 18.25 | 36.51 | 5.96 | 0.37 | 1.68 | 0.00 | 65.49 | 4.83 |
| 23 | 23 | 26.93 | 2.18 | 33.33 | 20.89 | 1.43 | 14.24 | 0.00 | 73.07 | 0.99 |

TABLE 18

ANILINE/ISOBUTYLENE
Sorted by O_P

| OBS | SAMPLE ID | RUN | TEMPERATURE | PRESSURE | N | R | CATALYST TYPE | LHSV | CONV | O_P |
|---|---|---|---|---|---|---|---|---|---|---|
| 14 | 7432-86-19 | 23 | 178 | 898 | 1.00 | 1.00 | H—Y | 0.06 | 73.07 | 0.99 |
| 15 | 7432-84-15 | 22 | 152 | 896 | 1.00 | 1.00 | H—Y | 0.06 | 65.49 | 4.83 |
| 16 | 7432-84-14 | 21 | 152 | 888 | 1.00 | 1.00 | H—Y | 0.06 | 64.39 | 4.86 |
| 17 | 7432-82-06 | 15 | 127 | 907 | 1.00 | 1.00 | H—Y | 0.06 | 50.77 | 6.51 |
| 18 | 7432-82-05 | 19 | 128 | 900 | 1.00 | 4.00 | H—Y | 0.06 | 57.43 | 6.72 |
| 19 | 7432-82-04 | 18 | 128 | 899 | 1.00 | 4.00 | H—Y | 0.06 | 59.42 | 6.78 |
| 20 | 7432-81-02 | 16 | 128 | 894 | 1.00 | 4.00 | H—Y | 0.13 | 42.69 | 7.00 |
| 21 | 7432-81-03 | 17 | 128 | 898 | 1.00 | 4.00 | H—Y | 0.13 | 43.40 | 7.04 |
| 22 | 7432-82-07 | 20 | 129 | 886 | 1.00 | 1.00 | H—Y | 0.06 | 12.05 | 7.35 |
| 23 | 7432-81-01 | 14 | 103 | 887 | 1.00 | 4.00 | H—Y | 0.13 | 12.76 | 9.28 |

TABLE 19

ANILINE/ISOBUTYLENE
Sorted by O_P

| OBS | RUN | ANILINE MOLE PCT | N-T-BUTYL ANILINE MOLE PCT | O-T-BUTYL ANILINE MOLE PCT | P-T-BUTYL ANILINE MOLE PCT | N,2-DIBUT ANILINE MOLE PCT | 2,4-DIBUT ANILINE MOLE PCT | DIPHENYL AMINE MOLE PCT | CONV | O_P |
|---|---|---|---|---|---|---|---|---|---|---|
| 14 | 23 | 26.93 | 2.18 | 33.33 | 20.89 | 1.43 | 14.24 | 0.00 | 73.07 | 0.99 |
| 15 | 22 | 34.51 | 18.25 | 36.51 | 5.96 | 0.37 | 1.68 | 0.00 | 65.49 | 4.83 |

TABLE 19-continued

ANILINE/ISOBUTYLENE
Sorted by O_P

| OBS | RUN | ANILINE MOLE PCT | N-T-BUTYL ANILINE MOLE PCT | O-T-BUTYL ANILINE MOLE PCT | P-T-BUTYL ANILINE MOLE PCT | N,2-DIBUT ANILINE MOLE PCT | 2,4-DIBUT ANILINE MOLE PCT | DIPHENYL AMINE MOLE PCT | CONV | O_P |
|---|---|---|---|---|---|---|---|---|---|---|
| 16 | 21 | 35.61 | 18.39 | 36.71 | 6.02 | 0.34 | 1.60 | 0.00 | 64.39 | 4.86 |
| 17 | 15 | 49.23 | 25.30 | 20.09 | 2.69 | 0.08 | 0.40 | 0.00 | 50.77 | 6.51 |
| 18 | 19 | 42.57 | 30.31 | 22.78 | 3.08 | 0.06 | 0.32 | 0.00 | 57.43 | 6.72 |
| 19 | 18 | 40.58 | 29.76 | 22.00 | 2.95 | 0.06 | 0.31 | 0.00 | 59.42 | 6.78 |
| 20 | 16 | 57.31 | 23.01 | 16.14 | 2.19 | 0.00 | 0.11 | 0.00 | 42.69 | 7.00 |
| 21 | 17 | 56.60 | 23.50 | 16.73 | 2.26 | 0.00 | 0.12 | 0.00 | 43.40 | 7.04 |
| 22 | 20 | 87.95 | 5.40 | 5.53 | 0.75 | 0.00 | 0.00 | 0.00 | 12.05 | 7.35 |
| 23 | 14 | 87.24 | 6.10 | 5.21 | 0.56 | 0.00 | 0.00 | 0.00 | 12.76 | 9.28 |

From the data in tables 12–19 it is shown that the alkylation of aniline with isobutylene is much more sensitive than the alkylation of aniline with propylene to reaction temperature. For example at temperatures of about 125°–130° C. conversions ranged from about 42 to 60% with an ortho-para ratio of 6–7. When temperatures increased to 150° C., although the N/R ratio was 1:1, the ortho-para ratio decreased to about 5. At a temperature of 180° C. the ortho-para ratio had decreased to less than 1.

TABLE 20

ANILINE/CYCLOHEXENE/ACID CATALYST
Sorted by Temperature

| OBS | SAMPLE ID | RUN | TEMPERATURE | PRESSURE | N | R | CATALYST TYPE | LHSV | CONV | O_P |
|---|---|---|---|---|---|---|---|---|---|---|
| 1 | 7893-34-24 | 1 | 150 | 922 | 1.00 | 3.00 | H—Y | 0.13 | 1.02 | . |
| 2 | 7893-34-25 | 2 | 150 | 920 | 1.00 | 3.00 | H—Y | 0.13 | 1.06 | . |
| 3 | 7893-35-26 | 3 | 174 | 934 | 1.00 | 3.00 | H—Y | 0.13 | 5.59 | 7.80 |
| 4 | 7893-35-28 | 4 | 174 | 934 | 1.00 | 3.00 | H—Y | 0.13 | 5.29 | 8.09 |
| 5 | 7893-35-30 | 5 | 200 | 940 | 1.00 | 3.00 | H—Y | 0.13 | 36.25 | 7.17 |
| 6 | 7893-36-31 | 6 | 200 | 940 | 1.00 | 3.00 | H—Y | 0.13 | 38.33 | 7.05 |
| 7 | 7893-48-41 | 7 | 224 | 940 | 1.00 | 3.00 | H—Y | 0.13 | 75.05 | 5.19 |
| 8 | 7893-48-42 | 8 | 224 | 948 | 1.00 | 3.00 | H—Y | 0.13 | 75.19 | 5.26 |
| 9 | 7893-49-44 | 9 | 224 | 936 | 1.00 | 3.00 | H—Y | 0.06 | 87.38 | 5.21 |
| 10 | 7893-49-45 | 10 | 224 | 933 | 1.00 | 3.00 | H—Y | 0.06 | 89.43 | 5.18 |
| 11 | 7893-36-32 | 11 | 225 | 940 | 1.00 | 3.00 | H—Y | 0.13 | 80.36 | 5.28 |
| 12 | 7893-37-34 | 12 | 225 | 937 | 1.00 | 3.00 | H—Y | 0.13 | 84.42 | 5.26 |
| 13 | 7893-38-36 | 13 | 250 | 950 | 1.00 | 3.00 | H—Y | 0.13 | 95.15 | 3.74 |
| 14 | 7893-38-38 | 14 | 250 | 955 | 1.00 | 3.00 | H—Y | 0.13 | 96.26 | 3.63 |

TABLE 21

ANILINE/CYCLOHEXENE ACID CAT
Sorted by Temperature

| OBS | RUN | ANILINE MOLE PCT | N-CYCLOHEX ANILINE MOLE PCT | O-CYCLOHEX ANILINE MOLE PCT | P-CYCLOHEX ANILINE MOLE PCT | N,2-DIHEX ANILINE MOLE PCT | 2,4-DIHEX ANILINE MOLE PCT | 2,6-DIHEX ANILINE MOLE PCT | CONV | O_P |
|---|---|---|---|---|---|---|---|---|---|---|
| 1 | 1 | 98.98 | 0.09 | 0.20 | 0.00 | 0.10 | 0.00 | 0.00 | 1.02 | . |
| 2 | 2 | 98.94 | 0.13 | 0.28 | 0.00 | 0.08 | 0.00 | 0.00 | 1.06 | . |
| 3 | 3 | 94.41 | 1.69 | 3.29 | 0.44 | 0.10 | 0.00 | 0.00 | 5.59 | 7.80 |
| 4 | 4 | 94.71 | 1.77 | 3.63 | 0.46 | 0.09 | 0.00 | 0.00 | 5.29 | 8.09 |
| 5 | 5 | 63.75 | 12.73 | 21.34 | 2.95 | 0.28 | 0.08 | 0.09 | 36.25 | 7.17 |
| 6 | 6 | 61.67 | 13.10 | 21.90 | 3.08 | 0.29 | 0.08 | 0.09 | 38.33 | 7.05 |
| 7 | 7 | 24.95 | 25.79 | 38.27 | 7.08 | 2.03 | 1.04 | 1.84 | 75.05 | 5.19 |
| 8 | 8 | 24.81 | 25.88 | 37.82 | 6.96 | 1.86 | 0.89 | 1.58 | 75.19 | 5.26 |
| 9 | 9 | 12.62 | 27.03 | 41.63 | 7.45 | 4.62 | 2.19 | 3.99 | 87.38 | 5.21 |
| 10 | 10 | 10.57 | 27.50 | 43.13 | 7.66 | 5.76 | 2.75 | 5.05 | 89.43 | 5.18 |
| 11 | 11 | 19.64 | 26.76 | 39.63 | 7.13 | 3.23 | 1.53 | 2.83 | 80.36 | 5.28 |
| 12 | 12 | 15.58 | 27.12 | 40.55 | 7.25 | 3.98 | 1.89 | 3.50 | 84.42 | 5.26 |
| 13 | 13 | 4.85 | 9.28 | 39.55 | 7.31 | 11.56 | 11.08 | 17.75 | 95.15 | 3.74 |
| 14 | 14 | 3.74 | 7.23 | 37.72 | 6.79 | 12.13 | 12.42 | 19.92 | 96.26 | 3.63 |

TABLE 22

ANILINE/CYCLOHEXENE
Sorted by Pressure

| OBS | SAMPLE ID | RUN | TEMPERATURE | PRESSURE | N | R | CATALYST TYPE | LHSV | CONV | O_P |
|---|---|---|---|---|---|---|---|---|---|---|
| 1 | 7893-34-25 | 2 | 150 | 920 | 1.00 | 3.00 | H—Y | 0.13 | 1.06 | . |
| 2 | 7893-34-24 | 1 | 150 | 922 | 1.00 | 3.00 | H—Y | 0.13 | 1.02 | . |
| 3 | 7893-49-45 | 10 | 224 | 933 | 1.00 | 3.00 | H—Y | 0.06 | 89.43 | 5.18 |
| 4 | 7893-35-28 | 4 | 174 | 934 | 1.00 | 3.00 | H—Y | 0.13 | 5.29 | 8.09 |
| 5 | 7893-35-26 | 3 | 174 | 934 | 1.00 | 3.00 | H—Y | 0.13 | 5.59 | 7.80 |
| 6 | 7893-49-44 | 9 | 224 | 936 | 1.00 | 3.00 | H—Y | 0.06 | 87.38 | 5.21 |
| 7 | 7893-37-34 | 12 | 225 | 937 | 1.00 | 3.00 | H—Y | 0.13 | 84.42 | 5.26 |
| 8 | 7893-35-30 | 5 | 200 | 940 | 1.00 | 3.00 | H—Y | 0.13 | 36.25 | 7.17 |

TABLE 22-continued

ANILINE/CYCLOHEXENE
Sorted by Pressure

| OBS | SAMPLE ID | RUN | TEMPERATURE | PRESSURE | N | R | CATALYST TYPE | LHSV | CONV | O_P |
|---|---|---|---|---|---|---|---|---|---|---|
| 9 | 7893-36-31 | 6 | 200 | 940 | 1.00 | 3.00 | H—Y | 0.13 | 38.33 | 7.05 |
| 10 | 7893-48-41 | 7 | 224 | 940 | 1.00 | 3.00 | H—Y | 0.13 | 75.05 | 5.19 |
| 11 | 7893-36-32 | 11 | 225 | 940 | 1.00 | 3.00 | H—Y | 0.13 | 80.36 | 5.28 |
| 12 | 7893-48-42 | 8 | 224 | 948 | 1.00 | 3.00 | H—Y | 0.13 | 75.19 | 5.26 |
| 13 | 7893-38-36 | 13 | 250 | 950 | 1.00 | 3.00 | H—Y | 0.13 | 95.15 | 3.74 |
| 14 | 7893-38-38 | 14 | 250 | 955 | 1.00 | 3.00 | H—Y | 0.13 | 96.26 | 3.63 |

TABLE 23

ANILINE/CYCLOHEXENE ACID CAT
Sorted by Pressure

| OBS | RUN | ANILINE MOLE PCT | N-CYCLOHEX ANILINE MOLE PCT | O-CYCLOHEX ANILINE MOLE PCT | P-CYCLOHEX ANILINE MOLE PCT | N,2-DIHEX ANILINE MOLE PCT | 2,4-DIHEX ANILINE MOLE PCT | 2,6-DIHEX ANILINE MOLE PCT | CONV | O_P |
|---|---|---|---|---|---|---|---|---|---|---|
| 1 | 2 | 98.94 | 0.13 | 0.28 | 0.00 | 0.08 | 0.00 | 0.00 | 1.06 | . |
| 2 | 1 | 98.98 | 0.09 | 0.20 | 0.00 | 0.10 | 0.00 | 0.00 | 1.02 | . |
| 3 | 10 | 10.57 | 27.50 | 43.13 | 7.66 | 5.76 | 2.75 | 5.05 | 89.43 | 5.18 |
| 4 | 4 | 94.71 | 1.77 | 3.63 | 0.46 | 0.09 | 0.00 | 0.00 | 5.29 | 8.09 |
| 5 | 3 | 94.41 | 1.69 | 3.29 | 0.44 | 0.10 | 0.00 | 0.00 | 5.59 | 7.80 |
| 6 | 9 | 12.62 | 27.03 | 41.63 | 7.45 | 4.62 | 2.19 | 3.99 | 87.38 | 5.21 |
| 7 | 12 | 15.58 | 27.12 | 40.55 | 7.25 | 3.98 | 1.89 | 3.50 | 84.42 | 5.26 |
| 8 | 5 | 63.75 | 12.73 | 21.34 | 2.95 | 0.28 | 0.08 | 0.09 | 36.25 | 7.17 |
| 9 | 6 | 61.67 | 13.10 | 21.90 | 3.08 | 0.29 | 0.08 | 0.09 | 38.33 | 7.05 |
| 10 | 7 | 24.95 | 25.79 | 38.72 | 7.08 | 2.03 | 1.04 | 1.84 | 75.05 | 5.19 |
| 11 | 11 | 19.64 | 26.76 | 39.63 | 7.13 | 3.23 | 1.53 | 2.83 | 80.36 | 5.28 |
| 12 | 8 | 24.81 | 25.88 | 37.82 | 6.96 | 1.86 | 0.89 | 1.58 | 75.19 | 5.26 |
| 13 | 13 | 4.85 | 9.28 | 39.55 | 7.31 | 11.56 | 11.08 | 17.75 | 95.15 | 3.74 |
| 14 | 14 | 3.74 | 7.23 | 37.72 | 6.79 | 12.13 | 12.42 | 19.92 | 96.26 | 3.63 |

TABLE 24

ANILINE/CYCLOHEXENE
Sorted by Conversion

| OBS | SAMPLE ID | RUN | TEMPERATURE | PRESSURE | N | R | CATALYST TYPE | LHSV | CONV | O_P |
|---|---|---|---|---|---|---|---|---|---|---|
| 1 | 7893-34-24 | 1 | 150 | 922 | 1.00 | 3.00 | H—Y | 0.13 | 1.02 | . |
| 2 | 7893-34-25 | 2 | 150 | 920 | 1.00 | 3.00 | H—Y | 0.13 | 1.06 | . |
| 3 | 7893-35-28 | 4 | 174 | 934 | 1.00 | 3.00 | H—Y | 0.13 | 5.29 | 8.09 |
| 4 | 7893-35-26 | 3 | 174 | 934 | 1.00 | 3.00 | H—Y | 0.13 | 5.29 | 7.80 |
| 5 | 7893-35-30 | 5 | 200 | 940 | 1.00 | 3.00 | H—Y | 0.13 | 36.25 | 7.17 |
| 6 | 7893-36-31 | 6 | 200 | 940 | 1.00 | 3.00 | H—Y | 0.13 | 38.33 | 7.05 |
| 7 | 7893-48-41 | 7 | 224 | 940 | 1.00 | 3.00 | H—Y | 0.13 | 75.05 | 5.19 |
| 8 | 7893-48-42 | 8 | 224 | 948 | 1.00 | 3.00 | H—Y | 0.13 | 75.19 | 5.26 |
| 9 | 7893-36-32 | 11 | 225 | 940 | 1.00 | 3.00 | H—Y | 0.13 | 80.36 | 5.28 |
| 10 | 7893-37-34 | 12 | 225 | 937 | 1.00 | 3.00 | H—Y | 0.13 | 84.42 | 5.26 |
| 11 | 7893-49-44 | 9 | 224 | 936 | 1.00 | 3.00 | H—Y | 0.06 | 87.38 | 5.21 |
| 12 | 7893-49-45 | 10 | 224 | 933 | 1.00 | 3.00 | H—Y | 0.06 | 89.43 | 5.18 |
| 13 | 7893-38-36 | 13 | 250 | 950 | 1.00 | 3.00 | H—Y | 0.13 | 95.15 | 3.74 |
| 14 | 7893-38-38 | 14 | 250 | 955 | 1.00 | 3.00 | H—Y | 0.13 | 96.26 | 3.63 |

TABLE 25

ANILINE/CYCLOHEXENE ACID CAT
Sorted by Conversion

| OBS | RUN | ANILINE MOLE PCT | N—CYCLOHEX ANILINE MOLE PCT | O—CYCLOHEX ANILINE MOLE PCT | P—CYCLOHEX ANILINE MOLE PCT | N,2-DIHEX ANILINE MOLE PCT | 2,4-DIHEX ANILINE MOLE PCT | 2,6-DEHEX ANILINE MOLE PCT | CONV | O_P |
|---|---|---|---|---|---|---|---|---|---|---|
| 1 | 1 | 98.98 | 0.09 | 0.20 | 0.00 | 0.10 | 0.00 | 0.00 | 1.02 | . |
| 2 | 2 | 98.94 | 0.13 | 0.28 | 0.00 | 0.08 | 0.00 | 0.00 | 1.06 | . |
| 3 | 4 | 94.71 | 1.77 | 3.63 | 0.46 | 0.09 | 0.00 | 0.00 | 5.29 | 8.09 |
| 4 | 3 | 94.41 | 1.69 | 3.29 | 0.44 | 0.10 | 0.00 | 0.00 | 5.59 | 7.80 |
| 5 | 5 | 63.75 | 12.73 | 21.34 | 2.95 | 0.28 | 0.08 | 0.09 | 36.25 | 7.17 |
| 6 | 6 | 61.67 | 13.10 | 21.90 | 3.08 | 0.29 | 0.08 | 0.09 | 38.33 | 7.05 |
| 7 | 7 | 24.95 | 25.79 | 38.27 | 7.08 | 2.03 | 1.04 | 1.84 | 75.05 | 5.19 |
| 8 | 8 | 24.81 | 25.88 | 37.82 | 6.96 | 1.86 | 0.89 | 1.58 | 75.19 | 5.26 |
| 9 | 11 | 19.64 | 26.76 | 39.63 | 7.13 | 3.23 | 1.53 | 2.83 | 80.36 | 5.28 |
| 10 | 12 | 15.58 | 27.12 | 40.55 | 7.25 | 3.98 | 1.89 | 3.50 | 84.42 | 5.26 |
| 11 | 9 | 12.62 | 27.03 | 41.63 | 7.45 | 4.62 | 2.19 | 3.99 | 87.38 | 5.21 |
| 12 | 10 | 10.57 | 27.50 | 43.13 | 7.66 | 5.76 | 2.75 | 5.05 | 89.43 | 5.18 |
| 13 | 13 | 4.85 | 9.28 | 39.55 | 7.31 | 11.56 | 11.08 | 17.75 | 95.15 | 3.74 |
| 14 | 14 | 3.74 | 7.23 | 37.72 | 6.79 | 12.13 | 12.42 | 19.92 | 96.26 | 3.63 |

TABLE 26

ANILINE/CYCLOHEXENE
Sorted by O_P

| OBS | SAMPLE ID | RUN | TEMPERATURE | PRESSURE | N | R | CATALYST TYPE | LHSV | CONV | O_P |
|---|---|---|---|---|---|---|---|---|---|---|
| 1 | 7893-34-24 | 1 | 150 | 922 | 1.00 | 3.00 | H-Y | 0.13 | 1.02 | . |
| 2 | 7893-34-25 | 2 | 150 | 920 | 1.00 | 3.00 | H-Y | 0.13 | 1.06 | . |
| 3 | 7893-38-38 | 14 | 250 | 955 | 1.00 | 3.00 | H-Y | 0.13 | 96.26 | 3.63 |
| 4 | 7893-38-36 | 13 | 250 | 950 | 1.00 | 3.00 | H-Y | 0.13 | 95.15 | 3.74 |
| 5 | 7893-49-45 | 10 | 224 | 933 | 1.00 | 3.00 | H-Y | 0.06 | 89.43 | 5.18 |
| 6 | 7893-48-41 | 7 | 224 | 940 | 1.00 | 3.00 | H-Y | 0.13 | 75.05 | 5.19 |
| 7 | 7893-49-44 | 9 | 224 | 936 | 1.00 | 3.00 | H-Y | 0.06 | 87.38 | 5.21 |
| 8 | 7893-48-42 | 8 | 224 | 948 | 1.00 | 3.00 | H-Y | 0.13 | 75.19 | 5.26 |
| 9 | 7893-37-34 | 12 | 225 | 937 | 1.00 | 3.00 | H-Y | 0.13 | 84.42 | 5.26 |
| 10 | 7893-36-32 | 11 | 225 | 940 | 1.00 | 3.00 | H-Y | 0.13 | 80.36 | 5.28 |
| 11 | 7893-36-31 | 6 | 200 | 940 | 1.00 | 3.00 | H-Y | 0.13 | 38.33 | 7.05 |
| 12 | 7893-35-30 | 5 | 200 | 940 | 1.00 | 3.00 | H-Y | 0.13 | 36.25 | 7.17 |
| 13 | 7893-35-26 | 3 | 174 | 934 | 1.00 | 3.00 | H-Y | 0.13 | 5.59 | 7.80 |
| 14 | 7893-35-28 | 4 | 174 | 934 | 1.00 | 3.00 | H-Y | 0.13 | 5.29 | 8.09 |

TABLE 27

ANILINE/CYCLOHEXENE ACID CAT
Sorted by O_P

| OBS | RUN | ANILINE MOLE PCT | N—CYCLOHEX ANILINE MOLE PCT | O—CYCLOHEX ANILINE MOLE PCT | P—CYCLOHEX ANILINE MOLE PCT | N,2-DIHEX ANILINE MOLE PCT | 2,4-DIHEX ANILINE MOLE PCT | 2,6-DIHEX ANILINE MOLE PCT | CONV | O_P |
|---|---|---|---|---|---|---|---|---|---|---|
| 1 | 1 | 98.98 | 0.09 | 0.20 | 0.00 | 0.10 | 0.00 | 0.00 | 1.02 | . |
| 2 | 2 | 98.94 | 0.13 | 0.28 | 0.00 | 0.08 | 0.00 | 0.00 | 1.06 | . |
| 3 | 14 | 3.74 | 7.23 | 37.72 | 6.79 | 12.13 | 12.42 | 19.92 | 96.26 | 3.63 |
| 4 | 13 | 4.85 | 9.28 | 39.55 | 7.31 | 11.56 | 11.08 | 17.75 | 95.15 | 3.74 |
| 5 | 10 | 10.57 | 27.50 | 43.13 | 7.66 | 5.76 | 2.75 | 5.05 | 89.43 | 5.18 |
| 6 | 7 | 24.95 | 25.79 | 38.27 | 7.08 | 2.03 | 1.04 | 1.84 | 75.05 | 5.19 |
| 7 | 9 | 12.62 | 27.03 | 41.63 | 7.45 | 4.62 | 2.19 | 3.99 | 87.38 | 5.21 |
| 8 | 8 | 24.81 | 25.88 | 37.82 | 6.96 | 1.86 | 0.89 | 1.58 | 75.19 | 5.26 |
| 9 | 12 | 15.58 | 27.12 | 40.55 | 7.25 | 3.98 | 1.89 | 3.50 | 84.42 | 5.26 |
| 10 | 11 | 19.64 | 26.76 | 39.63 | 7.13 | 3.23 | 1.53 | 2.83 | 80.36 | 5.28 |
| 11 | 6 | 61.67 | 13.10 | 21.90 | 3.08 | 0.29 | 0.08 | 0.09 | 38.33 | 7.05 |
| 12 | 5 | 63.75 | 12.73 | 21.34 | 2.95 | 0.28 | 0.08 | 0.09 | 36.25 | 7.17 |
| 13 | 3 | 94.41 | 1.69 | 3.29 | 0.44 | 0.10 | 0.00 | 0.00 | 5.59 | 7.80 |
| 14 | 4 | 94.17 | 1.77 | 3.63 | 0.46 | 0.09 | 0.00 | 0.00 | 5.29 | 8.09 |

Tables 20–27 show the alkylation of aniline with cyclohexene. As the data shows, alkylation of aniline with cyclohexene is more sensitive to temperature than propylene but less than isobutylene. Temperatures from about 200° to 225° C. result in conversions greater then 75% with an ortho-para ratio of 5 and greater.

EXAMPLE 16

Alkylation of N-Isopropyl Aniline

A series of alkylation reactions was carried out in a fixed bed catalytic reactor, the reactor consisting of a 0.5" ID, 304 stainless steel tube which was jacketed with single-element heater. A 5 cc Vicor preheating bed was used to vaporize the reactants as they were passed downflow through the stainless steel tube jacketed reactor. The reactor was of sufficient length to accomodate from about 12–25 cubic centimeters of a solid phase catalyst system, having a particle size of from about 12–18 mesh (U.S. standard size). The reactions were conducted at temperatures ranging from about 100°–400° C. and pressures of from about 50–1000 psig and an LHSV based upon total aromatic amine liquid feed to the vaporizer of from 0.05 to 4.0 hr.$^{-1}$.

The reaction product was collected and byproduct olefin was removed via vaporization. The reaction product then was analyzed (free of olefin) by gas chromatography using an internal standard technique. Results are provided in Tables 28–31.

Temperatures, pressures, catalysts, moles, olefin and amine reactant, and other variables are recited in Table 28 and 30. Tables 29 and 31 provide analytical results with respect to the run conditions described in Table 28 and 30 respectively. In Tables 28 and 30 OBS is the sequential line observation for the particular table (there may be some skips); run is an arbitrary run number to permit rapid identification of that data set in other Tables; temperatures is in °C., pressure is in psig, G-$Al_2O_3$ refers to gamma-alumina, H-Y is a hydrogen exchanged Y zeolite, 13% $Al_2O_3/SiO_2$ refers to a silica-alumina catalyst containing 13% by weight of $Al_2O_3$. N refers to aromatic amine, i.e., aniline, R refers to olefin, i.e., propylene, X refers to N-alkylate, i.e., N-isopropylaniline, conversion (conv.) is expressed as % and is based upon the total moles ring alkylated product produced divided by the total moles of aromatic amine and N-alkylated amine feed times 100; and o-p, refers to the ortho-para ratio which is the moles of 2+2,6-isomers divided by the moles of 4-isomer+2,4-isomer+2,4,6-isomer. In some cases an ortho to para ratio of >40 has been written in, otherwise one would be dividing by zero. Tables 28 and 29 are arranged in ascending conversion. Tables 30 and 31 are duplicates of Tables 28 and 29 are arranged in ascending ortho para ratio.

Tables 28–31 illustrate the effect of various process parameters such as including catalyst activity on conversion. Other variables such as the mole ratio of olefin to total aromatic amine as well as the molar ratios of aniline to N-alkylate are shown. They are to be used in combination to observe trends; e.g., O-P ratios vs. conversion based upon reaction parameters. No one specific value is to be considered as controlling but rather is to be considered in combination with another value. The table product legends are as follows:
1. Aniline—aniline
2. N-IPA—N-isopropylaniline
3. 2-IPA—ortho-isopropylaniline
4. 4-IPA—para-isopropylaniline
5. N-2-DIPA—N,2-diisopropylaniline
6. 2,4-DIPA—2,4-diisopropylaniline
7. 2,6-DIPA—2,6-diisopropylaniline
8. 2,4,6-TIPA—2,4,6-triisopropylaniline

TABLE 28

CONVERSION OF N—ISOPROPYLANILINE
ARRANGED IN ASCENDING CONVERSION BY CATALYST TYPE

| OBS | SAMPLE ID | RUN | TEMPERATURE | PRESSURE | N | R | X | CATALYST TYPE | LHSV | CONV | O—P |
|---|---|---|---|---|---|---|---|---|---|---|---|
| 1 | 7893-73-86 | 5 | 348 | 900 | 0.50 | 0.00 | 0.50 | G-AL2O3 | 0.13 | 6.97 | >40 |
| 2 | 7893-73-87 | 20 | 349 | 905 | 0.50 | 0.00 | 0.50 | G-AL2O3 | 0.13 | 7.09 | >40 |
| 3 | 7893-75-93 | 22 | 349 | 910 | 0.75 | 2.00 | 0.25 | G-AL2O3 | 0.13 | 9.66 | 14.55 |
| 4 | 7893-75-92 | 9 | 348 | 900 | 0.75 | 2.00 | 0.25 | G-AL2O3 | 0.13 | 12.38 | 14.27 |
| 5 | 7893-75-94 | 23 | 349 | 910 | 0.75 | 2.00 | 0.25 | G-AL2O3 | 0.13 | 12.61 | >40 |
| 6 | 7893-73-88 | 6 | 348 | 30 | 0.50 | 0.00 | 0.50 | G-AL2O3 | 0.13 | 13.92 | 8.13 |
| 7 | 7893-73-89 | 7 | 348 | 30 | 0.50 | 0.00 | 0.50 | G-AL2O3 | 0.13 | 14.38 | 7.93 |
| 8 | 7893-74-90 | 21 | 349 | 930 | 0.50 | 2.00 | 0.50 | G-AL2O3 | 0.13 | 19.52 | 35.08 |
| 9 | 7893-72-83 | 2 | 348 | 30 | 0.00 | 0.00 | 1.00 | G-AL2O3 | 0.13 | 23.58 | 6.40 |
| 10 | 7893-72-82 | 1 | 348 | 30 | 0.00 | 0.00 | 1.00 | G-AL2O3 | 0.13 | 24.16 | 6.37 |
| 11 | 7893-72-84 | 3 | 348 | 955 | 0.00 | 2.00 | 1.00 | G-AL2O3 | 0.13 | 28.76 | 24.83 |
| 12 | 7893-71-79 | 18 | 349 | 960 | 0.00 | 0.00 | 1.00 | G-AL2O3 | 0.13 | 30.29 | 8.29 |
| 13 | 7893-71-80 | 19 | 349 | 960 | 0.00 | 0.00 | 1.00 | G-AL2O3 | 0.13 | 30.70 | 8.61 |
| 14 | 7893-74-91 | 8 | 348 | 925 | 0.50 | 2.00 | 0.50 | G-AL2O3 | 0.13 | 32.98 | 31.82 |
| 15 | 7893-72-85 | 4 | 348 | 960 | 0.00 | 2.00 | 1.00 | G-AL2O3 | 0.13 | 40.66 | 19.45 |
| 20 | 7893-53-50 | 10 | 348 | 980 | 0.00 | 6.90 | 1.00 | G-AL2O3 | 0.18 | 62.28 | 14.19 |
| 21 | 7893-58-52 | 11 | 348 | 860 | 0.00 | 10.00 | 1.00 | G-AL2O3 | 0.13 | 76.80 | 13.74 |
| 22 | 7893-59-54 | 12 | 348 | 990 | 0.00 | 10.00 | 1.00 | G-AL2O3 | 0.13 | 77.63 | 14.35 |
| 23 | 7893-59-56 | 13 | 348 | 990 | 0.00 | 10.00 | 1.00 | G-AL2O3 | 0.13 | 78.01 | 15.82 |
| 24 | 7893-60-61 | 15 | 348 | 980 | 0.40 | 10.00 | 0.60 | G-AL2O3 | 0.13 | 80.42 | 19.35 |
| 25 | 7893-60-59 | 14 | 348 | 990 | 0.40 | 10.00 | 0.60 | G-AL2O3 | 0.13 | 81.81 | 15.39 |
| 26 | 7893-61-65 | 17 | 348 | 1000 | 0.40 | 10.00 | 0.60 | G-AL2O3 | 0.13 | 83.85 | 14.57 |
| 27 | 7893-61-63 | 16 | 348 | 1000 | 0.40 | 10.00 | 0.60 | G-AL2O3 | 0.13 | 84.02 | 14.47 |
| 28 | 7723-31-60 | 38 | 248 | 1073 | 0.00 | 2.00 | 1.00 | H-Y | 1.50 | 4.48 | >40 |
| 29 | 7723-31-59 | 37 | 248 | 1076 | 0.00 | 2.00 | 1.00 | H-Y | 1.50 | 4.57 | >40 |
| 30 | 7723-31-58 | 36 | 248 | 1071 | 0.00 | 2.00 | 1.00 | H-Y | 1.50 | 4.91 | 747 |
| 31 | 7723-32-64 | 48 | 249 | 1014 | 0.50 | 2.00 | 0.50 | H-Y | 1.83 | 5.01 | 3.43 |
| 32 | 7723-38-89 | 35 | 247 | 1013 | 0.00 | 0.00 | 1.00 | H-Y | 0.18 | 5.95 | 3.10 |
| 33 | 7723-38-88 | 34 | 247 | 1014 | 0.00 | 0.00 | 1.00 | H-Y | 0.18 | 8.22 | 4.87 |
| 34 | 7723-29-52 | 30 | 247 | 1067 | 0.50 | 0.00 | 0.50 | H-Y | 0.18 | 8.40 | 1.66 |
| 35 | 7723-30-54 | 32 | 247 | 50 | 0.00 | 0.00 | 1.00 | H-Y | 0.18 | 8.76 | 2.72 |
| 36 | 7723-32-65 | 49 | 249 | 1015 | 0.50 | 2.00 | 0.50 | H-Y | 1.83 | 8.97 | 7.36 |
| 37 | 7723-29-50 | 28 | 247 | 40 | 0.50 | 0.00 | 0.50 | H-Y | 0.18 | 9.44 | 1.08 |
| 38 | 7723-29-51 | 29 | 247 | 40 | 0.50 | 0.00 | 0.50 | H-Y | 0.18 | 9.51 | 1.15 |
| 39 | 7723-30-53 | 31 | 247 | 1068 | 0.50 | 0.00 | 0.50 | H-Y | 0.18 | 9.60 | 1.82 |
| 40 | 7723-30-56 | 33 | 247 | 50 | 0.00 | 0.00 | 1.00 | H-Y | 0.18 | 10.01 | 3.49 |
| 41 | 7723-34-74 | 43 | 248 | 999 | 0.75 | 2.00 | 0.25 | H-Y | 0.75 | 10.40 | 9.43 |
| 42 | 7723-33-70 | 40 | 248 | 999 | 0.50 | 2.00 | 0.50 | H-Y | 0.75 | 12.16 | 7.36 |
| 43 | 7723-32-66 | 39 | 248 | 1038 | 0.50 | 2.00 | 0.50 | H-Y | 1.83 | 13.22 | 9.09 |
| 44 | 7723-34-71 | 41 | 248 | 997 | 0.50 | 2.00 | 0.50 | H-Y | 0.75 | 19.50 | 8.29 |
| 45 | 7723-34-72 | 42 | 248 | 994 | 0.50 | 2.00 | 0.50 | H-Y | 0.75 | 21.23 | 8.58 |
| 46 | 7723-34-75 | 52 | 249 | 1003 | 0.75 | 2.00 | 0.25 | H-Y | 0.75 | 22.19 | 8.88 |
| 47 | 7723-36-81 | 45 | 248 | 1035 | 0.50 | 2.00 | 0.50 | H-Y | 0.25 | 25.98 | 8.84 |
| 48 | 7723-36-79 | 44 | 248 | 1033 | 0.50 | 2.00 | 0.50 | H-Y | 0.25 | 27.49 | 7.53 |
| 49 | 7723-33-67 | 50 | 249 | 1060 | 0.00 | 2.00 | 1.00 | H-Y | 0.75 | 31.75 | 12.27 |
| 50 | 7723-33-68 | 51 | 249 | 1054 | 0.00 | 2.00 | 1.00 | H-Y | 0.75 | 32.77 | 12.34 |
| 51 | 7723-37-85 | 46 | 248 | 1013 | 0.75 | 2.00 | 0.25 | H-Y | 0.25 | 34.81 | 7.31 |
| 52 | 7723-37-87 | 47 | 248 | 1026 | 0.75 | 2.00 | 0.25 | H-Y | 0.256 | 55.48 | 7.41 |
| 53 | 7893-85-12 | 62 | 288 | 30 | 0.50 | 0.00 | 0.50 | 13% AL2O3/SIO2 | 0.18 | 15.53 | 2.63 |
| 54 | 7893-93-15 | 67 | 290 | 930 | 0.75 | 2.00 | 0.25 | 13% AL2O3/SIO2 | 2.20 | 16.97 | 13.39 |
| 55 | 7893-85-11 | 54 | 287 | 30 | 0.50 | 0.00 | 0.50 | 13% AL2O3/SIO2 | 0.18 | 17.16 | 2.63 |
| 57 | 7893-93-16 | 68 | 290 | 930 | 0.75 | 2.00 | 0.25 | 13% AL2O3/SIO2 | 2.20 | 18.73 | 9.12 |
| 59 | 7893-83-06 | 53 | 287 | 30 | 0.00 | 0.00 | 1.00 | 13% AL2O3/SIO2 | 0.18 | 25.08 | 2.34 |
| 60 | 7893-85-13 | 63 | 288 | 890 | 0.50 | 2.00 | 0.50 | 13% AL2O3/SIO2 | 1.17 | 26.69 | 9.26 |
| 61 | 7893-83-05 | 57 | 288 | 30 | 0.00 | 0.00 | 1.00 | 13% AL2O3/SIO2 | 0.18 | 27.87 | 2.30 |
| 62 | 7893-85-14 | 64 | 289 | 890 | 0.50 | 2.00 | 0.50 | 13% AL2O3/SIO2 | 1.17 | 28.99 | 9.17 |
| 63 | 7893-93-17 | 65 | 289 | 930 | 0.75 | 2.00 | 0.25 | 13% AL2O3/SIO2 | 1.10 | 32.45 | 8.44 |
| 64 | 7893-93-18 | 66 | 289 | 930 | 0.75 | 2.00 | 0.25 | 13% AL2O3/SIO2 | 1.10 | 33.83 | 8.28 |
| 65 | 7893-82-04 | 56 | 288 | 975 | 0.00 | 0.00 | 1.00 | 13% AL2O3/SIO2 | 0.18 | 50.67 | 3.83 |
| 66 | 7893-82-03 | 55 | 288 | 970 | 0.00 | 0.00 | 1.00 | 13% AL2O3/SIO2 | 0.18 | 52.45 | 3.64 |

TABLE 29

CONVERSION OF N—ISOPROPYLANILINE

| OBS | RUN | ANILINE MOLE PCT | N—IPA MOLE PCT | 2-IPA MOLE PCT | 4-IPA MOLE PCT | N,2-DIPA MOLE PCT | 2,4-DIPA MOLE PCT | 2,6-DIPA MOLE PCT | 2,4,6-TIPA MOLE PCT | CONV | O—P |
|---|---|---|---|---|---|---|---|---|---|---|---|
| 1 | 5 | 56.66 | 36.36 | 3.78 | 0.00 | 0.00 | 0.00 | 0.00 | 0.00 | 6.97 | >40 |
| 2 | 20 | 57.32 | 35.59 | 3.42 | 0.00 | 0.00 | 0.00 | 0.00 | 0.00 | 7.09 | >40 |

TABLE 29-continued

CONVERSION OF N—ISOPROPYLANILINE

| OBS | RUN | ANILINE MOLE PCT | N—IPA MOLE PCT | 2-IPA MOLE PCT | 4-IPA MOLE PCT | N,2-DIPA MOLE PCT | 2,4-DIPA MOLE PCT | 2,6-DIPA MOLE PCT | 2,4,6-TIPA MOLE PCT | CONV | O—P |
|---|---|---|---|---|---|---|---|---|---|---|---|
| 3 | 22 | 72.59 | 17.75 | 7.42 | 0.51 | 0.00 | 0.00 | 0.00 | 0.00 | 9.66 | 14.55 |
| 4 | 9 | 72.33 | 15.29 | 10.08 | 0.71 | 0.00 | 0.00 | 0.00 | 0.00 | 12.38 | 14.27 |
| 5 | 23 | 69.12 | 18.27 | 10.10 | 0.00 | 0.42 | 0.00 | 0.54 | 0.00 | 12.61 | >40 |
| 6 | 6 | 83.98 | 2.10 | 9.21 | 1.13 | 0.00 | 0.00 | 0.00 | 0.00 | 13.92 | 8.13 |
| 7 | 7 | 84.89 | 0.72 | 9.06 | 1.14 | 0.00 | 0.00 | 0.00 | 0.00 | 14.38 | 7.93 |
| 8 | 21 | 53.39 | 27.10 | 13.61 | 0.00 | 1.10 | 0.46 | 1.43 | 0.00 | 19.52 | 35.08 |
| 9 | 2 | 74.80 | 1.62 | 13.78 | 1.67 | 0.00 | 0.55 | 0.45 | 0.00 | 23.58 | 6.40 |
| 10 | 1 | 72.91 | 2.93 | 14.07 | 1.69 | 0.00 | 0.60 | 0.51 | 0.00 | 24.16 | 6.37 |
| 11 | 3 | 41.85 | 29.38 | 18.16 | 0.00 | 2.52 | 0.99 | 3.87 | 0.00 | 28.76 | 24.83 |
| 12 | 18 | 53.34 | 15.37 | 20.75 | 1.66 | 1.78 | 1.23 | 1.47 | 0.00 | 30.29 | 8.29 |
| 13 | 19 | 53.72 | 15.58 | 21.45 | 1.69 | 1.75 | 1.17 | 1.42 | 0.00 | 30.70 | 8.61 |
| 14 | 8 | 47.84 | 19.18 | 23.67 | 0.00 | 2.36 | 0.98 | 5.23 | 0.00 | 32.98 | 31.82 |
| 15 | 4 | 40.71 | 18.62 | 26.44 | 0.00 | 3.67 | 1.50 | 7.96 | 0.45 | 40.66 | 19.45 |
| 20 | 10 | 29.42 | 8.30 | 39.30 | 0.73 | 3.60 | 2.02 | 14.30 | 1.28 | 62.28 | 14.19 |
| 21 | 11 | 17.81 | 5.39 | 43.65 | 1.20 | 4.08 | 2.16 | 19.66 | 1.54 | 76.80 | 13.74 |
| 22 | 12 | 16.97 | 5.39 | 48.76 | 1.17 | 4.68 | 2.20 | 18.99 | 1.68 | 77.63 | 14.35 |
| 23 | 13 | 16.68 | 5.31 | 48.24 | 1.07 | 4.88 | 2.15 | 18.78 | 1.32 | 78.01 | 15.82 |
| 24 | 15 | 14.89 | 4.69 | 51.33 | 1.16 | 5.15 | 1.27 | 20.54 | 1.56 | 80.42 | 19.35 |
| 25 | 14 | 13.79 | 4.40 | 50.27 | 1.20 | 5.08 | 2.18 | 21.78 | 1.63 | 81.81 | 15.39 |
| 26 | 17 | 12.25 | 3.90 | 50.03 | 1.28 | 5.16 | 2.31 | 23.94 | 1.84 | 83.85 | 14.57 |
| 27 | 16 | 12.11 | 3.88 | 49.54 | 1.30 | 5.11 | 2.29 | 24.18 | 1.87 | 84.02 | 14.47 |
| 28 | 38 | 40.17 | 55.34 | 1.80 | 0.00 | 1.53 | 0.00 | 0.00 | 0.00 | 4.48 | >40 |
| 29 | 37 | 40.23 | 55.20 | 1.75 | 0.00 | 1.60 | 0.00 | 0.00 | 0.00 | 4.57 | >40 |
| 30 | 36 | 38.39 | 56.70 | 1.80 | 0.48 | 1.79 | 0.00 | 0.00 | 0.00 | 4.91 | 7.47 |
| 31 | 48 | 73.31 | 21.68 | 1.82 | 0.64 | 0.39 | 0.00 | 0.00 | 0.00 | 5.01 | 3.43 |
| 32 | 35 | 62.97 | 31.08 | 2.70 | 1.19 | 0.57 | 0.00 | 0.41 | 0.00 | 5.95 | 3.10 |
| 33 | 34 | 61.14 | 30.63 | 3.57 | 1.15 | 1.03 | 0.00 | 0.99 | 0.00 | 8.22 | 4.87 |
| 34 | 30 | 52.21 | 39.39 | 2.97 | 2.32 | 0.88 | 0.00 | 0.00 | 0.00 | 8.40 | 1.66 |
| 35 | 32 | 31.18 | 60.06 | 2.80 | 1.40 | 1.63 | 0.42 | 0.54 | 0.00 | 8.76 | 2.72 |
| 36 | 49 | 68.30 | 22.72 | 5.50 | 0.90 | 1.15 | 0.00 | 0.00 | 0.00 | 8.97 | 7.36 |
| 37 | 28 | 63.97 | 26.59 | 2.77 | 3.21 | 0.56 | 0.16 | 0.30 | 0.00 | 9.44 | 1.08 |
| 38 | 29 | 62.85 | 27.64 | 2.91 | 3.30 | 0.56 | 0.00 | 0.33 | 0.00 | 9.51 | 1.15 |
| 39 | 31 | 53.29 | 37.12 | 3.63 | 2.72 | 1.00 | 0.00 | 0.32 | 0.00 | 9.60 | 1.82 |
| 40 | 33 | 30.02 | 59.97 | 3.48 | 1.44 | 2.27 | 0.37 | 0.57 | 0.00 | 10.01 | 3.49 |
| 41 | 43 | 76.47 | 13.13 | 6.68 | 0.81 | 0.60 | 0.00 | 0.34 | 0.00 | 10.40 | 9.43 |
| 42 | 40 | 66.21 | 21.64 | 7.20 | 1.23 | 1.49 | 0.00 | 0.38 | 0.00 | 12.16 | 7.36 |
| 43 | 39 | 63.70 | 23.09 | 7.96 | 1.11 | 1.75 | 0.00 | 0.38 | 0.00 | 13.22 | 9.09 |
| 44 | 41 | 57.77 | 22.74 | 13.02 | 1.65 | 2.53 | 0.35 | 1.04 | 0.00 | 19.50 | 8.29 |
| 45 | 42 | 55.54 | 23.23 | 14.47 | 1.76 | 2.94 | 0.41 | 1.25 | 0.00 | 21.23 | 8.58 |
| 46 | 52 | 62.87 | 14.94 | 14.48 | 1.51 | 2.16 | 0.62 | 2.33 | 0.00 | 22.19 | 8.88 |
| 47 | 45 | 51.09 | 22.93 | 14.94 | 1.64 | 3.79 | 0.91 | 3.84 | 0.00 | 25.98 | 8.84 |
| 48 | 44 | 50.34 | 22.18 | 18.56 | 2.41 | 3.66 | 0.85 | 2.33 | 0.00 | 27.49 | 7.53 |
| 49 | 50 | 31.37 | 36.88 | 16.46 | 1.44 | 8.87 | 0.97 | 4.22 | 0.00 | 31.75 | 12.27 |
| 50 | 51 | 30.32 | 36.91 | 16.18 | 1.46 | 10.00 | 1.03 | 4.49 | 0.00 | 32.77 | 12.34 |
| 51 | 46 | 49.36 | 15.83 | 19.23 | 1.99 | 3.78 | 1.67 | 6.88 | 0.42 | 34.81 | 7.31 |
| 52 | 47 | 25.90 | 18.62 | 28.29 | 2.62 | 7.13 | 3.21 | 13.11 | 0.73 | 55.48 | 7.41 |
| 53 | 62 | 76.44 | 8.03 | 11.61 | 3.30 | 0.63 | 1.72 | 0.97 | 0.00 | 15.53 | 2.63 |
| 54 | 67 | 63.67 | 19.35 | 11.48 | 1.16 | 3.04 | 0.00 | 1.00 | 0.00 | 16.97 | 13.39 |
| 55 | 54 | 76.09 | 6.75 | 12.67 | 3.51 | 0.61 | 1.96 | 1.12 | 0.00 | 17.16 | 2.63 |
| 56 | 68 | 61.67 | 19.61 | 12.21 | 1.23 | 3.29 | 0.60 | 1.18 | 0.00 | 18.73 | 9.12 |
| 59 | 53 | 60.45 | 14.47 | 14.47 | 3.86 | 2.00 | 3.39 | 2.15 | 0.71 | 25.08 | 2.34 |
| 60 | 63 | 42.05 | 31.26 | 11.34 | 1.22 | 6.76 | 0.93 | 1.80 | 0.00 | 26.69 | 9.26 |
| 61 | 57 | 58.88 | 13.25 | 14.40 | 3.73 | 1.95 | 3.57 | 2.29 | 0.80 | 27.87 | 2.30 |
| 62 | 64 | 40.48 | 30.52 | 13.14 | 1.38 | 7.61 | 1.13 | 2.21 | 0.00 | 28.99 | 9.17 |
| 63 | 65 | 48.47 | 19.08 | 19.44 | 1.58 | 5.41 | 1.53 | 3.56 | 0.26 | 32.45 | 8.44 |
| 64 | 66 | 46.95 | 19.22 | 19.74 | 1.56 | 5.74 | 1.68 | 3.81 | 0.29 | 33.83 | 8.28 |
| 65 | 56 | 33.28 | 16.05 | 24.31 | 2.95 | 7.35 | 5.49 | 6.86 | 1.63 | 50.67 | 3.83 |
| 66 | 55 | 33.23 | 14.33 | 24.96 | 2.80 | 6.47 | 5.92 | 7.15 | 1.88 | 52.45 | 3.64 |

TABLE 30

CONVERSION OF N—ISOPROPYLANILINE ARRANGED IN ASCENDING ORTHO-PARA RATIO BY CATALYST TYPE

| OBS | SAMPLE ID | RUN | TEMPERATURE | PRESSURE | Molar Feed Ratio N | Molar Feed Ratio R | Molar Feed Ratio X | CATALYST TYPE | LHSV | CONV | O—P |
|---|---|---|---|---|---|---|---|---|---|---|---|
| 1 | 7893-73-86 | 5 | 348 | 900 | 0.50 | 0.00 | 0.50 | G-AL2O3 | 0.13 | 6.97 | >40 |
| 2 | 7893-73-87 | 20 | 349 | 905 | 0.50 | 0.00 | 0.50 | G-AL2O3 | 0.13 | 7.09 | >40 |
| 3 | 7893-75-94 | 23 | 349 | 910 | 0.75 | 2.00 | 0.25 | G-AL2O3 | 0.13 | 12.61 | >40 |
| 4 | 7893-72-82 | 1 | 348 | 30 | 0.00 | 0.00 | 1.00 | G-AL2O3 | 0.13 | 24.16 | 6.37 |
| 5 | 7893-72-83 | 2 | 348 | 30 | 0.00 | 0.00 | 1.00 | G-AL2O3 | 0.13 | 23.58 | 6.40 |
| 8 | 7893-73-89 | 7 | 348 | 30 | 0.50 | 0.00 | 0.50 | G-AL2O3 | 0.13 | 14.38 | 7.93 |
| 9 | 7893-73-88 | 6 | 348 | 30 | 0.50 | 0.00 | 0.50 | G-AL2O3 | 0.13 | 13.92 | 8.13 |
| 10 | 7893-71-79 | 18 | 349 | 960 | 0.00 | 0.00 | 1.00 | G-AL2O3 | 0.13 | 30.29 | 8.29 |
| 12 | 7893-71-80 | 19 | 349 | 960 | 0.00 | 0.00 | 1.00 | G-AL2O3 | 0.13 | 30.70 | 8.61 |
| 14 | 7893-58-52 | 11 | 348 | 860 | 0.00 | 10.00 | 1.00 | G-AL2O3 | 0.13 | 76.80 | 13.74 |
| 15 | 7893-53-50 | 10 | 348 | 980 | 0.00 | 6.90 | 1.00 | G-AL2O3 | 0.18 | 62.28 | 14.19 |

TABLE 30-continued

CONVERSION OF N—ISOPROPYLANILINE
ARRANGED IN ASCENDING ORTHO-PARA RATIO BY CATALYST TYPE

| OBS | SAMPLE ID | RUN | TEMPERATURE | PRESSURE | Molar Feed Ratio N | R | X | CATALYST TYPE | LHSV | CONV | O—P |
|---|---|---|---|---|---|---|---|---|---|---|---|
| 16 | 7893-75-92 | 9 | 348 | 900 | 0.75 | 2.00 | 0.25 | G-AL2O3 | 0.13 | 12.38 | 14.27 |
| 17 | 7893-59-54 | 12 | 348 | 990 | 0.00 | 10.00 | 1.00 | G-AL2O3 | 0.13 | 77.63 | 14.35 |
| 18 | 7893-61-63 | 16 | 348 | 1000 | 0.40 | 10.00 | 0.60 | G-AL2O3 | 0.13 | 84.02 | 14.47 |
| 19 | 7893-75-93 | 22 | 349 | 910 | 0.75 | 2.00 | 0.25 | G-AL2O3 | 0.13 | 9.66 | 14.55 |
| 20 | 7893-61-65 | 17 | 348 | 1000 | 0.40 | 10.00 | 0.60 | G-AL2O3 | 0.13 | 83.85 | 14.57 |
| 21 | 7893-60-59 | 14 | 348 | 990 | 0.40 | 10.00 | 0.60 | G-AL2O3 | 0.13 | 81.81 | 15.39 |
| 22 | 7893-59-56 | 13 | 348 | 990 | 0.00 | 10.00 | 1.00 | G-AL2O3 | 0.13 | 78.01 | 15.82 |
| 23 | 7893-60-61 | 15 | 348 | 980 | 0.40 | 10.00 | 0.60 | G-AL2O3 | 0.13 | 80.42 | 19.35 |
| 24 | 7893-72-85 | 4 | 348 | 960 | 0.00 | 2.00 | 1.00 | G-AL2O3 | 0.13 | 40.66 | 19.45 |
| 25 | 7893-72-84 | 3 | 348 | 955 | 0.00 | 2.00 | 1.00 | G-AL2O3 | 0.13 | 28.76 | 24.83 |
| 26 | 7893-74-91 | 8 | 348 | 925 | 0.50 | 2.00 | 0.50 | G-AL2O3 | 0.13 | 32.98 | 31.82 |
| 27 | 7893-74-90 | 21 | 349 | 930 | 0.50 | 2.00 | 0.50 | G-AL2O3 | 0.13 | 19.52 | 35.08 |
| 28 | 7723-31-59 | 37 | 248 | 1076 | 0.00 | 2.00 | 1.00 | H-y | 1.50 | 4.57 | >40 |
| 29 | 7723-31-60 | 38 | 248 | 1073 | 0.00 | 2.00 | 1.00 | H-Y | 1.50 | 4.48 | >40 |
| 30 | 7723-29-50 | 28 | 247 | 40 | 0.50 | 0.00 | 0.50 | H-Y | 0.18 | 9.44 | 1.08 |
| 31 | 7723-29-51 | 29 | 247 | 40 | 0.50 | 0.00 | 0.50 | H-Y | 0.18 | 9.51 | 1.15 |
| 32 | 7723-29-52 | 30 | 247 | 1067 | 0.50 | 0.00 | 0.50 | H-Y | 0.18 | 8.40 | 1.66 |
| 33 | 7723-30-53 | 31 | 247 | 1068 | 0.50 | 0.00 | 0.50 | H-Y | 0.18 | 9.60 | 1.82 |
| 34 | 7723-30-54 | 32 | 247 | 50 | 0.00 | 0.00 | 1.00 | H-Y | 0.18 | 8.76 | 2.72 |
| 35 | 7723-38-89 | 35 | 247 | 1013 | 0.00 | 0.00 | 1.00 | H-Y | 0.18 | 5.95 | 3.10 |
| 36 | 7723-32-64 | 48 | 249 | 1014 | 0.50 | 2.00 | 0.50 | H-Y | 1.83 | 5.01 | 3.43 |
| 37 | 7723-30-56 | 33 | 247 | 50 | 0.00 | 0.00 | 1.00 | H-Y | 0.18 | 10.01 | 3.49 |
| 38 | 7723-38-88 | 34 | 247 | 1014 | 0.00 | 0.00 | 1.00 | H-Y | 0.18 | 8.22 | 4.87 |
| 39 | 7723-37-85 | 46 | 248 | 1013 | 0.75 | 2.00 | 0.25 | H-Y | 0.25 | 34.81 | 7.31 |
| 40 | 7723-33-70 | 40 | 248 | 999 | 0.50 | 2.00 | 0.50 | H-Y | 0.75 | 12.16 | 7.36 |
| 41 | 7723-32-65 | 49 | 249 | 1015 | 0.50 | 2.00 | 0.50 | H-Y | 1.83 | 8.97 | 7.36 |
| 42 | 7723-37-87 | 47 | 248 | 1026 | 0.75 | 2.00 | 0.25 | H-Y | 0.25 | 55.48 | 7.41 |
| 43 | 7723-31-58 | 36 | 248 | 1071 | 0.00 | 2.00 | 1.00 | H-Y | 1.50 | 4.91 | 7.47 |
| 44 | 7723-36-79 | 44 | 248 | 1033 | 0.50 | 2.00 | 0.50 | H-Y | 0.25 | 27.49 | 7.53 |
| 45 | 7723-34-71 | 41 | 248 | 997 | 0.50 | 2.00 | 0.50 | H-Y | 0.75 | 19.50 | 8.29 |
| 46 | 7723-34-72 | 42 | 248 | 994 | 0.50 | 2.00 | 0.50 | H-Y | 0.75 | 21.23 | 8.58 |
| 47 | 7723-36-81 | 45 | 248 | 1035 | 0.50 | 2.00 | 0.50 | H-Y | 0.25 | 25.98 | 8.84 |
| 48 | 7723-34-75 | 52 | 249 | 1003 | 0.75 | 2.00 | 0.25 | H-Y | 0.75 | 22.19 | 8.88 |
| 49 | 7723-32-66 | 39 | 248 | 1038 | 0.50 | 2.00 | 0.50 | H-Y | 1.83 | 13.22 | 9.09 |
| 50 | 7723-34-74 | 43 | 248 | 999 | 0.75 | 2.00 | 0.25 | H-Y | 0.75 | 10.40 | 9.43 |
| 51 | 7723-33-67 | 50 | 249 | 1060 | 0.00 | 2.00 | 1.00 | H-Y | 0.75 | 31.75 | 12.27 |
| 52 | 7723-33-68 | 51 | 249 | 1054 | 0.00 | 2.00 | 1.00 | H-Y | 0.75 | 32.77 | 12.34 |
| 53 | 7893-83-05 | 57 | 288 | 30 | 0.00 | 0.00 | 1.00 | 13% AL2O3/SIO2 | 0.18 | 27.87 | 2.30 |
| 54 | 7893-83-06 | 53 | 287 | 30 | 0.00 | 0.00 | 1.00 | 13% AL2O3/SIO2 | 0.18 | 25.08 | 2.34 |
| 55 | 7893-85-12 | 62 | 288 | 30 | 0.50 | 0.00 | 0.50 | 13% AL2O3/SIO2 | 0.18 | 15.53 | 2.63 |
| 56 | 7893-85-11 | 54 | 287 | 30 | 0.50 | 0.00 | 0.50 | 13% AL2O3/SIO2 | 0.18 | 17.16 | 2.63 |
| 57 | 7893-82-03 | 55 | 288 | 970 | 0.00 | 0.00 | 1.00 | 13% AL2O3/SIO2 | 0.18 | 52.45 | 3.64 |
| 58 | 7893-82-04 | 56 | 288 | 975 | 0.00 | 0.00 | 1.00 | 13% AL2O3/SIO2 | 0.18 | 50.67 | 3.83 |
| 63 | 7893-93-18 | 66 | 289 | 930 | 0.75 | 2.00 | 0.25 | 13% AL2O3/SIO2 | 1.10 | 33.83 | 8.28 |
| 64 | 7893-93-17 | 65 | 289 | 930 | 0.75 | 2.00 | 0.25 | 13% AL2O3/SIO2 | 1.10 | 32.45 | 8.44 |
| 65 | 7893-93-16 | 68 | 290 | 930 | 0.75 | 2.00 | 0.25 | 13% AL2O3/SIO2 | 2.20 | 18.73 | 9.12 |
| 66 | 7893-85-14 | 64 | 289 | 890 | 0.50 | 2.00 | 0.50 | 13% AL2O3/SIO2 | 1.17 | 28.99 | 9.17 |
| 67 | 7893-85-13 | 63 | 288 | 890 | 0.50 | 2.00 | 0.50 | 13% AL2O3/SIO2 | 1.17 | 26.69 | 9.26 |
| 68 | 7893-93-15 | 67 | 290 | 930 | 0.75 | 2.00 | 0.25 | 13% AL2O3/SIO2 | 2.20 | 16.97 | 13.39 |

TABLE 31

CONVERSION OF N—ISOPROPYLANILINE

| OBS | RUN | ANILINE MOLE PCT | N—IPA MOLE PCT | 2-IPA MOLE PCT | 4-IPA MOLE PCT | N,2-DIPA MOLE PCT | W,4-DIPA MOLE PCT | 2,6-DIPA MOLE PCT | 2,4,6-TIPA MOLE PCT | CONV | O—P |
|---|---|---|---|---|---|---|---|---|---|---|---|
| 1 | 5 | 56.66 | 36.36 | 3.78 | 0.00 | 0.00 | 0.00 | 0.00 | 0.00 | 6.97 | >40 |
| 2 | 20 | 57.32 | 35.59 | 3.42 | 0.00 | 0.00 | 0.00 | 0.00 | 0.00 | 7.09 | >40 |
| 3 | 23 | 69.12 | 18.27 | 10.10 | 0.00 | 0.42 | 0.00 | 0.54 | 0.00 | 12.61 | >61 |
| 4 | 1 | 72.91 | 2.93 | 14.07 | 1.69 | 0.00 | 0.60 | 0.51 | 0.00 | 24.16 | 6.37 |
| 5 | 2 | 74.80 | 1.62 | 13.78 | 1.67 | 0.00 | 0.55 | 0.45 | 0.00 | 23.58 | 6.40 |
| 8 | 7 | 84.89 | 0.72 | 9.06 | 1.14 | 0.00 | 0.00 | 0.00 | 0.00 | 14.38 | 7.93 |
| 9 | 6 | 83.98 | 2.10 | 9.21 | 1.13 | 0.00 | 0.00 | 0.00 | 0.00 | 13.92 | 8.13 |
| 10 | 18 | 53.34 | 16.37 | 20.75 | 1.66 | 1.78 | 1.23 | 1.47 | 0.00 | 30.29 | 8.29 |
| 12 | 19 | 53.72 | 15.58 | 21.45 | 1.69 | 1.75 | 1.17 | 1.42 | 0.00 | 30.70 | 8.61 |
| 14 | 11 | 17.81 | 5.39 | 43.65 | 1.20 | 4.08 | 2.16 | 19.66 | 1.54 | 76.80 | 13.74 |
| 15 | 10 | 29.42 | 8.30 | 39.30 | 0.73 | 3.60 | 2.02 | 14.30 | 1.28 | 62.28 | 14.19 |
| 16 | 9 | 72.33 | 15.29 | 10.08 | 0.71 | 0.00 | 0.00 | 0.00 | 0.00 | 12.38 | 14.27 |
| 17 | 12 | 16.97 | 5.39 | 48.76 | 1.17 | 4.68 | 2.20 | 18.99 | 1.68 | 77.63 | 14.35 |
| 18 | 16 | 12.11 | 3.88 | 49.54 | 1.30 | 5.11 | 2.29 | 24.18 | 1.87 | 84.02 | 14.47 |
| 19 | 22 | 72.59 | 17.75 | 7.42 | 0.51 | 0.00 | 0.00 | 0.00 | 0.00 | 9.66 | 14.55 |
| 20 | 17 | 12.25 | 3.90 | 50.03 | 1.28 | 5.16 | 2.31 | 23.94 | 1.84 | 83.85 | 14.57 |
| 21 | 14 | 13.79 | 4.40 | 50.27 | 1.20 | 5.08 | 2.18 | 21.78 | 1.63 | 81.81 | 15.39 |
| 22 | 13 | 16.68 | 5.31 | 48.24 | 1.07 | 4.88 | 2.15 | 18.78 | 1.32 | 78.01 | 15.82 |
| 23 | 15 | 14.89 | 4.69 | 51.33 | 1.16 | 5.15 | 1.27 | 20.54 | 1.56 | 80.42 | 19.35 |
| 24 | 4 | 40.71 | 18.62 | 26.44 | 0.00 | 3.67 | 1.50 | 7.96 | 0.45 | 40.66 | 19.45 |

TABLE 31-continued

| | | | N—IPA | 2-IPA | 4-IPA | | | | | | |
|---|---|---|---|---|---|---|---|---|---|---|---|
| | | ANILINE | MOLE | MOLE | MOLE | N,2-DIPA | W,4-DIPA | 2,6-DIPA | 2,4,6-TIPA | | |
| OBS | RUN | MOLE PCT | PCT | PCT | PCT | MOLE PCT | MOLE PCT | MOLE PCT | MOLE PCT | CONV | O—P |
| 25 | 3 | 41.85 | 29.38 | 18.16 | 0.00 | 2.52 | 0.99 | 3.87 | 0.00 | 28.76 | 24.83 |
| 26 | 8 | 47.84 | 19.18 | 23.67 | 0.00 | 2.36 | 0.98 | 5.23 | 0.00 | 32.98 | 31.82 |
| 27 | 21 | 53.39 | 27.10 | 13.61 | 0.00 | 1.10 | 0.46 | 1.43 | 0.00 | 19.52 | 35.08 |
| 28 | 37 | 40.23 | 55.20 | 1.75 | 0.00 | 1.60 | 0.00 | 0.00 | 0.00 | 4.57 | >40 |
| 29 | 38 | 40.17 | 55.34 | 1.80 | 0.00 | 1.53 | 0.00 | 0.00 | 0.00 | 4.48 | >40 |
| 30 | 28 | 63.97 | 26.59 | 2.77 | 3.21 | 0.56 | 0.16 | 0.30 | 0.00 | 9.44 | 1.08 |
| 31 | 29 | 62.85 | 27.64 | 2.91 | 3.30 | 0.56 | 0.00 | 0.33 | 0.00 | 9.51 | 1.15 |
| 32 | 30 | 52.21 | 39.39 | 2.97 | 2.32 | 0.88 | 0.00 | 0.00 | 0.00 | 8.40 | 1.66 |
| 33 | 31 | 53.29 | 37.12 | 3.63 | 2.72 | 1.00 | 0.00 | 0.32 | 0.00 | 9.60 | 1.82 |
| 34 | 32 | 31.18 | 60.06 | 2.80 | 1.40 | 1.63 | 0.42 | 0.54 | 0.00 | 8.76 | 2.72 |
| 35 | 35 | 62.97 | 31.08 | 2.70 | 1.19 | 0.57 | 0.00 | 0.41 | 0.00 | 5.95 | 3.10 |
| 36 | 48 | 73.31 | 21.68 | 1.82 | 0.64 | 0.39 | 0.00 | 0.00 | 0.00 | 5.01 | 3.43 |
| 37 | 33 | 30.02 | 59.97 | 3.48 | 1.44 | 2.27 | 0.37 | 0.57 | 0.00 | 10.01 | 3.49 |
| 38 | 34 | 61.14 | 30.63 | 3.57 | 1.15 | 1.03 | 0.00 | 0.99 | 0.00 | 8.22 | 4.87 |
| 39 | 46 | 49.36 | 15.83 | 19.23 | 1.99 | 3.78 | 1.67 | 6.88 | 0.42 | 34.81 | 7.31 |
| 40 | 40 | 66.21 | 21.64 | 7.20 | 1.23 | 1.49 | 0.00 | 0.38 | 0.00 | 12.16 | 7.36 |
| 41 | 49 | 68.30 | 22.72 | 5.50 | 0.90 | 1.15 | 0.00 | 0.00 | 0.00 | 8.97 | 7.36 |
| 42 | 47 | 25.90 | 18.62 | 28.29 | 2.62 | 7.13 | 3.21 | 13.11 | 0.73 | 55.48 | 7.41 |
| 43 | 36 | 38.39 | 56.70 | 1.80 | 0.48 | 1.79 | 0.00 | 0.00 | 0.00 | 4.91 | 7.47 |
| 44 | 44 | 50.34 | 22.18 | 18.56 | 2.41 | 3.66 | 0.85 | 2.33 | 0.00 | 27.49 | 7.53 |
| 45 | 41 | 57.77 | 22.74 | 13.02 | 1.65 | 2.53 | 0.35 | 1.04 | 0.00 | 19.50 | 8.29 |
| 46 | 42 | 55.54 | 23.23 | 14.47 | 1.76 | 2.94 | 0.41 | 1.25 | 0.00 | 21.23 | 8.58 |
| 47 | 45 | 51.09 | 22.93 | 14.94 | 1.64 | 3.79 | 0.91 | 3.84 | 0.00 | 25.98 | 8.84 |
| 48 | 52 | 62.87 | 14.94 | 14.48 | 1.51 | 2.16 | 0.62 | 2.33 | 0.00 | 22.19 | 8.88 |
| 49 | 39 | 63.70 | 23.09 | 7.96 | 1.11 | 1.75 | 0.00 | 0.38 | 0.00 | 13.22 | 9.09 |
| 50 | 43 | 76.47 | 13.13 | 6.68 | 0.81 | 0.60 | 0.00 | 0.34 | 0.00 | 10.40 | 9.43 |
| 51 | 50 | 31.37 | 36.88 | 16.46 | 1.44 | 8.87 | 0.97 | 4.22 | 0.00 | 31.75 | 12.27 |
| 52 | 51 | 30.32 | 36.91 | 16.18 | 1.46 | 10.00 | 1.03 | 4.49 | 0.00 | 32.77 | 12.34 |
| 53 | 57 | 58.88 | 13.25 | 14.40 | 3.73 | 1.95 | 3.57 | 2.29 | 0.80 | 27.87 | 2.30 |
| 54 | 53 | 60.45 | 14.47 | 14.47 | 3.86 | 2.00 | 3.39 | 2.15 | 0.71 | 25.08 | 2.34 |
| 55 | 62 | 76.44 | 8.03 | 11.61 | 3.30 | 0.63 | 1.72 | 0.97 | 0.00 | 15.53 | 2.63 |
| 56 | 54 | 76.09 | 6.75 | 12.67 | 3.51 | 0.61 | 1.96 | 1.12 | 0.00 | 17.16 | 2.63 |
| 57 | 55 | 33.23 | 14.33 | 24.96 | 2.80 | 6.47 | 5.92 | 7.15 | 1.88 | 52.45 | 3.64 |
| 58 | 56 | 33.28 | 16.05 | 24.31 | 2.95 | 7.35 | 5.49 | 6.86 | 1.63 | 50.67 | 3.83 |
| 63 | 66 | 46.95 | 19.22 | 19.74 | 1.56 | 5.74 | 1.68 | 3.81 | 0.29 | 33.83 | 8.28 |
| 64 | 65 | 48.47 | 19.08 | 19.44 | 1.58 | 5.41 | 1.53 | 3.56 | 0.26 | 32.45 | 8.44 |
| 65 | 68 | 61.67 | 19.61 | 12.21 | 1.23 | 3.29 | 0.60 | 1.18 | 0.00 | 18.73 | 9.12 |
| 66 | 64 | 40.48 | 30.52 | 13.14 | 1.38 | 7.61 | 1.13 | 2.21 | 0.00 | 28.99 | 9.17 |
| 67 | 63 | 42.05 | 31.26 | 11.34 | 1.22 | 6.76 | 0.93 | 1.80 | 0.00 | 26.69 | 9.26 |
| 68 | 67 | 63.67 | 19.35 | 11.48 | 1.16 | 3.04 | 0.00 | 1.00 | 0.00 | 16.97 | 13.39 |

The above tables show the excellent activity of H-Y zeolite on effecting conversion of N-alkylate to ortho-alkylate. Conversions are much higher at a lower temperature than is obtained with other catalysts. The H-Y catalyst runs demonstrate the effect of LHSV on conversion of N-alkylates. It can be readily seen that the degree of conversion is dependent on residence time. Longer residence time, i.e., lower LHSV, brings about higher conversion of N-alkylates. Compare runs 51 and 36 (OBS 46 and 50). The table also shows that higher conversions can be obtained with H-Y than with gamma-alumina and silica-alumina at comparable temperatures and space velocities.

What is claimed is:

1. In a process for alkylating aromatic amines by contacting said aromatic amine with an olefin in the presence of a catalyst system, the improvement which comprises alkylating aromatic amines represented by the formulas:

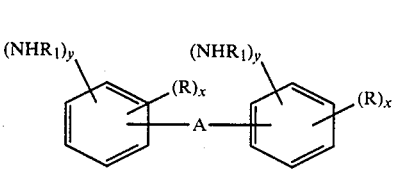

I

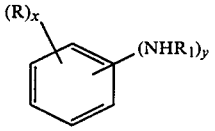

II

-continued where R is hydrogen, $C_{1-10}$ alkyl, halogen, phenyl, alkoxy, ester or nitrile; $R_1$ is hydrogen or $C_{1-10}$ alkyl, x is 0, 1 or 2; A is $C_{0-4}$ alkylene, y is 1 or 2, except one y in formula I can be zero, with an aliphatic acyclic or cyclic monoolefin in the presence of an acidic crystalline molecular sieve catalyst, said catalyst having an acidity factor of at least 0.30, said alkylation being carried out at a pressure from 50–3,000 psig.

2. The process of claim 1 wherein said acidic molecular sieve has exchangeable cation sites and said sites are populated substantially by hydrogen ion or rare earth metal cations.

3. The process of claim 2 wherein said acidic crystalline molecular sieve is an acidic crystalline alumino-silicate.

4. The process of claim 3 wherein said olefin is a $C_2$ to $C_{12}$ aliphatic acyclic or cyclic olefin.

5. The process of claim 4 wherein said reaction temperature is from 50° to 425° C.

6. The process of claim 4 where the molar ratio of olefin to aromatic amine is from about 1–10:1.

7. The process of claim 6 wherein R is $C_1$ and X is 1 or 2.

8. The process of claim 7 wherein $R_1$ is hydrogen.

9. The process of claim 4 wherein said reaction temperature does not exceed 300° C. and the acidity factor of said catalyst is at least 1.

10. The process of claim 9 wherein said olefin is a $C_4$ to $C_6$ olefin.

11. The process of claim 10 wherein said olefin is selected from the group consisting of isobutylene, isoamylene, and cyclohexene.

12. The process of claim 11 wherein said crystalline alumino-silicate is selected from the group consisting of mordenite, offretite, zeolites X, Y, and K.

13. The process of claim 12 wherein said aromatic amine is represented by formula 2.

14. The process of claim 13 wherein said aromatic amine is toluenediamine, toluidine, aniline or halogenated derivative of said aromatic amine.

15. The process of claim 14 wherein said catalyst is H-Y zeolite.

16. In a process for alkylating aromatic amines by contacting said aromatic amine with an olefin in the presence of a catalyst system, the improvement for obtaining high conversion of amine to alkylated aromatic amine a high selectivity to the orthoalkylated aromatic amine, the improvement which comprises effecting said reaction with an aromatic amine having active hydrogen atoms in positions both ortho and para to said amino group on said aromatic amine, said aromatic amine represented by the formula I and II:

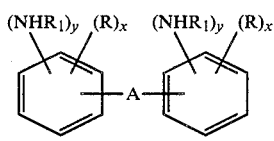
I

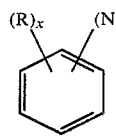
II where R is hydrogen, $C_{1-6}$ alkyl, $R_1$ is hydrogen or $C_{1-8}$ alkyl; X is 0, 1, or 2; y is 1; A is $C_{0-4}$ alkylene or NH; with a $C_2$ to $C_{12}$ mono-olefin in the presence of an acidic crystalline molecular sieve of the type having an acidity factor of at least 0.30 measured with respect to the amount of ammonia irreversibly adsorbed at 200° C. by 1 gram of molecular sieve.

17. The process of claim 16 wherein said crystalline molecular sieve is exchanged with a hydrogen or rare earth metal ion.

18. The process of claim 17 wherein the molar ratio of olefin to aromatic amine is from 1–10:1.

19. The process of claim 18 wherein the olefin is isobutylene and the reaction temperature ranges from 75° to 240° C.

20. The process of claim 18 wherein said olefin is cyclohexene and said reaction temperature ranges from 125° to 250° C.

21. The process of claim 18 wherein said olefin is propylene and said reaction temperature ranges from 125° to 300° C.

22. The process of claim 18 wherein said olefin is ethylene and said reaction temperature ranges from 250° to 425° C.

23. In a process for alkylating aromatic amines by contacting said aromatic amine with an olefin in the presence of a catalyst system, the improvement for obtaining high conversion of amine to alkylated aromatic amine and a high selectivity to ortho alkylated aromatic amine which comprises:

effecting said reaction with an aromatic amine having active hydrogen atoms in position both ortho and para to said amino group on said aromatic diamine, said aromatic amine selected from aniline or toluidine with an olefin selected from the group consisting of ethylene, propylene, isobutylene, or cyclohexene in the presence of an acidic crystalline molecular sieve of the type having an acidity factor of at least 0.30 measured with respect to the amount of ammonia irreversibility absorbed at 200° C. by 1 gram of molecular sieve.

* * * * *